United States Patent [19]

Barry et al.

[11] Patent Number: 5,463,175
[45] Date of Patent: Oct. 31, 1995

[54] GLYPHOSATE TOLERANT PLANTS

[75] Inventors: Gerard F. Barry, St. Louis; Ganesh M. Kishore, Chesterfield, both of Mo.

[73] Assignee: Monsanto Company, St. Louis, Mo.

[21] Appl. No.: 391,339

[22] Filed: Feb. 21, 1995

Related U.S. Application Data

[63] Continuation of Ser. No. 156,968, Nov. 23, 1993, abandoned, which is a continuation of Ser. No. 717,370, Jun. 24, 1991, abandoned, which is a continuation-in-part of Ser. No. 543,236, Jun. 25, 1990, abandoned.

[51] Int. Cl.$^6$ .......................... C12N 5/14; C12N 15/53; C12N 15/82; A01H 5/00
[52] U.S. Cl. .................. 800/205; 435/69.7; 435/69.8; 435/70.1; 435/172.3; 435/189; 435/240.4; 536/23.2; 536/23.4; 536/23.7; 536/24.1; 800/DIG. 13; 800/DIG. 14; 800/DIG. 17; 800/DIG. 24; 800/DIG. 26; 800/DIG. 27; 800/DIG. 31; 800/DIG. 42; 800/DIG. 43; 800/DIG. 44; 800/DIG. 48; 800/DIG. 51; 800/DIG. 56; 800/DIG. 57; 800/DIG. 58
[58] Field of Search .................. 435/69.7, 69.8, 435/70.1, 172.3, 189, 240.4; 536/23.2, 23.4, 23.7, 24.1; 800/205, DIG. 13, DIG. 14, DIG. 17, DIG. 24, DIG. 26, DIG. 27, DIG. 31, DIG. 42, DIG. 43, DIG. 44, DIG. 48, DIG. 51, DIG. 56, DIG. 57, DIG. 58

OTHER PUBLICATIONS

Quinn et al., Appl. Microbiol. Biotech., 29: 511–516 (1988).
Quin et al., Appl. Microbiol. Biotech., 31:283–287 (1989).
Talbot et al., Current Microbiol., 10: 255–260 (1984).
Weidhase et al., Zentralbl. Microbiol., 145: 433–438 (1990).
Malik et al., BioFactors, 2: 17–25 (1989).
McLean et al., J. Cell. Biochem., 13D: 338 (1989).
Botterman et al, Trend in Genetics, 4(8): 219–222 (1988).
Pipke et al., Appl. Environ. Microbiol., 54(5): 1293–1296 (1988).
Oxtoby et al., TibTech, 8(3):61–65 (1990).
Balthazor et al., Appl. Environ. Microbiol., 51:432–434 (1986).
Hallas et al., J. Industrial Microbiol., 3: 377–385 (1988).
Holben et al., Appl. Environ. Microbiol., 54: 703–711 (1988).
Jacob et al., J. Biol. Chem., 260: 5899–5905 (1985).
Kishore et al., J. Biol. Chem., 262: 12164–12168 (1987).
Lerbs et al., Arch. Microbiol., 153: 146–150 (1990).
Liu et al., Appl. Environ. Microbiol., 57: 1799–1804 (1991).
Moore et al., Appl. Environ. Microbiol., 46: 316–320 (1983).
Pipke et al., Appl. Environ. Microbiol., 53: 974–978 (1987b).
Pipke e tal., Eur. J. Biochem., 165: 267–273 (1987a).
Schowanek et al., Appl. Environ. Microbiol., 56: 895–903 (1990).
Shinabarger et al., J. Bacteriol., 168: 702–707 (1986).
Wackett et al., J. Bacteriol., 169: 710–717 (1987a).
Wackett et al., J. Bacteriol., 169: 1753–1756 (1987b).
Jacob et al. 1988. Appl. Environ. Microbiol. 54(12): 2953–2958.
Shah et al. 1986. Science 233: 478–481.
Della–Cioppa et al. 1987. Bio/Technology 5(6): 579–584.

*Primary Examiner*—David T. Fox
*Attorney, Agent, or Firm*—Dennis R. Hoerner, Jr.; Richard H. Shear

[57] ABSTRACT

Genes encoding a glyphosate oxidoreductase enzyme are disclosed. The genes are useful in producing transformed bacteria and plants which degrade glyphosate herbicide as well as crop plants which are tolerant to glyphosate herbicide.

30 Claims, 15 Drawing Sheets

SspI
6358 TCATCAAAATATTTAGCAGCATTCCAGATTGGGTTCAA

TCAACAAGGTACGAGCCATATCACTTTATTCAAATTGG

TATCGCCAAAACCAAGAAGGAACTCCCATCCTCAAAGG

TTTGTAAGGAAGAATTCTCAGTCCAAAGCCTCAACAAG

GTCAGGGTACAGAGTCTCCAAACCATTAGCCAAAAGCT

ACAGGAGATCAATGAAGAATCTTCAATCAAAGTAAACT

ACTGTTCCAGCACATGCATCATGGTCAGTAAGTTTCAG

AAAAAGACATCCACCGAAGACTTAAAGTTAGTGGGCAT

CTTTGAAAGTAATCTTGTCAACATCGAGCAGCTGGCTT

GTGGGACCAGACAAAAAGGAATGGTGCAGAATTGTT

AGGCGCACCTACCAAAAGCATCTTTGCCTTTATTGCAA

AAGATAAAGCAGATTCCTCTAGTACAAGTGGGGAACAA

AATAACGTGGAAAGAGCTGTCCTGACAGCCCACTCAC

TAATGCGTATGACGAACGCAGTGACGACCACAAAGAA

TTTTCCCTCTATATAAGAAGGCATTTCATTCCCATTTG

AAGGATCATCAGATACTAACCAATATTTCTC 6954
SspI

Figure 1

```
   1 NCATGGACGTCTGATCGAAATCGTCGTTACCGCAGCAAGGTAAGGCACGCCGAATTTTAT

61 CACCTACCGCGAAACGGTGGCTAGGCAGCGAGAGACTGTCGGCTCCGCGGGAGCATCCTA
                                                            M ("MET120")
 121 TGTCTGAGAACCACAAAAAAGTAGGCATCGCTGGAGCCGGAATCGTCGGCGTATGCACGG
      S  E  N  H  K  K  V  G  I  A  G  A  G  I  V  G  V  C  T  A
 181 CGCTGATGCTTCAGCGCCGCGGATTCAAAGTCACCTTGATTGACCCGAACCCTCCTGGCG
      L  M  L  Q  R  R  G  F  K  V  T  L  I  D  P  N  P  P  G  E
 241 AAGGTGCATCGTTTGGGAATGCCGGATGCTTCAACGGCTCATCCGTCGTCCCTATGTCCA
      G  A  S  F  G  N  A  G  C  F  N  G  S  S  V  V  P  M  S  M
 301 TGCCGGGAAACTTGACGAGCGTGCCGAAGTGGCTCCTTGACCCGATGGGGCCGTTGTCAA
      P  G  N  L  T  S  V  P  K  W  L  L  D  P  M  G  P  L  S  I
 361 TCCGGTTCAGCTATTTTCCAACCATCATGCCCTGGTTGATTCGCTTTCTGTTAGCCGGAA
      R  F  S  Y  F  P  T  I  M  P  W  L  I  R  F  L  L  A  G  R
 421 GACCAAACAAGGTGAAGGAGCAGGCGAAAGCACTCCGCAATCTCATCAAGTCCACGGTGC
      P  N  K  V  E  Q  A  K  A  L  R  N  L  I  K  S  T  V  P
 481 CTCTGATCAAGTCATTGGCGGAGGAGGCTGATGCGAGCCATCTGATCCGCCATGAAGGTC
      L  I  K  S  L  A  E  E  A  D  A  S  H  L  I  R  H  E  G  H
 541 ATCTGACCGTATATCGTGGAGAAGCAGACTTCGCCAAGGACCGCGGAGGTTGGGAACTGC
      L  T  V  Y  R  G  E  A  D  F  A  K  D  R  G  G  W  E  L  R
 601 GGCGTCTCAACGGTGTTCGCACGCAGATCCTCAGCGCCGATGCGTTGCGGGATTTCGATC
      R  L  N  G  V  R  T  Q  I  L  S  A  D  A  L  R  D  F  D  P
              SphI
 661 CGAACTTGTCGCATGCGTTTACCAAGGGCATTCTTATAGAAGAGAACGGTCACACGATTA
      N  L  S  H  A  F  T  K  G  I  L  I  E  E  N  G  H  T  I  N
                                                              EcoRI
 721 ATCCGCAAGGGCTCGTGACCCTCTTGTTTCGGCGTTTTATCGCGAACGGTGGCGAATTCG
      P  Q  G  L  V  T  L  L  F  R  R  F  I  A  N  G  G  E  F  V
 781 TATCTGCGCGTGTCATCGGCTTTGAGACTGAAGGTAGGGCGCTTAAAGGCATTACAACCA
      S  A  R  V  I  G  F  E  T  E  G  R  A  L  K  G  I  T  T  T
 841 CGAACGGCGTTCTGGCCGTTGATGCAGCGGTTGTCGCAGCCGGCGCACACTCGAAATCAT
      N  G  V  L  A  V  D  A  A  V  V  A  A  G  A  H  S  K  S  L
                                                    EcoRV
 901 TTGCTAATTCGCTAGGCGATGACATCCCGCTCGATACCGAACGTGGATATCATATCGTCA
      A  N  S  L  G  D  D  I  P  L  D  T  E  R  G  Y  H  I  V  I
 961 TCGCGAATCCGGAAGCCGCTCCACGCATTCCGACGACCGATGCGTCAGGAAAAATTCATCG
      A  N  P  E  A  A  P  R  I  P  T  T  D  A  S  G  K  F  I  A
1021 CGACACCTATGGAAATGGGGCTTCGCGTGGCGGGTACGGTTGAGTTCGCTGGGCTCACAG
      T  P  M  E  M  G  L  R  V  A  G  T  V  E  F  A  G  L  T  A
1081 CCGCTCCTAACTGGAAACGTGCGCATGTGCTCTATACGCACGCTCGAAAACTTCTTCCAG
      A  P  N  W  K  R  A  H  V  L  Y  T  H  A  R  K  L  L  P  A
1141 CCCTCGCGCCTGCGAGTTCTGAAGAACGATATTCCAAATGGATGGGGTTCCGGCCGAGCA
      L  A  P  S  S  E  E  R  Y  S  K  W  M  G  F  R  P  S  I
1201 TCCCGGATTCGCTCCCCGTGATTGGCCGGGCAACCCGGACACCCGACGTAATCTATGCTT
      P  D  S  L  P  V  I  G  R  A  T  R  T  P  D  V  I  Y  A  F
        NcoI                                              SacI
1261 TCGGCCATGGTCATCTCGGCATGACAGGGGCGCCGATGACCGCAACGCTCGTCTCAGAGC
      G  H  G  H  L  G  M  T  G  A  P  M  T  A  T  L  V  S  E  L
1321 TCCTCGCAGGCGAAAAGACCTCAATCGACATTTCGCCCTTCGCACCAAACCGCTTTGGTA
      L  A  G  E  K  T  S  I  D  I  S  P  F  A  P  N  R  F  G  I
                                                  ScaI
1381 TTGGCAAATCCAAGCAAACGGGTCCGGCAAGTTAAGTACTTACGCGGTCGTGAGTACAGC
      G  K  S  K  Q  T  G  P  A  S  *
1441 GCAGAGCCGGTGTCAAGATCAATCTGCACCTCGCAATCACCTCGGAGACGCGAAATGGCG

1501 CAAATAGAACACATATTAACAGAGTCACGCCCCGAAGCCTTTGGGTCACTACAGTCAGGCG

1561 GCCCGAGCGGGTGGATTCATTCATGTTTCCGGTCAGCTTCCGATCAAACCAGAAGGCCAG

1621 TCGGAGCAATCTGACGATCTCGTCGATAACCAGGCCAGTCTCGTTCTCCGGAATTTGCTG
          XhoI
1681 GCCGTACTCGAG
```

Figure 2

```
           fMet
  1 AGATCTCCATGGCTGAGAACCACAAAAAAGTAGGCATCGCTGGAGCCGGA  50
              ---                                T

51 ATCGTCGGCGTATGCACGGCGCTGATGCTTCAGCGCCGCGGATTCAAAGT 100
      T  T       T  TT        A   T  T

101 CACCTTGATTGACCCGAACCCTCCTGGCGAAGGTGCATCGTTTGGGAATG 150

151 CCGGATGCTTCAACGGCTCATCCGTCGTCCCTATGTCCATGCCGGGAAAC 200

201 TTGACGAGCGTGCCGAAGTGGCTCCTTGACCCGATGGGGCCGTTGTCAAT 250

251 CCGGTTCAGCTATTTTCCAACCATCATGCCCTGGTTGATTCGCTTTCTGT 300

301 TAGCCGGAAGACCAAACAAGGTGAAGGAGCAGGCGAAAGCACTCCGCAAT 350

351 CTCATCAAGTCCACGGTGCCTCTGATCAAGTCATTGGCGGAGGAGGCTGA 400

401 TGCGAGCCATCTGATCCGCCATGAAGGTCATCTGACCGTATATCGTGGAG 450

451 AAGCAGACTTCGCCAAGGACCGCGGAGGTTGGGAACTGCGGCGTCTCAAC 500

501 GGTGTTCGCACGCAGATCCTCAGCGCCGATGCGTTGCGGGATTTCGATCC 550
                      TCT  T     T     T

551 GAACTTGTCGCATGCGTTTACCAAGGGCATTCTTATAGAAGAGAACGGTC 600
    T            T
```

```
601   ACACGATTAATCCGCAAGGGCTCGTGACCCTCTTGTTTCGGCGTTTTATC   650

651   GCGAACGGTGGCGAATTTGTATCTGCGCGTGTCATCGGCTTTGAGACTGA   700
                                                    T

701   AGGTAGGGCGCTTAAAGGCATTACAACCACGAACGGCGTTCTGGCCGTTG   750
          C T  T C              T      T       T

751   ATGCAGCGGTTGTCGCAGCCGGCGCACACTCGAAATCACTTGCTAATTCG   800
          T     T      T T          T

801   CTAGGCGATGACATCCCGCTCGATACCGAACGTGGATATCATATCGTCAT   850

851   CGCGAATCCGGAAGCCGCTCCACGCATTCCGACGACCGATGCGTCAGGAA   900

901   AATTCATCGCGACACCTATGGAAATGGGGCTTCGCGTGGCGGGTACGGTT   950
                               T    T T T      T

951   GAGTTCGCTGGGCTCACAGCCGCTCCTAACTGGAAACGTGCGCATGTGCT   1000
         T    T         T

1001  CTATACGCACGCTCGAAAACTTCTTCCAGCCCTCGCGCCTGCGAGTTCTG   1050

1051  AAGAACGATATTCCAAATGGATGGGGTTCCGGCCGAGCATCCCGGATTCG   1100
                          T  T T       T  T         T

1101  CTCCCCGTGATTGGCCGGGCAACCCGGACACCCGACGTAATCTATGCTTT   1150
          T A       T T    T T

1151  CGGCCACGGTCATCTCGGCATGACAGGGGCGCCGATGACCGCAACGCTCG   1200
      T T           T        T T A    T

1201  TCTCAGAGCTCCTCGCAGGCGAAAAGACCTCAATCGACATTTCGCCCTTC   1250

1251  GCACCAAACCGCTTTGGTATTGGCAAATCCAAGCAAACGGGTCCGGCAAG   1300

1301  TTAAGTGGGAATTCAAGCTTG   1321
      ---
      STOP
```

```
  1 AGATCTCCATGGCTGAGAACCACAAAAAAGTAGGCATCGCTGGAGCCGGA   50
                             G  G  T  T              T

51 ATCGTCGGCGTATGCACGGCGCTGATGCTTCAGCGCCGCGGATTCAAAGT  100
        T  T  T     T  TT          A  T  T           G

101 CACCTTGATTGACCCGAACCCTCCTGGCGAAGGTGCATCGTTTGGGAATG  150
    T           T  A     A  A  T           T  T  C  T  C

151 CCGGATGCTTCAACGGCTCATCCGTCGTCCCTATGTCCATGCCGGGAAAC  200
      T  T          T  C     T  T  A              A

201 TTGACGAGCGTGCCGAAGTGGCTCCTTGACCCGATGGGGCCGTTGTCAAT  250
           T     T  A     T           A     T  A     C

251 CCGGTTCAGCTATTTTCCAACCATCATGCCCTGGTTGATTCGCTTTCTGT  300
           T     C                T              T CT  C

301 TAGCCGGAAGACCAAACAAGGTGAAGGAGCAGGCGAAAGCACTCCGCAAT  350
     T  T                           A  T  G        T  C

351 CTCATCAAGTCCACGGTGCCTCTGATCAAGTCATTGGCGGAGGAGGCTGA  400
              T        T              C     T

401 TGCGAGCCATCTGATCCGCCATGAAGGTCATCTGACCGTATATCGTGGAG  450
          T     C  T     T  C        C  T     G  C

451 AAGCAGACTTCGCCAAGGACCGCGGAGGTTGGGAACTGCGGCGTCTCAAC  500
                      T                    T  T

501 GGTGTTCGCACGCAGATCCTCAGCGCCGATGCGTTGCGGGATTTCGATCC  550
          T  T  A           T  A        T

551 GAACTTGTCGCATGCGTTTACCAAGGGCATTCTTATAGAAGAGAACGGTC  600
    T        T  C  C           A  C     C
```

```
601  ACACGATTAATCCGCAAGGGCTCGTGACCCTCTTGTTTCGGCGTTTTATC   650
        C  C  C   A       T       T           T     C
651  GCGAACGGTGGCGAATTTGTATCTGCGCGTGTCATCGGCTTTGAGACTGA   700
        T        A G C G   T    T      A C
701  AGGTAGGGCGCTTAAAGGCATTACAACCACGAACGGCGTTCTGGCCGTTG   750
         C T  T  C  G T  C C     C     T     T T
751  ATGCAGCGGTTGTCGCAGCCGGCGCACACTCGAAATCACTTGCTAATTCG   800
            T     T    T T          C G T         C C
801  CTAGGCGATGACATCCCGCTCGATACCGAACGTGGATATCATATCGTCAT   850
      T  T          AT G                    C C     G
851  CGCGAATCCGGAAGCCGCTCCACGCATTCCGACGACCGATGCGTCAGGAA   900
        C  C A    T          T  A T         T T
901  AATTCATCGCGACACCTATGGAAATGGGGCTTCGCGTGGCGGGTACGGTT   950
         G     T T      G    T       T T T A C
951  GAGTTCGCTGGGCTCACAGCCGCTCCTAACTGGAAACGTGCGCATGTGCT  1000
             T    T  T              G   T C T
1001 CTATACGCACGCTCGAAAACTTCTTCCAGCCCTCGCGCCTGCGAGTTCTG  1050
       C T      T GT G         T        T      C
1051 AAGAACGATATTCCAAATGGATGGGGTTCCGGCCGAGCATCCCGGATTCG  1100
          T  C   G       T   T A          A     C
1101 CTCCCCGTGATTGGCCGGGCAACCCGGACACCCGACGTAATCTATGCTTT  1150
       T A      T T T    T T A    T     C
1151 CGGCCACGGTCATCTCGGCATGACAGGGGCGCCGATGACCGCAACGCTCG  1200
        T      C    T    T T T A          C
1201 TCTCAGAGCTCCTCGCAGGCGAAAAGACCTCAATCGACATTTCGCCCTTC  1250
      T T           T G      T        C T A
1251 GCACCAAACCGGTTTGGTATTGGCAAATCCAAGCAAACGGGTCCGGCAAG  1300
             T C       T G         T       T  TC
1301 TTAAGTGGGAATTCAAGCTTG  1321
      C
```

```
         B
         g
         l
         I
         I
      AGATCTCCACAATGGCTTCCTCTATGCTCTCTTCCGCTACTATGGTTGCCTCTCCGGCTC
    1 ---------+---------+---------+---------+---------+---------+ 60
      TCTAGAGGTGTTACCGAAGGAGATACGAGAGAAGGCGATGATACCAACGGAGAGGCCGAG

MetAlaSerSerMetLeuSerSerAlaThrMetValAlaSerProAlaGln -

AGGCCACTATGGTCGCTCCTTTCAACGGACTTAAGTCCTCCGCTGCCTTCCCAGCCACCC
   61 ---------+---------+---------+---------+---------+---------+ 120
      TCCGGTGATACCAGCGAGGAAAGTTGCCTGAATTCAGGAGGCGACGGAAGGGTCGGTGGG

AlaThrMetValAlaProPheAsnGlyLeuLysSerSerAlaAlaPheProAlaThrArg -

GCAAGGCTAACAACGACATTACTTCCATCACAAGCAACGGCGGAAGAGTTAACTGCATGC
  121 ---------+---------+---------+---------+---------+---------+ 180
      CGTTCCGATTGTTGCTGTAATGAAGGTAGTGTTCGTTGCCGCCTTCTCAATTGACGTACG

LysAlaAsnAsnAspIleThrSerIleThrSerAsnGlyGlyArgValAsnCysMetGln -

AGGTGTGGCCTCCGATTGGAAAGAAGAAGTTTGAGACTCTCTCTTACCTTCCTGACCTTA
  181 ---------+---------+---------+---------+---------+---------+ 240
      TCCACACCGGAGGCTAACCTTTCTTCTTCAAACTCTGAGAGAGAATGGAAGGACTGGAAT

ValTrpProProIleGlyLysLysLysPheGluThrLeuSerTyrLeuProAspLeuThr -

N
                                        c
                                        o
                                        I
      CCGATTCCGGTGGTCGCGTCAACTGCATGCAGGCCATGG
  241 ---------+---------+---------+--------- 279
      GGCTAAGGCCACCAGCGCAGTTGACGTACGTCCGGTACC

AspSerGlyGlyArgValAsnCysMetGlnAlaMet    -
```

Figure 6

```
    B
    g
    l
    I
    I
    AGATCTATCGATAAGCTTGATGTAATTGGAGGAAGATCAAAATTTTCAATCCCCATTCTT
  1 ---------+---------+---------+---------+---------+---------+  60
    TCTAGATAGCTATTCGAACTACATTAACCTCCTTCTAGTTTTAAAAGTTAGGGGTAAGAA

CGATTGCTTCAATTGAAGTTTCTCCGATGGCGCAAGTTAGCAGAATCTGCAATGGTGTGC
 61 ---------+---------+---------+---------+---------+---------+ 120
    GCTAACGAAGTTAACTTCAAAGAGGCTACCGCGTTCAATCGTCTTAGACGTTACCACACG

MetAlaGlnValSerArgIleCysAsnGlyValGln -

AGAACCCATCTCTTATCTCCAATCTCTCGAAATCCAGTCAACGCAAATCTCCCTTATCGG
121 ---------+---------+---------+---------+---------+---------+ 180
    TCTTGGGTAGAGAATAGAGGTTAGAGAGCTTTAGGTCAGTTGCGTTTAGAGGGAATAGCC

AsnProSerLeuIleSerAsnLeuSerLysSerSerGlnArgLysSerProLeuSerVal -

TTTCTCTGAAGACGCAGCAGCATCCACGAGCTTATCCGATTTCGTCGTCGTGGGGATTGA
181 ---------+---------+---------+---------+---------+---------+ 240
    AAAGAGACTTCTGCGTCGTCGTAGGTGCTCGAATAGGCTAAAGCAGCAGCACCCCTAACT

SerLeuLysThrGlnGlnHisProArgAlaTyrProIleSerSerSerTrpGlyLeuLys -

AGAAGAGTGGGATGACGTTAATTGGCTCTGAGCTTCGTCCTCTTAAGGTCATGTCTTCTG
241 ---------+---------+---------+---------+---------+---------+ 300
    TCTTCTCACCCTACTGCAATTAACCGAGACTCGAAGCAGGAGAATTCCAGTACAGAAGAC

LysSerGlyMetThrLeuIleGlySerGluLeuArgProLeuLysValMetSerSerVal -

S
                   p
                   h
                   I
    TTTCCACGGCGTGCATGC
301 ---------+--------
    AAAGGTGCCGCACGTACG

SerThrAlaCysMet
```

Figure 9

GLYPHOSATE TOLERANT PLANTS

This is a File Wrapper Continuation of application Ser. No.08/156,968, filed Nov. 23, 1993, now abandoned, which is a continuation of application Ser. No. 07/717,370, filed Jun. 24, 1991, now abandoned, which is a continuation-in-part of application Ser. No. 07/543,236, filed Jun. 25, 1990, now abandoned.

BACKGROUND OF THE INVENTION

Recent advances in genetic engineering have provided the requisite tools to transform plants to contain foreign genes. It is now possible to produce plants which have unique characteristics of agronomic importance. Certainly, one such advantageous trait is more cost effective, environmentally compatible weed control via herbicide tolerance. Herbicide-tolerant plants may reduce the need for tillage to control weeds thereby effectively reducing soil erosion.

One herbicide which is the subject of much investigation in this regard is N-phosphonomethyl-glycine commonly referred to as glyphosate. Glyphosate inhibits the shikimic acid pathway which leads to the biosynthesis of aromatic compounds including amino acids and vitamins. Specifically, glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS).

It has been shown that glyphosate tolerant plants can be produced by inserting into the genome of the plant the capacity to produce a higher level of EPSP synthase which enzyme is preferably glyphosate tolerant (Shah et al., 1986). The introduction into plants of glyphosate degradation gene(s) could provide a means of conferring glyphosate tolerance to plants and/or to augment the tolerance of transgenic plants already expressing a glyphosate tolerant EPSP synthase depending upon the physiological effects of the degradation products.

Glyphosate metabolism (degradation) has been examined in a wide variety of plants and little degradation has been reported in most of those studies. In those instances where degradation has been reported, the initial breakdown product is usually aminomethylphosphonate (AMPA) (Coupland, 1985; Marshall et al., 1987). In these instances, it is not clear if glyphosate is metabolized by the plant or the contaminating microbes on the leaf surface to which glyphosate was applied. AMPA has been reported to be much less phytotoxic than glyphosate for most plant species (Franz, 1985) but not for all plant species (Maier, 1983; Tanaka et al., 1988). Glyphosate degradation in soils is much more extensive and rapid (Torstensson, 1985). The principal breakdown product identified is AMPA (Rueppel et al., 1977; Nomura and Hilton, 1977); a phosphonate that can be metabolized by a wide variety of microorganisms (Zeleznick et al., 1963; Mastalerz et al., 1965; Cook et al., 1978; Daughton et al., 1979a; 1979b; 1979c; Wackett et al., 1987a). A number of pure cultures of bacteria have been identified that degrade glyphosate by one of the two known routes (Moore et al., 1983; Talbot et al., 1984; Shinabarger and Braymer, 1986; Balthazor and Hallas, 1986; Kishore and Jacob, 1987; Wackett et al., 1987a; Pipke et al., 1987a; Pipke et al., 1987b; Hallas et al., 1988; Jacob et al., 1985 and 1988; Pipke and Amrhein, 1988; Quinn et al., 1988 and 1989; Lerbs et al., 1990; Schowanek and Verstraete, 1990; Weidhase et al., 1990; Liu et al., 1991). A route involving a "C-P lyase" that degrades glyphosate to sarcosine and inorganic orthophosphate (Pi) has been reported for a *Pseudomonas sp.* (Shinabarger and Braymer, 1986; Kishore and Jacob, 1987) and an *Arthrobacter sp.* (Pipke et al., 1987b). Pure cultures capable of degrading glyphosate to AMPA have been reported for a *Flavobacterium sp.* (Balthazor and Hallas, 1986), for a *Pseudomonas sp.* (Jacob et al., 1988) and for *Arthrobacter atrocyaneus* (Pipke and Amrhein, 1988). In addition, a large number of isolates that convert glyphosate to AMPA have been identified from industrial activated sludges that treat glyphosate wastes (Hallas et al., 1988). However, the number and nature of bacterial genes responsible for these degradations have not been heretofore determined nor have the gene(s) been isolated.

Hence, in one aspect, an object of the present invention is to provide novel genes which encode a glyphosate metabolizing enzyme which converts glyphosate to aminomethylphosphonate and glyoxylate.

Another object is to enhance the activity of the glyphosate metabolizing enzyme against glyphosate by replacement of specific amino acid residues.

Another object of the present invention is to provide genetically modified plants which express a gene which encodes a glyphosate metabolizing enzyme and which exhibit enhanced tolerance to glyphosate herbicide.

Another object is to demonstrate that a glyphosate metabolizing enzyme can be targeted to plastids using chloroplast transit peptides and the plastid targeted enzyme confers high level glyphosate tolerance.

A further object is to provide a method for selecting transformed plant tissue using the glyphosate metabolizing enzyme as the selectable marker in the presence of inhibitory concentrations of glyphosate.

These and other objects, aspects and features of the present invention will become evident to those skilled in the art from the following description and working examples.

SUMMARY OF THE INVENTION

The present invention provides structural DNA constructs which encode a glyphosate oxido-reductase enzyme and which are useful in producing glyphosate degradation capability in heterologous microorganisms (e.g. bacteria and plants) and in producing glyphosate tolerant plants.

In accomplishing the foregoing, there is provided, in accordance with one aspect of the present invention, a method of producing genetically transformed plants which are tolerant toward glyphosate herbicide, comprising the steps of:

(a) inserting into the genome of a plant cell a recombinant, double-stranded DNA molecule comprising
  (i) a promoter which functions in plant cells to cause the production of an RNA sequence,
  (ii) a structural DNA sequence that causes the production of an RNA sequence which encodes a glyphosate oxidoreductase enzyme,
  (iii) a 3' non-translated DNA sequence which functions in plant cells to cause the addition of polyadenylated nucleotides to the 3' end of the RNA sequence;
  where the promoter is heterologous with respect to the coding sequence and adapted to cause sufficient expression of said enzyme in plant tissue, including meristematic tissue, to enhance the glyphosate resistance of a plant cell transformed with said gene;

(b) obtaining a transformed plant cell; and (c) regenerating from the transformed plant cell a genetically transformed plant which has increased tolerance to glyphosate herbicide.

In accordance with another aspect of the present invention, there is provided a recombinant, double-stranded DNA molecule comprising in sequence:

(a) a promoter which functions in plants to cause the production of an RNA sequence;

(b) a structural DNA sequence that causes the production of an RNA sequence which encodes a glyphosate oxidoreductase enzyme; and (c) a 3' non-translated region which functions in plants to cause the addition of polyadenylated nucleotides to the 3' end of the RNA sequence.

There has also been provided, in accordance with another aspect of the present invention, bacterial and transformed plant cells that contain, respectively, DNA comprised of the above-mentioned elements (a), (b) and (c).

In accordance with yet another aspect of the present invention, differentiated plants have been provided that comprise transformed plant cells, as described above, which exhibit tolerance toward glyphosate herbicide.

In accordance with still another aspect of the present invention, there has been provided a method for selectively controlling weeds in a field containing a crop having planted crop seeds or plants comprising the steps of:

(a) planting said crop seeds or plants which are glyphosate tolerant as a result of a recombinant double-stranded DNA molecule being inserted into said crop seed or plant, said DNA molecule having
  (i) a promoter sequence which functions in plants to cause the production of an RNA sequence,
  (ii) a structural DNA sequence which causes the production of RNA which encodes a glyphosate oxidoreductase enzyme,
  (iii) a 3' non-translated region which encodes a polyadenylation signal which functions in plants to cause the addition of polyadenylated nucleotides to the 3' end of the RNA sequence,
where the promoter is heterologous with respect to the coding sequence and adapted to cause sufficient expression of said enzyme in plant tissue, including meristematic tissue, to enhance the glyphosate tolerance of a plant cell transformed with said gene; and (b) applying to said crop and weeds in said field a sufficient amount of glyphosate herbicide to control said weeds without significantly affecting said crop.

In a particularly preferred embodiment the double-stranded DNA molecule comprising a gene for plant expression comprises a structural DNA sequence encoding a fusion polypeptide containing an amino- terminal chloroplast transit peptide which is capable of causing importation of the carboxy-terminal glyphosate oxidoreductase enzyme into the chloroplast of the plant cell expressing said gene.

A further embodiment of the present invention is the use of the glyphosate oxidoreductase gene as a selectable marker to select and identify transformed plant tissue.

BRIEF DESCRIPTION OF THE DRAWINGS

FIG. 1 shows the DNA sequence for the full-length promoter of figwort mosaic virus (FMV).

FIG. 2 shows the structural DNA sequence for a glyphosate oxidoreductase gene from bacterial isolate LBAA.

FIG. 3 shows a comparison of the manipulated structural glyphosate oxidoreductase gene versus a modified glyphosate oxidoreductase gene adapted for enhanced expression in plants. The manipulated glyphosate oxidoreductase gene is displayed as the upper DNA sequence. Only the changes made in the modified gene are indicated in the lower strand of sequences.

FIG. 4 shows a comparison of the manipulated structural glyphosate oxidoreductase gene versus a synthetic glyphosate oxidoreductase gene adapted for enhanced expression in plants. The manipulated glyphosate oxidoreductase gene is displayed as the upper DNA sequence.

FIG. 6 shows the nucleotide sequence of the CTP1 chloroplast transit peptide derived from the A. thaliana SSU1A gene.

FIG. 9 shows the nucleotide sequence of the CTP2 chloroplast transit peptide derived from the A. thaliana EPSPS gene.

STATEMENT OF THE INVENTION

Figure 5:
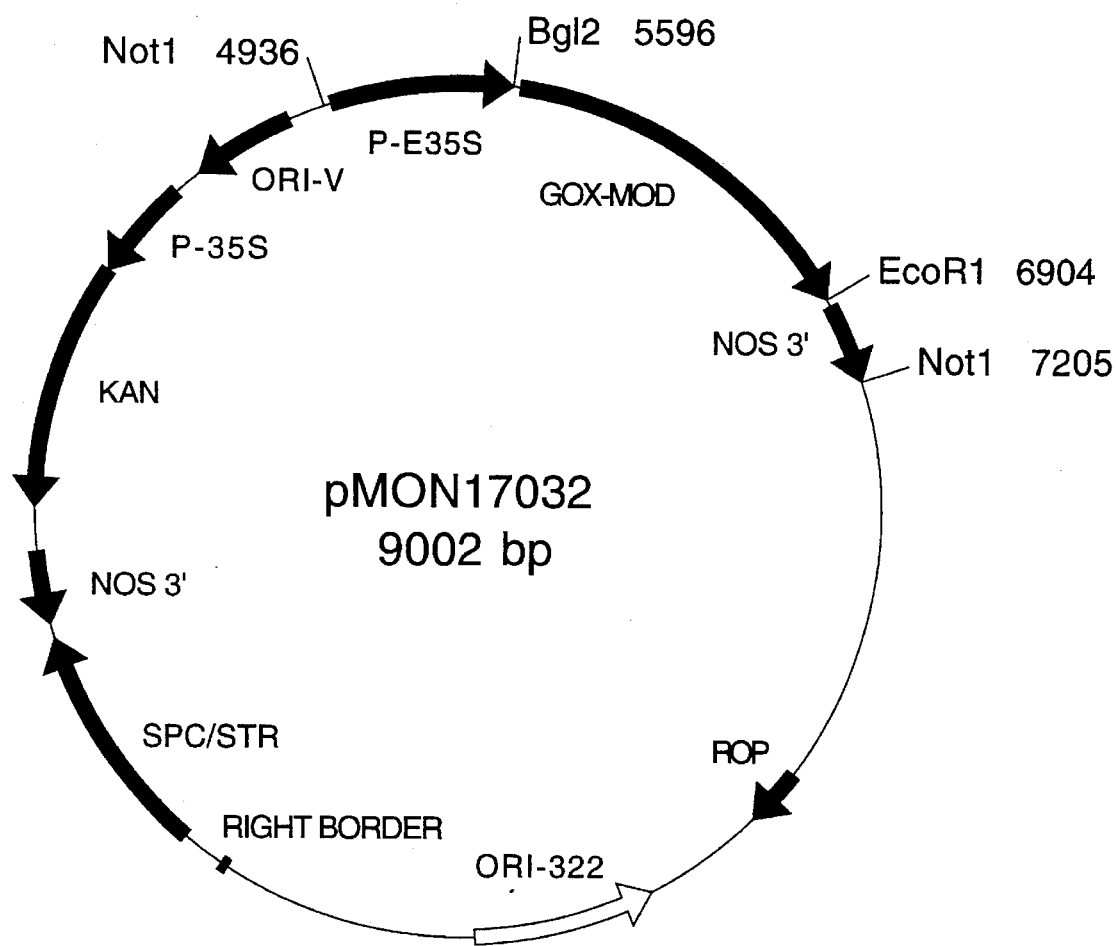
FIG. 5 shows the structure of pMON17032, a pMON886 vector containing the modified glyphosate oxidoreductase gene inserted as an En-CaMV35S-modified glyphosate oxidoreductase-NOS 3' cassette into the NotI site of the vector. The pMON886 vector is described in the text.

The expression of a plant gene which exists in double-stranded DNA form involves synthesis of messenger RNA (mRNA) from one strand of the DNA by RNA polymerase enzyme, and the subsequent processing of the mRNA primary transcript inside the nucleus. This processing involves a 3' signal region which facilitates addition of polyadenylate nucleotides to the 3' end of the RNA.

Transcription of DNA into mRNA is regulated by a region of DNA usually referred to as the "promoter." The promoter region contains a sequence of bases that signals RNA polymerase to associate with the DNA, and to initiate the transcription into mRNA using one of the DNA strands as a template to make a corresponding complementary strand of RNA.

A number of promoters which are active in plant cells have been described in the literature. These include the nopaline synthase (NOS) and octopine synthase (OCS) promoters (which are carried on tumor-inducing plasmids of *Agrobacterium tumefaciens*), the caulimovirus promoters such as the cauliflower mosaic virus (CaMV) 19S and 35S promoters and the figwort mosaic virus (FMV) 35S promoter, the light-inducible promoter from the small subunit of ribulose bisphosphate carboxylase (ssRUBISCO, a very abundant plant polypeptide). All of these promoters have been used to create various types of DNA constructs which have been expressed in plants; see, e.g., PCT publication WO 84/02913 (Rogers et al., Monsanto).

Promoters which are known or are found to cause transcription of DNA in plant cells can be used in the present invention. Such promoters may be obtained from a variety of sources such as plants and plant DNA viruses and include, but are not limited to, the CaMV35S and FMV35S promoters and promoters isolated from plant genes such as ssRUBISCO genes or the chlorophyll a/b binding proteins. As described below, it is preferred that the particular promoter selected should be capable of causing sufficient expression to result in the production of an effective amount of glyphosate oxidoreductase to render the plant substantially tolerant to glyphosate herbicides. The amount of glyphosate oxidoreductase needed to induce the desired tolerance may vary with the plant species.

It is preferred that the promoters utilized have relatively high expression in all meristematic tissues in addition to other tissues inasmuch as it is now known that glyphosate is translocated and accumulated in this type of plant tissue. Alternatively, a combination of chimeric genes can be used to cumulatively result in the necessary overall expression level of glyphosate oxidoreductase enzyme to result in the glyphosate tolerant phenotype.

The mRNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from both the 5' non-translated sequence that accompanies the promoter sequence and part of the 5' non-translated region of the virus coat protein gene. Rather, the non-translated leader sequence can be derived from an unrelated promoter or coding sequence as discussed above.

A preferred promoter for use in the present invention is the full-length transcript (35S) promoter from the figwort mosaic virus (FMV) which functions as a strong and uniform promoter for chimeric genes inserted into plants, particularly dicotyledons. In general, the resulting transgenic plants express the protein encoded by the inserted gene at a higher and more uniform level throughout the tissues and cells than the same gene driven by an enhanced CaMV35S promoter. Referring to FIG. 1, the DNA sequence of the promoter is located between nucleotides 6368 and 6930 (SEQ ID NO:1) of the FMV genome. A 5' non-translated leader sequence is preferably coupled with the promoter and an exemplary leader sequence (SEQ ID NO:2) is shown in FIG. 1. The leader sequence can be from the FMV genome itself or can be from a source other than FMV.

The 3' non-translated region of the chimeric plant gene contains a polyadenylation signal which functions in plants to cause the addition of polyadenylate nucleotides to the 3' end of the RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes such as the soybean storage protein genes and the small subunit of the ribulose-1,5-bisphosphate carboxylase (ssRUBISCO) gene. An example of a preferred 3' region is that from the ssRUBISCO gene from pea (E9), described in greater detail in the examples below.

The DNA constructs of the present invention also contain a structural coding sequence in double-stranded DNA form, which encodes a glyphosate oxidoreductase enzyme which converts glyphosate to aminomethylphosphonate and glyoxylate.

Summary of the Glyphosate Oxidoreductase Reaction

The enzyme glyphosate oxidoreductase catalyzes the cleavage of the C-N bond of glyphosate yielding aminomethyl phosphonate (AMPA) and glyoxylate as the reaction products. Under aerobic conditions, oxygen is utilized as a cosubstrate for the reaction. Other electron carriers such as phenazine methosulfate and ubiquinone stimulate the reaction under aerobic conditions. In the absence of oxygen, these compounds act as electron acceptors.

The enzymatic reaction can be assayed by oxygen uptake using an oxygen electrode. The glyphosate oxidoreductase from LBAA does not produce hydrogen peroxide as a product of oxygen reduction. This enzyme has a stoichiometry of two moles of glyphosate oxidized per mole of oxygen consumed and produces two moles each of AMPA and glyoxylate as reaction products.

An alternate method for the assay of glyphosate oxidoreductase involves reaction of the sample with 2,4-dinitrophenylhydrazine and determination of the amount of the glyoxylate-2,4-dinitrophenylhydrazone by HPLC analysis as described in detail in a later section.

A third method for the assay of glyphosate oxidoreductase consists of using $[3-^{14}C]$-glyphosate as a substrate; the radioactive AMPA produced by the enzyme is separated from the substrate by HPLC on anion exchange column as described later. The radioactivity associated with AMPA is a measure of the extent of the glyphosate oxidoreductase reaction.

Glyphosate oxidoreductase from LBAA is a flavoprotein using FAD as a cofactor. One of the mechanisms we have proposed for the reaction catalyzed by this enzyme involves the reduction of the FAD at the active site of the enzyme by glyphosate. This leads to the formation of reduced FAD and a Schiff base of aminomethylphosphonate with glyoxylate. The Schiff base is hydrated by water and hydrolyzed to its components, AMPA and glyoxylate. The reduced flavin is reoxidized by molecular oxygen. We suggest that during the process of reoxidation of reduced FAD, an oxygenated flavin is produced as an intermediate. This flavin intermediate may catalyze the oxygenation of glyphosate yielding AMPA and glyoxylate. This hypothesis is in accordance with the observed stoichiometry and our inability to detect hydrogen peroxide in the reaction mixture.

In addition to glyphosate, glyphosate oxidoreductase from LBAA oxidizes iminodiacetic acid (IDA) to glycine and glyoxylate. The rate of the reaction with IDA is significantly faster than with glyphosate.

Isolation of Efficient Glyphosate-to-AMPA Degrading Bacterium

Bacteria capable of degrading glyphosate are known. (Hallas et al., 1988; Malik et al., 1989). A number of these bacteria were screened for the rapid degradation of glyphosate in the following manner: twenty three bacterial isolates were transferred from TSA (Trypticase Soya Agar; BBL) plates into medium A consisting of Dworkin-Foster salts medium containing glucose, gluconate and citrate (each at 0.1%) as carbon source and containing glyphosate at 0.1 mM as the phosphorous source.

Dworkin-Foster minimal medium was made up by combining in 1 liter (with autoclaved H$_2$O) 1 ml each of A, B and C and 10 ml of D, thiamine HCl (5 mg), C-sources to final concentrations of 0.1% each and P-source (glyphosate or other phosphonates or Pi) to the required concentration:

| | |
|---|---|
| A. D-F Salts (1000X stock; per 100 ml; autoclaved): | |
| H3BO3 | 1 mg |
| MnSO4.7H20 | 1 mg |
| ZnSO4.7H20 | 12.5 mg |
| CUS04.5H20 | 8 mg |
| NaMoO3.3H20 | 1.7 mg |
| B. FeSO4.7H2O (1000X stock; per 100 ml; autoclaved) | 0.1 g |
| C. MgSO4.7H2O (1000X stock; per 100 ml; autoclaved) | 20 g |
| D. (NH4)2SO4 (100X stock; per 100 ml; autoclaved) | 20 g |

Yeast Extract (YE; Difco) was added to a final concentration of 0.01 or 0.001%.

Each 1 ml of culture medium also contained approximately 200,000 cpm [3-$^{14}$C]glyphosate (Amersham; CFA. 745). The cultures were incubated with shaking at 30° C. Isolate LBAA showed significant growth at day one, while other test cultures showed little growth before day three. Determination of radioactivity (by scintillation counting) in the culture, cell pellet and culture supernatant (at day 4) revealed that total $^{14}$C radioactivity had decreased and that remaining was partitioned ~1:1 in the supernatant and pellet, indicating that significant uptake and metabolism of glyphosate had taken place.

TABLE I

Glyphosate Metabolism by LBAA Culture

| Sample | $^{14}$C cpm |
|---|---|
| control | 18,631 |
| LBAA culture | 11,327 |
| LBAA supernatant | 6,007 |
| LBAA cells | 4,932 |

At day five, 75 μl of the culture supernatant of all test cultures was analyzed by HPLC as follows: a SYNCHROPAK™ AX100 anion exchange column (P. J. Cobert) was used and the mobile phase consisted of 65 mM KH$_2$PO$_4$ (pH5.5 with NaOH; depending on the needs of the experiment the concentration of the phosphate buffer was varied from 50 to 75 mM in order to alter the retention times of the material), run isocratically and the eluted material monitored continuously using a radioactive detector. This analysis revealed, in one isolate in particular (LBAA), that the glyphosate peak (Retention Time [RT]=7.0 minutes in this analysis) was completely absent and a new peak of radioactivity had appeared, with the same RT as methylamine or N-acetylmethylamine (RT=3.5 minutes). The collection of bacteria, of which strain LBAA formed a part, had been characterized as degrading glyphosate to AMPA (Hallas et al., 1988); the detection of methylamine or N-Acetylmethylamine suggested that the AMPA or N-AcetylAMPA was being metabolized by the LBAA "C-P lyase" activity to release the phosphate required for growth in this experiment. Strain LBAA was examined in greater detail.

Conversion of Glyphosate to AMPA in Microbial Isolates

For clarity and brevity of disclosure, the following description of the isolation of genes encoding glyphosate oxidoreductase enzymes is directed to the isolation of such a gene from a bacterial isolate (LBAA). Those skilled in the art will recognize that the same or a similar strategy can be utilized to isolate such genes from other microbial isolates.

The glyphosate degradation pathway was characterized in resting cells of glyphosate-grown strain LBAA as follows: the cells from a 100 ml culture of LBAA, grown in DF medium with glucose, gluconate and citrate as carbon sources and with thiamine and Yeast Extract (0.01%) to supply trace requirements (=medium DF3S) and with glyphosate at 0.2 mM as a phosphorous source, were harvested at Klett=200, washed twice with 20 ml of DF3S medium and the equivalent of 20 ml cells resuspended in 100 ul of the same medium containing [3-$^{14}$C]glyphosate (2.5 ul of 52 mCi/mmol). The cell mix was incubated at 30° C. with shaking and samples (20 ul) were withdrawn at intervals. The samples were centrifuged and both the supernatant and cell pellets were analyzed by HPLC (the cell pellets were resuspended in 100 ul of acid-DF3S [=DF3S, 0.65N HCl], boiled for 5 minutes, centrifuged briefly and this supernatant was analyzed; an acidified glyphosate control was also examined). In two hours the amount of radioactivity in the glyphosate peak (RT=7.8 minutes) in the supernatant had decreased to ~33% of the starting level; about 3% of the glyphosate was found within the cell. Material co-eluting with the methylamine standard accounted for ~5% of the starting counts in the supernatant and for ~1.5% in the cell pellet. A new peak, accounting for ~1.5% of the starting radioactivity with a RT of 7.7 minutes (glyphosate RT=8.9 minutes upon acidification in this experiment) was identified in the cell contents. The large decrease in overall radioactivity also suggested that the glyphosate was extensively metabolized in this experiment. The pathway was elucidated further in a subsequent experiment where the metabolism of [$^{14}$C]AMPA was compared to that of [3-$^{14}$C]glyphosate (as above) in resting cells harvested at Klett 165 and resuspended at the equivalent to 15 ml cells per 100 ul DF3S medium. The samples were analyzed by HPLC and consisted of whole cultures acidified and treated as described above. Within the first two hours of the glyphosate experiment, 25% of the radioactivity was found in the methylamine/N-acetylmethalamine peak (RT=4.8 minutes), 12.5% as AMPA (RT=6.4 minutes), 30% as the peak alluded to above (RT=9.4 minutes) and 30% as glyphosate (RT=11.8 minutes). In the AMPA experiment 15% of the radioactivity was found as N-acetylmethylamine/methylamine, 59% as AMPA and 18% in the peak with RT=9.4 minutes. The modified form of AMPA was identified as N-acetylAMPA. A similar acetylation step has been inferred from the products identified in E. coli growing in aminomethylphosphonates as sole sources of P (Avila et al., 1987). These data indicated that the glyphosate degradation pathway in LBAA is glyphosate→AMPA (→methylamine) →N-acetylAMPA→N-acetylmethylamine.

Cloning of the Glyphosate Oxidoreductase Gene(s) in E. coli

Having established the glyphosate-to-AMPA conversion in strain LBAA, a direct approach for the cloning of the gene(s) involved in this conversion into E. coli was investigated. Cloning and genetic techniques, unless otherwise indicated, were generally those described (Maniatis et al., 1982). The cloning strategy was as follows: introduction of a cosmid bank of strain LBAA into E. coli and selection for the glyphosate-to-AMPA gene(s) by requiring growth on glyphosate as a phosphorous (P) source. This selection relied on the use of AMPA generated by the glyphosate metabolizing enzyme as a P source, following the release of the Pi from the AMPA by the E. coli "C-P lyase." Most E. coli strains are incapable of utilizing phosphonates as P sources upon initial challenge, however these strains usually adapt rapidly, independently of RecA, to utilize phosphonates (become Mpu+)(Wackett et al., 1987b). *E. coli* Mpu+ was isolated from *E. coli* SR200 (Leu-, Pro-, recA, hsdR, supE, Sm$^r$, tonA,) as follows: an aliquot of a fresh L-broth culture of *E. coli* SR200 was plated on MOPS (Neidhardt et al., 1974) complete agar (i.e., contains L-leucine and L-proline at 25 ug/ml and vitamin B1 [thiamine] at 10 ug/ml; agar= DIFCO "Purified") containing aminomethylphosphonate (AMPA; 0.2 mM; Sigma) as P source.

MOPS medium is:

10 ml 10X MOPS SALTS
2 ml 0.5 mg/ml Thiamine HCl
1 ml 20% glucose

10 X MOPS Salts are:

for 100 ml
40 ml 1M MOPS pH7.4
4 ml 1M Tricine pH7.4
1 ml 0.01 M FeSO$_4$.7H$_2$O
5 ml 1.9 M NH$_4$Cl
1 ml 0.276 M K$_2$SO$_4$
1 ml 0.5 mM CaCl$_2$
1 ml 0.528 M MgCl$_2$
10 ml 5 M NaCl
1 ml 0.5% L-Methionine
1 ml Micronutrients Micronutrients are:

$3 \times 10^{-9}$ M (NH$_4$)$_6$Mn$_7$O$_{24}$
$4 \times 10^{-7}$ M H$_3$BO$_4$
$3 \times 10^{-8}$ M CoCl$_2$
$1.6 \times 10^{-8}$ M CuSO$_4$
$8 \times 10^{-8}$ M MnCl$_2$
$1 \times 10^{-8}$ M ZnSO$_4$ Six individual colonies were picked from this plate after three days incubation at 37° C. and streaked on MOPS complete agar containing either AMPA or methylphosphonate (Alfa) as P source. One colony, designated *E. coli* SR200 Mpu+, was chosen from those that grew equally and uniformly on both phosphonate media.

Chromosomal DNA was prepared from strain LBAA as follows: The cell pellet from a 100 ml L-Broth (Miller, 1972) late log phase culture of LBAA was resuspended in 10 ml of Solution I (Birnboim and Doly, 1979). SDS was added to a final concentration of 1% and the suspension was subjected to three freeze-thaw cycles, each consisting of immersion in dry ice for 15 minutes and in water at 70° C. for 10 minutes. The lysate was then extracted four times with equal volumes of phenol:chloroform (1:1; phenol saturated with TE) (TE=10 mM Tris pH8.0; 1.0 mM EDTA) and the phases separated by centrifugation (15000 g; 10 minutes). The ethanol-precipitable material was pelleted from the supernatant by brief centrifugation (8000 g; 5 minutes) following addition of two volumes of ethanol. The pellet was resuspended in 5 ml TE and dialyzed for 16 hours at 4° C. against 2 liters TE. This preparation yielded a 6 ml DNA solution of 150 µg/ml.

Partially-restricted DNA was prepared as follows: Three 100 µg aliquot samples of LBAA DNA were treated for 1 hour at 37° C. with restriction endonuclease HindIII at rates of 4, 2 and 1 enzyme unit/µg DNA, respectively. The DNA samples were pooled, made 0.25 mM with EDTA and extracted with equal volume of phenol:chloroform. Following the addition of NaAcetate and ethanol, the DNA was precipitated with two volumes of ethanol and pelleted by centrifugation (12000 g; 10 minutes). The dried DNA pellet was resuspended in 500 µl TE and layered on a 10–40% Sucrose gradient (in 5% increments of 5.5 ml each) in 0.5M NaCl, 50 mM Tris pH8.0, 5 mM EDTA. Following centrifugation for 20 hours at 26,000 rpm in a SW28 rotor, the tubes were punctured and 1 ml fractions collected. Fifteen µl samples of each third fraction were run on 0.8% agarose gel and the size of the DNA determined by comparison with linearized lambda DNA and HindIII-digested lambda DNA standards. Fractions containing DNA of 25–35 kb fragments were pooled, desalted on AMICON10 columns (7000 rpm; 20° C.; 45 minutes) and concentrated by precipitation. This procedure yielded 50 ug of LBAA DNA of the required size.

Plasmid pHC79 (Hohn and Collins, 1980) DNA and a HindIII-phosphatase treated vector was prepared as described elsewhere (Maniatis et al., 1982). The ligation conditions were as follows:

| | |
|---|---|
| Vector DNA (HindIII- and calf alkaline phosphatase-treated) | 1.6 µg |
| Size fractionated LBAA HindIII fragments | 3.75 µg |
| 10X ligation buffer 250 mM Tris-HCl, pH 8.0; 100 mM MgCl$_2$; 100 mM Dithiothreitol; 2 mM Spermidine | 2.2 µl |
| T4 DNA ligase (Boehringer-Mannheim) (400 units/ul) | 1.0 µl |
| H$_2$O to 22.0 µl | |
| 18 hours at 16° C. | |

The ligated DNA (4 µl) was packaged into lambda phage particles (Stratagene; Gigapack Gold) using the manufacturer's procedure.

*E. coli* SR200 Mpu+, grown overnight in L-Broth (with maltose at 0.2%), was infected with 50 µl of the packaged DNA. Transformants were selected on MOPS complete agar plus ampicillin and with glyphosate at 0.2 mM as P source.

Aliquot samples were also plated on MOPS (Neidhardt et al., 1974) complete agar plus ampicillin containing Pi at 1 mM to titer the packaged cosmids. Cosmid transformants were isolated on this latter medium at a rate of ~10$^5$ per µg/LBAA HindIII DNA after 2 days at 37° C. Colonies arose on the glyphosate agar from day 3 until day 10 with a final rate of 1 per 200–300 cosmids. Plasmid DNA was prepared from twenty one cosmid transformants from the glyphosate plates. These cosmids fell into at least two classes based on the HindIII restriction pattern of the plasmid DNA. In Class I, all the cosmids had cloned 6.4 and 4.2 kb HindIII restriction fragments in common and in Class II, a ~23 kbp fragment in common. Ten cosmids, representative of the diversity of the cloned fragments, were re-transformed into *E. coli* SR200 Mpu+ and the glyphosate utilization trait verified by selection for growth on MOPS complete agar plus ampicillin plus glyphosate plates. The final cell density achieved by the cultures using glyphosate (0.2 mM in MOPS medium) as a P source was also determined and little difference could be discerned between the different transformants. Transformants were also inoculated into MOPS complete broth with AMPA at 0.1 mM as P source (to ensure the presence of "C-P lyase" activity) and after 24 hours at 37° C. were diluted 100-fold into MOPS complete medium with glyphosate at 0.1 mM and [3-$^{14}$C]glyphosate (40,000 cpm/ml). All the cosmid-containing cells degraded glyphosate and generated N-acetylAMPA and N-acetylmethylamine, with no great difference in the rate. The N-acetylAMPA was found in the culture supernatant in these tests. One cosmid from Class I, identified as pMON7468, was chosen for further study. A second glyphosate oxidoreductase gene has been identified from a Class II cosmid clone.

Cell-free lysates E. coli SR200 Mpu+/pMON7468 were prepared from cells grown on MOPS complete medium with glyphosate at 1.0 mM (and supplemented with L-phenylalanine, L-tyrosine and L-tryptophan each at 100 µg/ml and with para-hydroxybenzoic acid, 2,3-dihydroxybenzoic acid and para-aminobenzoic acid each at 5 µg/ml to minimize the effects of inhibition of the E. coli EPSP synthase). The cell pellet (approx. 0.5 g wet weight) was resuspended in 1 ml of lysis buffer (40 mM MOPS, pH7.4; 4 mM Tricine, pH 7.4; 10% glycerol; 1 mM DTT) and passed twice through a French Press. The cell debris was removed by centrifugation at 15000 rpm for 10 minutes. The supernatant was assayed, following addition of $MgCl_2$ to 10 mM, for degradation of radiolabeled glyphosate. The glyphosate substrate was supplied as [3-$^{14}$C]glyphosate (final concentration=17 µM). The products observed were predominantly AMPA and some N-acetylAMPA; the production of AMPA is indicative of the cloned enzymatic activity from strain LBAA but the N-acetylAMPA could be due to endogenous E. coli activities (Avila et al., 1987). The specific activity for AMPA formation under these conditions was 13.3 pmoles AMPA/minute.mg protein.

Characterization of the Glyphosate-to-AMPA Gene

The cloned region responsible for this glyphosate oxidoreductase enzymatic activity was then localized in the cosmid. Deletions of pMON7468 were isolated, primarily within the cloned region, by using restriction enzymes that cut infrequently within the insert, as follows: plasmid DNA samples of 0.5–2 µg were digested to completion with restriction endonucleases NotI, SacI, BglII or BamHI, extracted with phenol:chloroform, ethanol precipitated, resuspended in TE buffer and ligated for 2–4 hours at room temperature (or for 18 hours at 16° C.) in a final volume of 50 µl with ligation buffer and T4 DNA ligase. Transformants were selected in E. coli SR200 Mpu+ and these deletions were examined for loss or retention of the glyphosate utilization phenotype. These data, in conjunction with restriction mapping of the clones, were used to localize the active region to near the central portion of the insert in pMON7468 that included the two common HindIII fragments (6.4 and 4.2 kb). The HindIII restriction fragments from this region were then subcloned into pBlueScript (Stratagene) and their glyphosate phenotype determined in E. coli JM101 Mpu+ (the Mpu+ derivative of JM101 was isolated as described for SR200 Mpu+). Clones containing the 6.4 kb HindIII fragment, in either orientation, resulted in glyphosate utilization. Following restriction mapping of this HindIII fragment, a series of deletion clones were isolated from the two 6.4 kb HindIII clones using enzymes that cut infrequently in the insert and also in the polylinker region. A number of restriction fragments internal to the HindIII fragment were also subcloned. The 3.5 kb PstI and 2.5 kb BglII fragments, in either orientation, were positive for glyphosate utilization. These data, combined with those from the deletions, were used to localize the active region to an approximately 1.8 kb BglII-XhoI fragment. In addition, deletions isolated from the 6.4 kb HindIII fragment indicated a minimum coding region size of around 0.7 kb, with the EcoRI and SacI sites probably located within the coding sequences.

The direction of transcription/expression of the locus responsible for the glyphosate-to-AMPA enzymatic activity was determined as follows: E. coli JM101 Mpu+0 transformants of pMON7469 #1 and #4 (Clones of the 2.5 kb BglII fragment in the BamHI site of pUC118; opposite orientations) were grown in M9-glucose-thiamine- ampicillin broth, with and without the Plac inducer IPTG, harvested in late log phase (Klett 190–220), cell-free lysates of the four cultures were prepared as described above and were assayed for glyphosate-to-AMPA activity with glyphosate at 17 µM. The highest enzymatic activity was obtained for pMON7469 #1 plus IPTG, where the XhoI site is distal to the Plac, suggesting that the gene(s) were expressed in the BglII-to-XhoI direction.

TABLE II

Glyphosate to AMPA Activity in Cell-Free Lysates of E. coli Transformants

| Clone | IPTG added | Specific Activity pmoles AMPA/min.mg |
|---|---|---|
| pMON7469#1 | no | <3.0 |
| pMON7469#1 | yes | 32.0 |
| pMON7469#4 | no | <3.0 |
| pMON7469#4 | yes | <3.0 |

The only product observed was AMPA, suggesting that the AMPA acetylating activity that was described earlier had been induced in E. coli transformants growing on glyphosate as the P source.

In a later experiment, cell lysates of pMON7469#1 and pMON7470 (BglII-XhoI 1.8 kb in pUC118; formed from pMON7469 #1 by deletion of the ~700 bp XhoI-SalI fragment) were assayed for glyphosate-to-AMPA activity with glyphosate at 2 mM (Sp. Act. [3-$^{14}$C]glyphosate=3.7 mCi/mmol; 0.2 µCi/reaction; cultures grown with IPTG in medium) and much higher enzymatic activities were recorded, reflecting the improved assay conditions.

TABLE III

Glyphosate to AMPA Activity in Cell-Free Lysates of E. coli Transformants

| Clone | Specific Activity nmoles AMPA/min.mg |
|---|---|
| pMON7469#1 | 15.04 |
| pMON7470 | 7.15 |

The proteins encoded by the BglII fragment were determined in vivo using a T7 expression system (Tabor and Richardson, 1985) following cloning of this fragment into the BamHI site in the vector pBlueScript (+) (pMON7471 #1, #2; opposite orientations). Test and control plasmids were transformed into E. coli K38 containing pGP1–2 (Tabor and Richardson, 1985) and grown at 30° C. in L-broth (2 ml) with ampicillin and kanamycin (100 and 50 µg/ml, respectively) to a Klett reading of ~50. An aliquot was removed and the cells collected by centrifugation, washed with M9 salts (Miller, 1972) and resuspended in 1 ml M9 medium containing glucose at 0.2%, thiamine at 20 µg/ml and containing the 18 amino acids at 0.01% (minus cysteine and methionine). Following incubation at 30° C. for 90 minutes, the cultures were transferred to a 42° C. water bath and held there for 15 minutes. Rifampicin (Sigma) was added to 200 µg/ml and the cultures held at 42° C. for 10 additional minutes and then transferred to 30° C. for 20 minutes. Samples were pulsed with 10 µCi of $^{35}$S-methionine for 5 minutes at 30° C., the cells collected by centrifugation and suspended in 60–120 µl cracking buffer (60 mM Tris-HCl 6.8/1% SDS/1% 2-mercaptoethanol/10% glycerol/0.01% bromophenol blue). Aliquot samples were electrophoresed on 12.5% SDS-PAGE and following soaking for 60 minutes in 10 volumes of Acetic Acid-Methanol-water (10:30:60), the gel was soaked in ENLIGHTNING™

(DUPONT) following manufacturer's directions, dried, and exposed at −70° C. to X-Ray Film. Proteins labeled using $^{35}$S-methionine were detected only for the BglII-to-XhoI direction, the largest about 45 kd in size. When the BglII-XhoI fragment was examined following cloning into the BamHI-XhoI sites of pBlueScript (to form pMON7472), this ~45 kd protein was still expressed.

The effect of expression of the glyphosate-to-AMPA activity on glyphosate tolerance of E. coli was determined initially by examining the growth of recombinants in media containing inhibitory concentrations of glyphosate. The test compared the growth of E. coli JM101 containing a control vector (pUC118; Viera and Messing, 1987) or the pUC118 clones of the 2.5 kb BglII fragment (pMON7469 #1, #4). There was a very clear correlation between the glyphosate-utilization ability and glyphosate tolerance. This tolerance phenotype (resistance to 15 mM glyphosate) was then employed as a screen to quickly monitor for the phenotype of deletion clones such as pMON7470 (BglII-XhoI 1.8 kb in pUC118; formed from pMON7469 #1 by deletion of the ~700 bp XhoI-SalI fragment) and later clones.

Nucleotide Sequence of the Structural Glyphosate Oxidoreductase Gene

The nucleotide sequence of the BglII-XhoI fragment (SEQ ID NO:3) was determined using single-stranded DNA templates (generated using the phagemid clones and the "helper" M13 phage R408) and the commercially available SEQUENASE™ (International Biotechnologies, Inc.) kit. Computer analysis of the sequence (SEQ ID NO:3) revealed a single large open reading frame (ORF) in the BglII to XhoI direction and is presented in FIG. 2 which includes the location of some of the relevant restriction sites. The putative stop codon (UAA) was located 2 bp 5' of the ScaI restriction cut site. Data to confirm that this UAA codon was the termination codon of the ~45 kd ORF were derived as follows: previously the 3' limits had been determined, based on the glyphosate utilization phenotype, to be between the SacI site (95 bp upstream of the ScaI site) and the XhoI site. When the BglII-ScaI fragment was cloned into the BamHI-ScaI sites of pBlueScript and the proteins expressed in vivo, the ~45 kd protein was still produced. The BglII-ScaI fragment was then recloned from this pBlueScript clone as XbaI-HindIII into pUC118 XbaI-HindIII and was found to confer resistance to 15 mM glyphosate to E. coli JM101 transformants. These data located the C-terminus of the ~45 kd protein between the SacI and ScaI sites. The only stop codon, in any reading frame, between these sites is that immediately upstream of the ScaI site.

There were two methionine codons (AUG; located at positions 120 and 186) that if used as the fMet would give rise to proteins of 46.140 and 44.002 kd, respectively, but neither was preceded by a clearly recognizable Shine-Dalgarno sequence.

The start of the protein was delineated more precisely as follows: BglII restriction site recognition sequences were introduced at positions upstream of the two potential start codons by site-directed mutagenesis of pMON7470, substituting AGATCT for the sequences AGACTG ("Bg120") and GTATGC ("Bg186"), 21 and 9 bp upstream of the $AUG_{120}$ and $AUG_{186}$, respectively. Except where noted, oligonucleotide primers for mutagenesis comprised the sequences to be altered flanked by 8–10 homologous bases on each side. The glyphosate tolerance was determined for the mutated clones. Introduction of the BglII site upstream of $AUG_{120}$ had no effect on glyphosate tolerance while it was abolished by the mutagenesis that introduced the BglII site upstream of $AUG_{186}$. The effects of these mutageneses on the ~45 kd protein were examined by subcloning the mutated sequences into T7 expression vectors using a site in the polylinker of pMON7470 (KpnI), just upstream of the original BglII site, and the downstream HindIII site. This complete fragment was recloned into p18UT3T7 (PHARMACIA) KpnI-HindIII and tested in vivo as described above. The ~45 kd protein was still expressed and at comparable levels from both of the "BglII" mutagenized sequences. When the new BglII sites were used as 5' ends (and the downstream HindIII site) for cloning into the pBlueScript BamHI-HindIII sites, the ~45 kd protein was still expressed when the new BglII site upstream of $AUG_{120}$ served as 5' end, but not when that located upstream of $AUG_{186}$ was the 5' end. These data suggest strongly that the $AUG_{120}$ (or some codon located very dose to it) is the N-terminus of the glyphosate oxidoreductase protein. The BglII site introduced upstream of the $AUG_{186}$ did not result in a prematurely terminated or highly unstable protein and suggests that the predicted coding sequence changes resulting from this mutagenesis ($Val_{18}$-$Cys_{19}$→$Arg_{18}$-$Ala_{19}$) had severe effects on the activity of the enzyme.

Further data to confirm the location of the N-terminus were obtained by introducing separately (by mutageneses of pMON7470), an NcoI restriction site recognition sequence (CCATGG for CTATGT; changes the second codon from Serine to Alanine) or an NdeI sequence (CATATG for CCTATG) at $AUG_{120}$ and expressing this ORF using efficient E. coli expression vectors. The expression of the NdeI version is outlined here: the NdeI-HindIII fragment, beginning at the putative AUG, was cloned into pMON2123 (NdeI-HindIII) replacing the ompF-IGF-1 fusion fragment (Wong et al., 1988). The resultant clone was introduced into E. coli JM101 and the cells induced with nalidixic acid as described (Wong et al., 1988) for 2 hours. The resultant protein was indistinguishable in size from the ~45 kd protein on SDS PAGE and a cell lysate from an induced culture had a glyphosate oxidoreductase specific activity of 12.8 nmoles AMPA/min.mg. When compared in a separate experiment, no differences were observed for the glyphosate oxidoreductase activity when the second codon was Alanine instead of Serine. The structural DNA sequence for the glyphosate oxidoreductase enzyme (SEQ ID NO:4) begins at nucleotide 120 and ends at nucleotide 1415 of the BglII-XhoI fragment of FIG. 2 and the glyphosate oxidoreductese enzyme consists of 431 amino acids (SEQ ID NO:5).

Construction of Glyphosate Oxidoreductase Plant Gene Transformation Vectors

To facilitate the manipulation of the structural glyphosate oxidoreductase gene, the internal EcoRI and NcoI restriction site recognition sequences were removed by site-directed mutagenesis to substitute the sequence GAATTT for GAATTC and CCACGG for CCATGG, respectively. A glyphosate oxidoreductase coding sequence suitable for introduction into and expression in plant transformation vectors was assembled in the following way: the NcoI ("Met-Ala") N-terminus was combined with the NcoI- and EcoRI-deleted coding sequences, and the C-terminus deleted to the ScaI site, in a number of cloning steps using the internal SphI and EcoRV restriction sites. In these steps a BglII site was located immediately upstream of the NcoI site and EcoRI and HindIII sites were located immediately downstream from the stop codon. The sequence of this manipulated glyphosate oxidoreductase gene (SEQ ID NO:6) is shown in FIG. 3. The manipulated glyphosate oxidoreductase gene still codes for the wild-type glyphosate oxidoreductase protein. The manipulations do not alter the amino acid sequence of the glyphosate oxidoreductase. This glyphosate oxidoreductase structural sequence (SEQ ID NO:6), as a BglII/NcoI-EcoRI/HindIII fragment of 1321 bp, numbers, respectively.

TABLE IV

Primers to Modify the Glyphosate Oxidoreductase Gene Coding Sequence

PRIMER 1 (149–210; 38–99)
CGCTGGAGCT GGAATCGTTG GTGTATGCAC TGCTTTGATG CTTCAACGTC GTGGATTCAA AG (SEQ ID NO: 27)
PRIMER 2 (623–687; 512–576)
GCAGATCCTC TCTGCTGATG CTTTGCGTGA TTTCGATCCT AACTTGTCGC ATGCTTTTAC CAAGG (SEQ ID NO: 28)
PRIMER 3 (792–832; 681–721)
GTCATCGGTT TTGAGACTGA AGGTCGTGCT CTCAAAGGCA T (SEQ ID NO: 29)
PRIMER 4 (833–901; 722–790)
TACAACCACT AACGGTGTTC TGGCTGTTGA TGCAGCTGTT GTTGCAGCTG GTGCACACTC TAAATCACT (SEQ ID NO: 30)
PRIMER 5 (1031–1091; 920–980)
GGAAATGGGT CTTCGTGTTG CTGGTACTGT TGAGTTTGCT GGTCTCACAG CTGCTCCTAA c (SEQ ID NO: 31)
PRIMER 6 (1179–12M; 1068–1135)
TGGATGGGTT TTCGTCCTAG CATTCCTGAT TCTCTTCCAG TGATTGGTCG TGCAACTCGT ACACCCGA (SEQ ID NO: 32)
PRIMER 7 (1247–1315; 1136–1204)
CGTAATCTAT GCTTTTGGTC ACGGTCATCT CGGTATGACA GGTGCTCCAA TGACTGCAAC TCTCGTCTC (SEQ ID NO: 33)

is readily cloned into an appropriate plant expression cassette. This glyphosate oxidoreductase gene (SEQ ID NO:6) was cloned as a BglII-EcoRI fragment into the plant transformation and expression vector pMON979 to form pMON17073.

Modification and Resynthesis of the Glyphosate Oxidoreductase Gene Sequence

The glyphosate oxidoreductase gene from LBAA contains sequences that could be inimical to high expression of the gene in plants. These sequences include potential polyadenylation sites that are often A+T-rich, a higher G+C% than that frequently found in plant genes (56% versus ~50%), concentrated stretches of G and C residues, and codons that are not used frequently in plant genes. The high G+C% in the glyphosate oxidoreductase gene has a number of potential consequences including the following: a higher usage of G or C than that found in plant genes in the third position in codons, and the potential to form strong hair-pin structures that may affect expression or stability of the RNA. The reduction in the G+C content of the glyphosate oxidoreductase gene, the disruption of stretches of G's and C's, the elimination of potential polyadenylation sequences, and improvements in the codon usage to that used more frequently in plant genes, could result in higher expression of glyphosate oxidoreductase in plants.

In the first phase of this experiment, selected regions of the gene were modified by site-directed mutagenesis. These modifications were directed primarily (but not exclusively) at reducing the G+C% and at breaking up some of the G+C clusters. The manipulated glyphosate oxidoreductase gene was first recloned into the phagemid vector pMON7258 as a NcoI-HindIII fragment to form pMON17014. Single stranded DNA was prepared from a dut ung E. coli strain. Seven regions of the gene were modified by site-directed mutagenesis using the primers listed in Table IV and the Bio Rad mutagenesis kit (Catalog #170-3576) and following the protocols provided with this kit.

For the sake of clarity, the reverse complement of the actual primers is presented. The base positions, in the sequences presented in FIG. 2 and in FIG. 3, corresponding to the primers are indicated by the first and second set of The resultant gene (SEQ ID NO:7) was confirmed by sequencing and by the ability to provide comparable glyphosate tolerance levels as the manipulated glyphosate oxidoreductase gene control. This modified gene (SEQ ID NO:7) is referred to as "modified glyphosate oxidoreductase." The G+C% of the glyphosate oxidoreductase gene (SEQ ID NO:6) was reduced from ~56% in the manipulated version to ~52% in the modified version (SEQ ID NO:7). A comparison of the manipulated and modified glyphosate oxidoreductase gene is shown in FIG. 3, with the manipulated version on top and the changes introduced to make the modified version on the bottom. This modified glyphosate oxidoreductase gene was cloned as a BglII-EcoRI fragment into a plant expression cassette comprising the En-CaMV35S promoter and the NOS 3' sequences. This cassette was then cloned as a NotI fragment into the pMON886 vector to form pMON17032 (FIG. 5).

A synthetic glyphosate oxidoreductase gene (SEQ ID NO:8) was designed to change as completely as possible those inimical sequences discussed above. In summary, the gene sequence was redesigned to eliminate as much as possible the following sequences or sequence features (while avoiding the introduction of unnecessary restriction sites): stretches of G's and C's of 5 or greater; A+T rich regions (predominantly) that could function as polyadenylation sites or potential RNA destabilization region, and codons not frequently found in plant genes. A comparison of the manipulated (SEQ ID NO:6) and synthetic (SEQ ID NO:8) glyphosate oxidoreductase genes is presented in FIG. 4, with the manipulated gene (SEQ ID NO:6) on top and the differences introduced into the synthetic gene (SEQ ID NO:8) on the bottom. The G+C% for the synthetic glyphosate oxidoreductase gene is ~51% and the potential to form short, high energy, hair-pin structures is reduced. This synthetic gene was cloned as a BglII-EcoRI fragment into pMON979 to form pMON17065 for introduction into plants.

Expression of Chloroplast Directed Glyphosate Oxidoreductase

The glyphosate target in plants, the 5-enolpyruvylshikimate-3-phosphate synthase (EPSPS) enzyme, is located in the chloroplast. Although glyphosate oxidoreductase activity located in the cytoplasm reduces/prevents glyphosate from reaching the chloroplast in the transgenic plant, directing the glyphosate oxidoreductase enzyme to the chloroplast has been found to further minimize the effects of glyphosate on EPSP synthase. Many chloroplast-localized proteins are expressed from nuclear genes as precursors and are targeted to the chloroplast by a chloroplast transit peptide (CTP) that is removed during the import steps. Examples of such chloroplast proteins include the small subunit (SSU) of Ribulose-1,5-bisphosphate carboxylase (RUBISCO), 5-enol-pyruvylshikimate-3-phosphate synthase (EPSPS), Ferredoxin, Ferredoxin oxidoreductase, the Light-harvesting-complex protein I and protein II, and Thioredoxin F. It has been demonstrated in vivo and in vitro that non-chloroplast proteins may be targeted to the chloroplast by use of protein fusions with a CTP and that a CTP sequence is sufficient to target a protein to the chloroplast (della-Cioppa et al., 1987).

Figure 7:
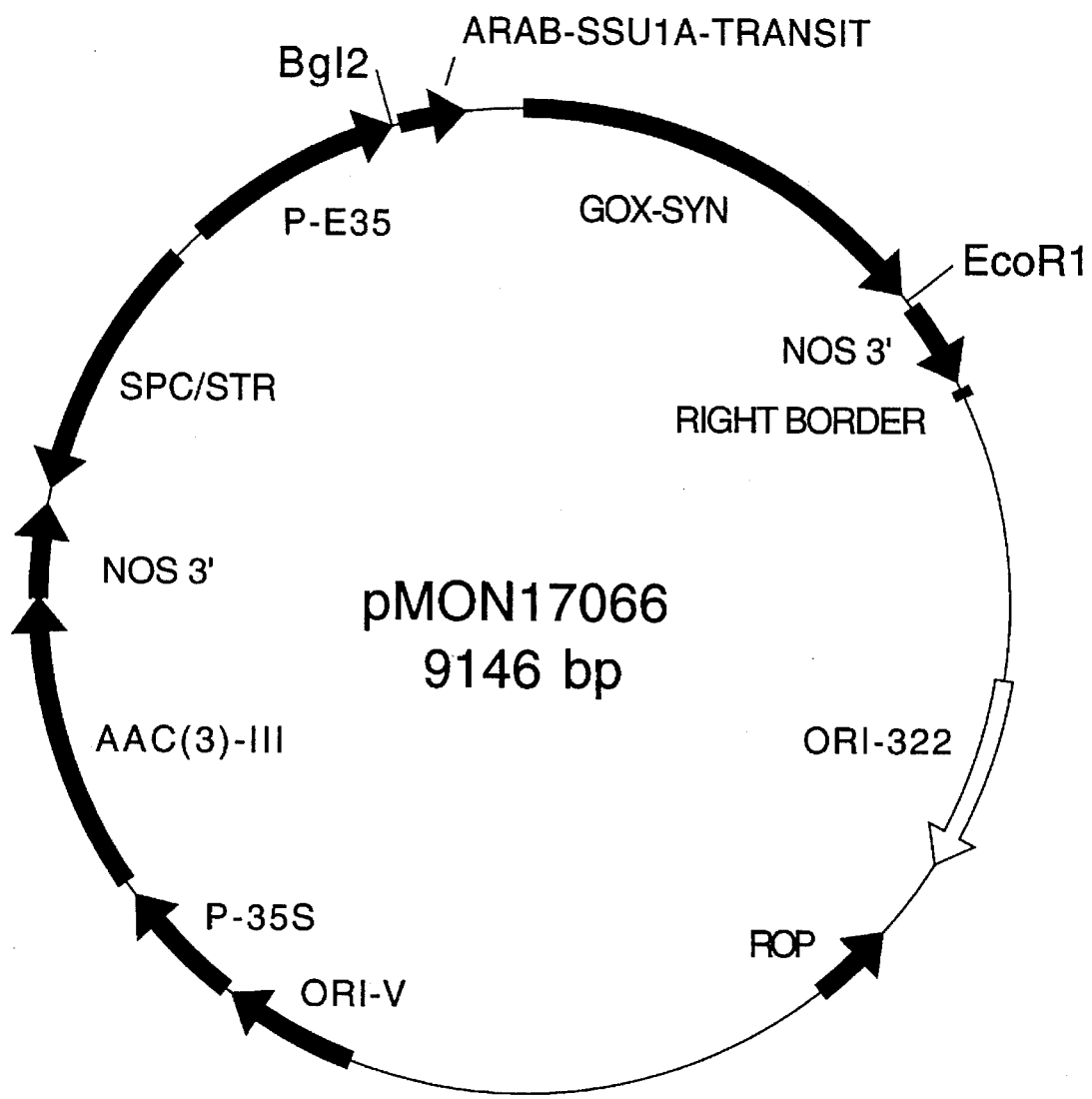
FIG. 7 shows the genetic/structural map of plasmid pMON17066, a pMON979-type vector containing a gene encoding a CTP/synthetic glyphosate oxidoreductase fusion polypeptide. Related pMON979-type derivatives are pMON17065 and pMON 17073.
Figure 8:
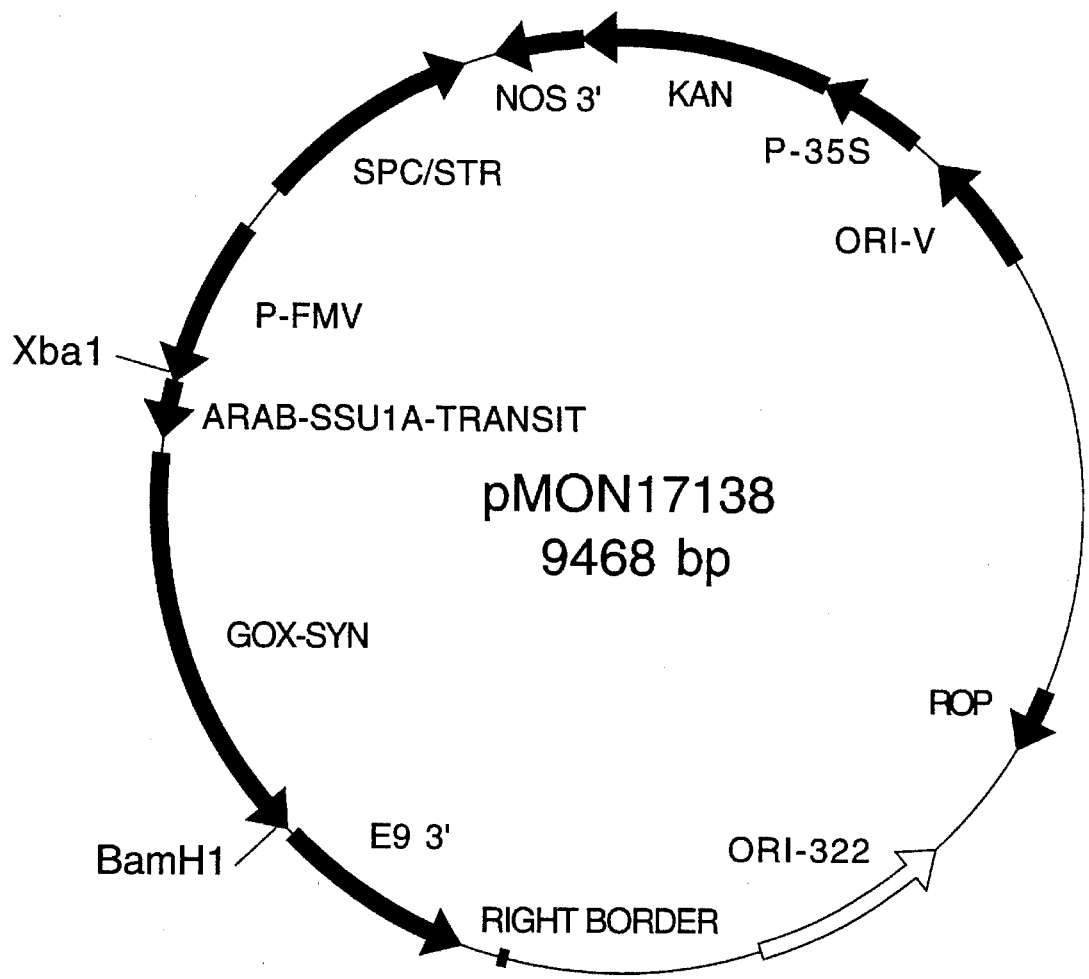
FIG. 8 shows the genetic/structural map of plasmid pMON17138, an example of a pMON981-type vector containing a gene encoding a CTP/synthetic glyphosate oxidoreductase fusion polypeptide. In this example the CTP1-synthetic glyphosate oxidoreductase gene has been cloned into pMON979 as a XbaI-BamHI fragment.

The glyphosate oxidoreductase protein was targeted to the chloroplast by construction of a fusion between the C-terminus of a CTP and the N-terminus of glyphosate oxidoreductase. In the first example, a specialized CTP, derived from the SSU 1A gene from *Arabidopsis thaliana* (Timko et al., 1988) was used. This CTP (designated CTP1) was constructed by a combination of site-directed mutageneses. The CTP1 structure (SEQ ID NO:9) (FIG. 6) is made up of the SSU 1A CTP (amino acids 1–55), the first 23 amino acids of the mature SSU 1A protein (amino acids 56–78), a serine residue (amino acid 79), a new segment that repeats amino acids 50 to 56 from the SSU 1A CTP and the first two amino acids from the mature protein (amino acids 80–87), and an alanine and methionine residue (amino acids 88 and 89). An NcoI restriction site is located at the 3' end (spans the Met codon) to facilitate the construction of precise fusions to the 5' of glyphosate oxidoreductase or other genes. At a later stage, a BglII site was introduced upstream of the N terminus of the SSU 1A sequences to facilitate the introduction of the fusions into plant transformation vectors. A fusion was assembled between the CTP1 (SEQ ID NO:9) and the manipulated glyphosate oxidoreductase (SEQ ID NO:6) (through the NcoI site) in the pGEM3zf(+) vector to form pMON17034. This vector may be transcribed in vitro using the SP6 polymerase and the RNA translated with $^{35}$S-Methionine to provide material that may be evaluated for import into chloroplasts isolated from *Lactuca sativa* using the methods described hereinafter (della-Cioppa et al., 1986, 1987). This CTP1-glyphosate oxidoreductase fusion was indeed found to be imported into chloroplasts at about 9% efficiency of that of the control, $^{35}$S labeled PreEPSPS (pMON6140; della-Cioppa et al., 1986). A CTP1-glyphosate oxidoreductase fusion was then assembled with the synthetic glyphosate oxidoreductase gene (SEQ ID NO:8) and this was introduced as a BglII-EcoRI fragment into plant vector pMON979 to form pMON17066 (FIG. 7). Following an intermediate cloning step to acquire more cloning sites, this CTP1-glyphosate oxidoreductase fusion was also cloned as a XbaI-BamHI site into pMON981 to form pMON17138 (FIG. 8).

Figure 12:
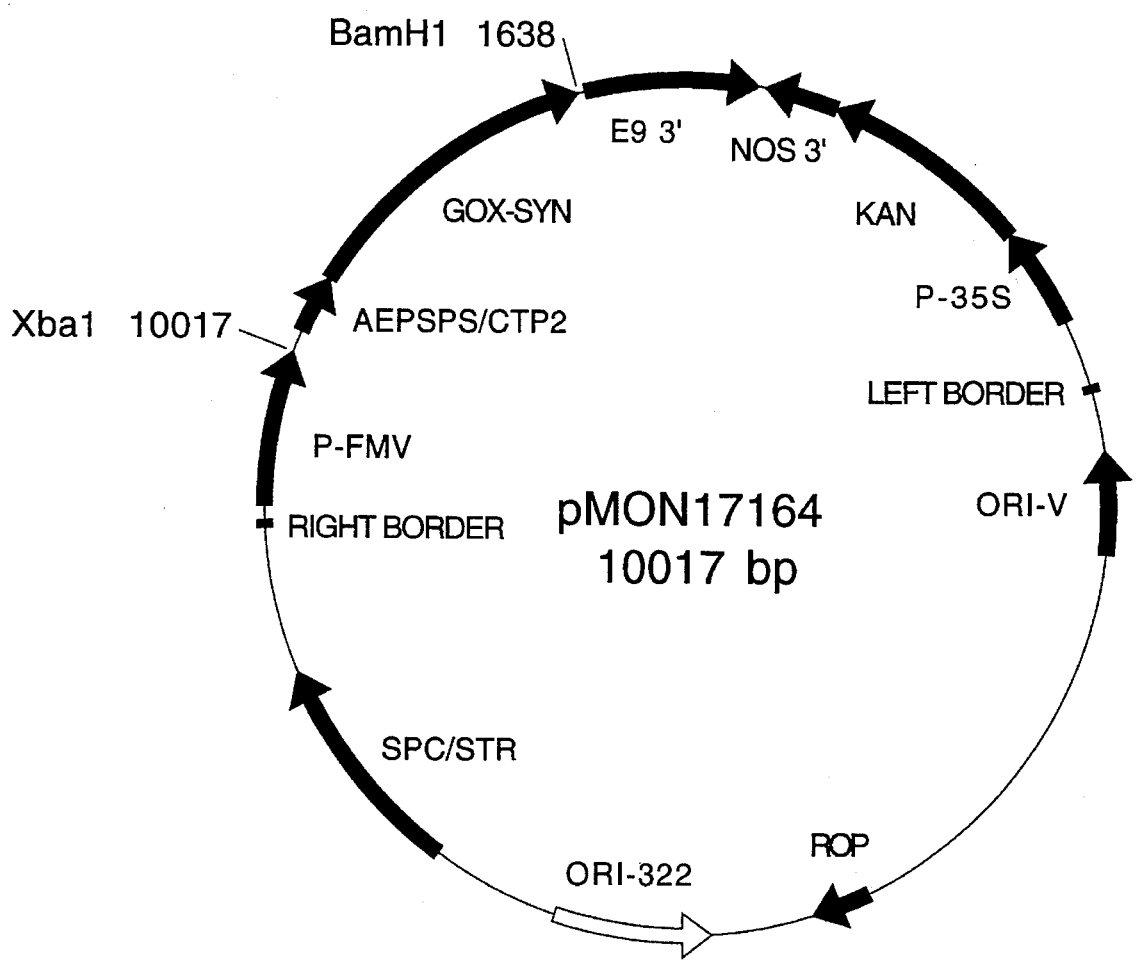
FIG. 12 shows the structural map of plasmid pMON17164.

In the second example, a CTP-glyphosate oxidoreductase fusion was constructed between the *Arabidopsis thaliana* EPSPS (Klee et al., 1987) CTP and the synthetic glyphosate oxidoreductase coding sequences. The Arabidopsis CTP was first engineered by site-directed mutagenesis to place a SphI restriction site at the CTP processing site. This mutagenesis replaced the Glu-Lys at this location with Cys-Met. The sequence of this CTP, designated CTP2, (SEQ ID NO:10) is shown in FIG. 9. The NcoI site of the synthetic glyphosate oxidoreductase gene (SEQ ID NO:8) was replaced with a SphI site that spans the Met codon. The second codon was converted to one for leucine in this step also. This change had no apparent effect on the in vivo activity of glyphosate oxidoreductase in *E. coli*. The CTP2-synthetic glyphosate oxidoreductase fusion was cloned into pBlueScript KS(+) and this template was transcribed in vitro using T7 polymerase and the $^{35}$S-methionine-labeled material was shown to import into chloroplasts with an efficiency comparable to that for the CTP1-glyphosate oxidoreductase fusion. This CTP2-synthetic glyphosate oxidoreductase fusion was then cloned as a XbaI-BamHI fragment into a plant expression vector to form pMON17164. A structural map of this plasmid is presented in FIG. 12.

The plant vector portion of pMON17164 (FIG. 12) is composed of the following segments. A chimeric kanamycin resistance gene engineered for plant expression to allow selection of the transformed tissue. The chimeric gene consists of the 0.35 Kb cauliflower mosaic virus 35S promoter (P-35S) (Odell et al., 1985), the 0.83 Kb neomycin phosphotransferase typeII gene (KAN), and the 0.26Kb 3'-non-translated region of the nopalinee synthase gene (NOS 3') (Fraley et al., 1983). A 0.45 Kb ClaI to DraI fragment from the pTi15955 octopine Ti plasmid, which contains the T-DNA left border region (Barker et al., 1983) A 0.75 Kb segment containing the origin of replication from the RK2 plasmid (ori-V) (Stalker et al., 1981) A 3.0 Kb SalI to PstI segment of pBR322 which provides the origin of replication for maintenance in *E. coli* (ori-322) and the bom site for the conjugational transfer into *Agrobacterium tumefaciens* cells. A 0.93 Kb fragment isolated from transposon Tn7 which encodes bacterial spectinomycin/streptomycin resistance (Spc/Str) (Fling et al., 1985), and is a determinant for selection in *E. coli* and *Agrobacterium tumefaciens*. A 0.36 Kb PvuI to BclI fragment from the pTiT37 plasmid, which contains the nopaline-type T-DNA right border region (Fraley et al., 1985). An expression cassette consisting of the 0.6 Kb 35S promotor from the figwort mosaic virus (P-FMV) (Gowda et al., 1989), several unique cloning sites, and the 0.7 Kb 3' nontranslated region of the pea rbcS-E9 gene (E9 3') (Coruzzi et al., 1984, and Morelli et al., 1985). The CTP2-synthetic glyphosate oxidoreductase fusion fragment was cloned into this expression cassette. The introduction of this plasmid into Agrobacterium and subsequent plant transformation is described in the Examples to follow.

Those skilled in the art will recognize that various chimeric constructs can be made which utilize the functionality of a particular CTP to import the contiguous glyphosate oxidoreductase enzyme into the plant cell chloroplast. The chloroplast import of the glyphosate oxidoreductase can be determined using the following assay.

Chloroplast Uptake Assay

Intact chloroplasts are isolated from lettuce (*Latuca sativa*, var. longifolia) by centrifugation in Percoll/ficoll gradients as modified from Bartlett et al. (1982). The final pellet of intact chloroplasts is suspended in 0.5 ml of sterile 330 mM sorbitol in 50 mM Hepes-KOH, pH 7.7, assayed for chlorophyll (Arnon, 1949), and adjusted to the final chlorophyll concentration of 4 mg/ml (using sorbitol/Hepes). The yield of intact chloroplasts from a single head of lettuce is 3–6 mg chlorophyll.

A typical 300 µl uptake experiment contained 5 mM ATP, 8.3 mM unlabeled methionine, 322 mM sorbitol, 58.3 mM Hepes-KOH (pH 8.0), 50 µl reticulocyte lysate translation products, and intact chloroplasts from *L. sativa* (200 µg chlorophyll). The uptake mixture is gently rocked at room temperature (in 10×75 mm glass tubes) directly in front of a fiber optic illuminator set at maximum light intensity (150 Watt bulb). Aliquot samples of the uptake mix (about 50 μl) are removed at various times and fractionated over 100 μl silicone-oil gradients (in 150 μl polyethylene tubes) by centrifugation at 11,000 X g for 30 seconds. Under these conditions, the intact chloroplasts form a pellet under the silicone-oil layer and the incubation medium (containing the reticulocyte lysate) floats on the surface. After centrifugation, the silicone-oil gradients are immediately frozen in dry ice. The chloroplast pellet is then resuspended in 50–100 μl of lysis buffer (10 mM Hepes-KOH pH 7.5, 1 mM PMSF, 1 mM benzamidine, 5 mM ε-amino-n-caproic acid, and 30 μg/ml aprotinin) and centrifuged at 15,000 X g for 20 minutes to pellet the thylakoid membranes. The clear supernatant (stromal proteins) from this spin, and an aliquot of the reticulocyte lysate incubation medium from each uptake experiment, are mixed with an equal volume of 2X SDS-PAGE sample buffer for electrophoresis (see below).

SDS-PAGE is carded out according to Laemmli (1970) in 3–17% (w/v) acrylamide slab gels (60 mm X 1.5 mm) with 3% (w/v) acrylamide stacking gels (5 mm X 1.5 mm). The gel is fixed for 20–30 minutes in a solution with 40% methanol and 10% acetic acid. Then, the gel is soaked in EN³HANCE™ (DuPont) for 20–30 minutes, followed by drying the gel on a gel dryer. The gel is imaged by autoradiography, using an intensifying screen and an overnight exposure to determine whether the glyphosate oxidoreductase is imported into the isolated chloroplasts.

Alternative Isolation Protocol for Other Glyphosate Oxidoreductase Structural Genes A number of other glyphosate oxidoreductase genes have been identified and cloned, including the second LBAA glyphosate oxidoreductase gene from the Class II cosmid pMON7477. The gene was located, by Southern hybridization, on the ~23 kb HindIII fragment, discussed in the cloning section above, using the first glyphosate oxidoreductase gene as a probe. Southern analysis also showed PstI and BglII hybridizing bands of ~3.5 and ~2.5 kb, respectively. The BglII fragment from pMON7477 was subcloned into the BamHI site of pBlueScript vector. A clone in *E. coli* JM101 (pMON7482), in which the cloned fragment was oriented relative to the lac promoter as in pMON7469#1, was induced with IPTG and assayed for glyphosate oxidoreductase activity. In this experiment a Sp. Act. of ~93 nmol/min.mg was obtained. In a later experiment, Class I and Class II cosmids were also isolated following infection of *E. coli* JM101 with the same packaged cosmid preparation and selection directly for glyphosate tolerance at 3–5 mM glyphosate on M9 media.

Figure 13:
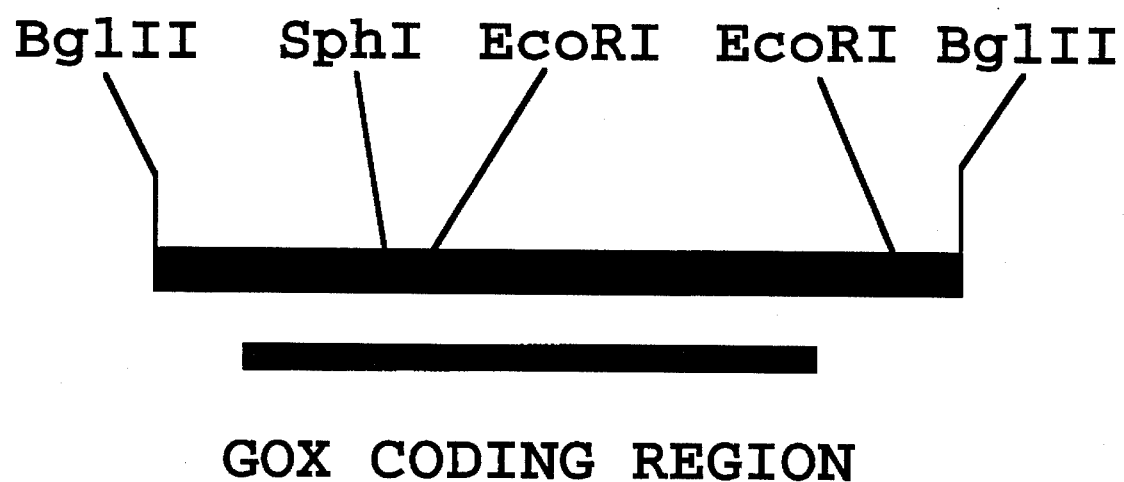
FIG. 13 illustrates restriction sites of the GOX coding region.

A glyphosate oxidoreductase gene has also been subcloned from another microbial isolate, identified originally by its ability to utilize glyphosate as a phosphorous source and later shown to contain a putative glyphosate oxidoreductase gene by hybridization with the LBAA glyphosate oxidoreductase gene probe. This gene was cloned initially in a T7 promoter cosmid by screening for glyphosate tolerance in *E. coli* HB101/pGP1-2 (Boyer and Rolland-Dussoix, 1969; Tabor and Richardson, 1985) on M9 medium containing glyphosate at 3 mM. The presence of the glyphosate oxidoreductase gene was first indicated by a positive hybridization signal with the LBAA gene and by its location on a 2.5 kb BglII fragment. This BglII fragment was cloned into the BamHI site in pBlueScript (pMON17183) and expressed from the lac promoter by addition of IPTG. In this experiment a glyphosate oxidoreductase with a specific activity of 53 nmoles/min.mg was obtained, confirming the isolation of the gene by this strategy. The following features have usually been found for these glyphosate oxidoreductase genes: the genes are found (by Southern hybridization using full-length glyphosate oxidoreductase gene probes) on ~2.5 kb BglII fragments, on ~3.5 PstI fragments, contain one EcoRI site within the gene and the genes do not contain a HindIII site. The schematic diagram of FIG. 13 illustrates some common features of these genes.

The high degree of similarity of glyphosate oxidoreductase genes also suggests another way by which new glyphosate oxidoreductase genes may be cloned. The apparent conservation of regions flanking the genes and the absence of certain restriction sites suggests the use of single-stranded oligonucleotide probes to the flanking regions, containing restriction sites for BglII, HindIII, PstI, BamHI, NdeI, or other suitable cloning sites, and PCR (Polymerase Chain Reaction; see Erlich, 1989, for complete details on PCR and its applications) to amplify a glyphosate oxidoreductase gene fragment suitable for cloning. The flanking sequences for 119 bp upstream (SEQ ID NO:11) of the wild-type (LBAA isolate) glyphosate oxidoreductase gene and for ~290 bp (SEQ ID NO:12) downstream of the gene are provided in FIG. 2.

Using this PCR approach, glyphosate oxidoreductase genes from a number of sources have been isolated. The presence of the glyphosate oxidoreductase activity was confirmed by cloning the glyphosate oxidoreductase gene from chromosomal DNA prepared from *Pseudomonas sp.* strain LBr (Jacob et al., 1988) and using primers homologous to the N- and C-termini of the LBAA glyphosate oxidoreductase gene and containing the following suitable restriction cloning sites: 5'-GAGAGACTGT CGACTC-CGCG GGAGCATCAT ATG-3' (SEQ ID NO:13) and 5'-GAACGAATCC AAGCTTCTCA CGACCGCGTA AGTAC-3' (SEQ ID NO:14). Cyclotherm parameters used for these PCR reactions is as follows:

Denature at 94° C. for 1 minute;

Anneal at 60° C. for 2 minutes;

Polymerize at 72° C. for 3 minutes, 30 cycles, no autoextension, linked to 4° C. incubation. The expected ~1.3 kb PCR produced was generated and following digestion with NdeI and HindIII, this fragment was cloned into pMON2123 for expression of the encoded enzyme. The glyphosate oxidoreductase activity was measured as described above and the $K_m$ for glyphosate was similar to that for enzymes from LBAA which is presented supra.

| source of glyphosate oxidoreductase gene | $K_m$ (glyphosate; mM) |
| --- | --- |
| Pseudomonas sp. strain LBr | 25 |

Bacteria isolated from glyphosate process waste stream treatment facilities may also be capable of converting glyphosate to AMPA. Pseudomonas strains LBAA and LBr are two such examples. Such bacteria may also be isolated de novo from these waste treatment facilities.

A population of bacteria was isolated from a fixed-bed immobilized cell column, which employed Mannville R-635 diatomaceous earth beads, by plating on Tryptone Soy Agar (Difco), containing cycloheximide at 100 ug/ml, and incubating at 28° C. The column had been run for three months on a wastewater feed from the Monsanto Company's Luling, Miss., glyphosate production plant. The column contained 50 mg/ml glyphosate and $NH_3$ as $NH_4Cl$. Total organic carbon was 300 mg/ml and BOD's (Biological Oxygen Demand—a measure of "soft" carbon availability) was less than 30 mg/ml. This treatment column has been described (Heitkamp et al., 1990). One of the predominant members of this population, identified as *Agrobacterium sp*. strain T10, was found to also grow in minimal broth in which the sole carbon source provided was glyphosate at 10 mM (this broth was made up as for DF medium but with glyphosate substituting for the glucose, gluconate and citrate). Chromosomal DNA was prepared from this isolate and subjected to the same PCR procedure and with the same primers as described above for the strain LBr. A fragment of the correct size was generated and cloned into the *E. coli* expression vector. The glyphosate oxidoreductase activity was assayed and the $K_m$ for glyphosate also determined:

| source of gene | $K_m$ (glyphosate; mM) |
| --- | --- |
| Agrobacterium sp. strain T10 | 28 |

Glyphosate-to-AMPA conversion has been reported for many different soils (see Malik et al., 1989 for a review) and a number of procedures are available for the extraction of total DNA from mixed environment samples such as soil (Holben et al., 1988; Steffan and Atlas, 1988; Tsai and Olson, 1991), indicating the possibility of cloning glyphosate oxidoreductase genes without having to first isolate such a degrading microorganism. Of course, the procedure described for the cloning of the glyphosate oxidoreductase genes, based on the conferring of a glyphosate utilization ability or glyphosate tolerance on *E. coli*, provides a scheme by which other glyphosate oxidoreductase genes and other glyphosate metabolizing genes may be cloned, without relying on the homology determined for the glyphosate oxidoreductase gene described here. It is possible also to enrich for glyphosate degrading bacteria, for example, by the repeated application of glyphosate to a patch of soil (Quinn et al., 1988, Talbot et al., 1984). This enrichment step might be used to increase the ease with which glyphosate oxidoreductase genes are recovered from soil or other environments.

Evidence for the presence of the glyphosate oxidoreductase gene in soil bacteria and a procedure for the isolation of such genes is outlined in the following: A population of suitable bacteria was enriched for selection of bacteria capable of growing in liquid media with glyphosate (at 10 mM) as a source of carbon (This medium is made up as described for the Dworkin-Foster medium but with the omission of the carbon sources and with Pi as a source of P). The inoculum was provided by extracting soil (from a recently harvested soybean field in Jerseyville, Ill.) and the population selected by successive culturing in the medium described above at 28° C. (cycloheximide was included at 100 μg/ml to prevent growth of fungi). Upon plating on L-agar medium, 5 colony types were identified. Chromosomal DNA was prepared from 2 ml L-broth cultures of these isolates and the presence of the glyphosate oxidoreductase gene was probed using PCR screening. Using the primers GCCGAGATGACCGTGGCCGAAAGC (SEQ ID NO:15) and GGGAATGCCGGATGCTTCAACGGC (SEQ ID NO:16 ), a DNA fragment of the predicted size was obtained with the chromosomal DNA from one of the isolates (designated S3). The PCR conditions used were as follows: 1 minute at 94° C.; 2 minutes at 40° C.; 3 minutes at 72° C.; 35 cycles. The DNA fragment generated in this way is used as a probe (following radiolabeling) to isolate the S3 glyphosate oxidoreductase gene candidate from a cosmid bank constructed as described for LBAA DNA and greatly facilitates the isolation of other glyphosate oxidoreductase genes. The primers used are homologous to internal sequences in the LBAA glyphosate oxidoreductase gene. The PCR conditions employed allow a fair degree of mismatch in the primers and the result suggests that the glyphosate oxidoreductase gene from S3 may not be as closely related to the other glyphosate oxidoreductase genes that were successfully isolated using the primers to the N- and C-termini of the LBAA gene.

A variety of procedures are available for the isolation of genes. Some of these procedures are based on the knowledge of gene function that allow the design of phenotypic screens to aid in the isolation. Others are based on at least partial DNA sequence information that allow the use of probes or primers with partial or complete homology, or are based on the use of antibodies that detect the gene product. All of these options may be applied to the cloning of glyphosate oxidoreductase genes.

Improvement of the Kinetic Properties of Glyphosate Oxidoreductase

Prior examples of engineered herbicide resistance by enzymatic inactivation of the herbicide have utilized enzymes with an ability to bind and metabolize the herbicides much more efficiently than glyphosate oxidoreductase metabolizes glyphosate. The glyphosate oxidoreductase enzyme has a $K_m$ for glyphosate of 20–30 mM and, as a result, the reaction rate for the degradation of glyphosate may be enhanced for optimal efficiency in transgenic plants by either lowering the $K_m$ or by raising the $V_{max}$.

Random mutagenesis techniques coupled with appropriate selections and/or screens are powerful tools which have been used successfully to generate large numbers of mutagenized gene sequences and potential variants. The same approaches may be used to isolate and to identify glyphosate oxidoreductase variants with improved glyphosate degradation efficiency. The mutagenesis techniques that may be employed include chemical mutagenesis of bacterial cultures containing the gene of interest or of purified DNA containing this gene and PCR methods used to generate copies of the gene (or portions of it) under conditions that favor misincorporation of nucleotides (errors) into the new strand. An example of such a condition would be carrying out the PCR reaction in the presence of Mn++.

Appropriate in vivo screens for improved variants following the mutagenesis could include those for improved glyphosate tolerance in *E. coli* or increased growth on glyphosate in Mpu+ strains. For the screen, the glyphosate oxidoreductase gene is cloned into a vector containing a weak bacterial promoter and/or in a replicon with a low copy number. The glyphosate tolerance phenotypes of different glyphosate oxidoreductase constructs have been shown to vary over a range of glyphosate concentrations and to correlate with the level of glyphosate oxidoreductase expression. For example, under uninduced conditions, Plac-glyphosate oxidoreductase vectors express less glyphosate oxidoreductase than PrecA-glyphosate oxidoreductase vectors and also display lower glyphosate tolerance. The mutagenized gene fragment is cloned into the most suitable vector and the resultant library screened. Variants are selected for their ability to grow at glyphosate levels which inhibit growth of the control strain containing the parent glyphosate oxidoreductase clone. Glyphosate oxidoreductase activity confers on *E. coli* the ability to convert glyphosate to AMPA and, in suitable *E. coli* strains, this AMPA can provide a source of phosphate following cleavage of the C-P bond by C-P lyase. Suitable *E. coli* strains are B strains or Mpu+ derivatives of K strains. The glyphosate oxidoreductase gene confers minimal growth on glyphosate as the sole phosphorus source in strain *E. coli* JM101 Mpu+ (=GB993). The growth rate on glyphosate has been shown to also correlate with the glyphosate oxidoreductase expression level. The mutagenized glyphosate oxidoreductase gene is cloned into the appropriate vector and the variant library screened by differential growth rates on plates or by culturing in media containing glyphosate as sole phosphorous source. Clones which demonstrate faster growth on plates relative to the control strain are subsequently re-screened by growth curve analysis.

Glyphosate oxidoreductase variants which have been identified in each selection/screen are cloned into a vector for high-level expression and subjected to enzyme analysis to determine $K_m$ and $V_{max}$ values for glyphosate. The best glyphosate oxidoreductase variants are purified for complete kinetic characterization. Glyphosate oxidoreductase variants which have been identified with lower $K_m$ values and similar or higher $V_{max}$ values than wild-type enzyme values are analyzed by nucleic acid sequencing to determine the mutation(s). The goal in isolating variants would be to increase the $k_{cat}/K_m$ ratio for glyphosate oxidoreductase-catalyzed glyphosate degradation.

A variant with such improvements was isolated. The mutagenesis procedure used was that of Mn++-poisoned PCR and the template was a linearized glyphosate oxidoreductase gene plasmid containing the synthetic glyphosate oxidoreductase gene (SEQ ID NO:8). The oligonucleotide primers used were homologous to regions in the vector and flanking the glyphosate oxidoreductase gene. The PCR conditions employed were as follows: 1 minute at 94° C., 2 minutes at 55° C., and 3 minutes at 72° C. and with 35 cycles. A 5:1 ratio of dCTP+dGTP+TTP to dATP was used. The reactions contained $MnCl_2$ at 125, 250, 375, or 500 µM. After the reaction, the amplified product was recloned into a vector containing a weak *E. coli* promoter. This vector was a pBR327 derivative containing the araBAD promoter and suitable cloning sites. One hundred colonies from this cloning step were then screened in *E. coli* GB993 for improved glyphosate tolerance and utilization phenotypes in media composed of MOPS minimal medium with glyphosate and Pi or with glyphosate alone, respectively. Growth rates were determined by measuring $A_{550}$ over a 96 hour period. Three clones were identified that exhibited faster growth rates in these screens. These transformants had a 1.5–2.0-fold faster utilization phenotype. The glyphosate oxidoreductase gene was recloned into the expression vector portion and this phenotype verified. All kinetic analysis was performed on crude *E. coli* lysates. Putative glyphosate oxidoreductase variant proteins were overexpressed after subcloning the NcoI/HindIII variant glyphosate oxidoreductase gene into PrecA-gene10L expression vector. For overexpression in PrecA-gene10L constructs, GB993 cells containing the vector were induced at a Klett=110–120 in M9 minimal medium with 50 µg/ml nalidixic acid and allowed to grow for 2.5 hours at 37° C. with vigorous shaking. Cells were harvested by centrifugation at 4000 g, 5 minutes at 4° C., and resuspend in 100 mM Tris-HCl, pH 7.1, 1 mM EDTA, 35 mM KCl, 20% glycerol, and 1 mM benzamidine at 3 ml/g cell pellet. Lysates were prepared by breaking the cells in a French press, twice, at 1000 psi. Insoluble debris was removed by centrifugation at 12000 g, 15 minutes at 4° C., and the supernatant was de-salted by passing over a PD-10 column (Sephadex G-25, Pharmacia). The void volume fraction was used as the source of enzyme for kinetic analysis. Protein concentrations were determined using the Bio-Rad protein dye-binding assay. Time and enzyme concentration courses were performed to determine linear ranges. The enzyme assay was performed as follows: lysate and glyphosate oxidoreductase mix (final concentration= 0.1M MOPS, 0.01M Tricine, pH 7.4, 0.01 mM FAD, 10 mM $MgCl_2$) in a 100 µl reaction were preincubated at 30° C. for 2 minutes prior to the addition of glyphosate (analytical grade stock prepared in water adjusted to pH 7.0 with NaOH). Ten minutes was determined to be the optimal time for the enzyme assay using 10 µg lysate. After 10 minutes at 30° C. with shaking, 0.25 ml dinitophenylhydrazine (DNPH) reagent (0.5 mg/ml in 0.5M HCl) was added and the reaction was allowed to proceed for an additional 5 minutes at 30° C. with shaking. A 1.5M NaOH solution (400 µl) was then added to the assay mix, and the reaction was continued for 5 minutes at 30° C. with shaking. Enzyme activity was determined from the amount of glyoxylate-DNPH adduct formed by measuring $A_{520}$ against a standard of glyoxylate. Enzyme assays are performed in duplicate on at least two different single colony isolates of a putative glyphosate oxidoreductase variant. To determine $K_m$ and $V_{max}$, enzyme assays were performed over a $(0.2–2.0) \times K_m$ range of glyphosate concentrations. The $K_m$ and $V_{max}$ were determined from Lineweaver Burk, Eadie-Hofstee and hyperbolic kinetic plots. $V_{max}$ was estimated after determining the amount of immunoreactive glyphosate oxidoreductase protein in lysates by immunoblot analysis as described below. Immunoblot analysis was performed following SDS-PAGE and transfer of protein from the gel to nitrocellulose at 500 mA in a Hoeffer transfer apparatus in 25 mM Tris-HCl, 192 mM glycine containing 0.1% SDS and 25% methanol for 1–2 hours. After transfer, the nitrocellulose was incubated with 50 mM Tris-HCl, pH7.5, 0.9% NaCl, 0.01% Tween 20, 0.02% $NaN_3$ containing 2% bovine serum albumin at room temperature with shaking for at least 30 minutes. After blocking, the same buffer containing a 1:25, 000 dilution of goat anti-glyphosate oxidoreductase antiserum was added and the filter was allowed to shake at room temperature for 45 minutes. After incubation with primary glyphosate oxidoreductase antibody, the filter was washed for 45 glyphosate oxidoreductase minutes in buffer without antibody; buffer containing a 1:5000 dilution of rabbit anti-goat alkaline phosphatase-conjugated second antibody (from Pierce) was added and the filter was incubated for 45 minutes at room temperature with shaking. The filter was then washed in buffer without antibody for 30 minutes prior to addition of NBT and BCIP (Promega) to allow color development. Immunoreactive glyphosate oxidoreductase protein was also quantitated by dot blotting the lysate onto nitrocellulose and then processing the filter as described above, except that $^{125}$I-Protein G was used for detection. The amount of glyphosate oxidoreductase protein in lysates was determined by counting the dot and comparing the amount of radioactivity against a glyphosate oxidoreductase protein standard. One variant, v.247, showed a 3–4-fold higher specific activity for glyphosate oxidoreductase at 25 mM glyphosate and the immunoblot analysis indicated that this was not due to an elevated glyphosate oxidoreductase protein level. Subsequent assays indicated that this variant had a 10-fold lower $K_m$ for glyphosate than the wild type glyphosate oxidoreductase. In a similar manner the $K_m$ for IDA was also determined and these data are presented below.

| Kinetic analysis of glyphosate oxidoreductase variants: | | | | | |
|---|---|---|---|---|---|
| | app $K_m$ (mM) | | app $V_m$ (U/mg) | | $V_m/K_m$ |
| Variant | Glyp | IDA | Glyp | IDA | Glyp | IDA |
| wild type | 27.0 | 2.8 | 0.8 | 0.5 | .03 | .18 |
| v.247 | 2.6 | 0.7 | 0.6 | 0.7 | .23 | 1.0 |

The glyphosate oxidoreductase gene from v.247 was sequenced (SEQ ID NO:17) and five nucleotide changes were found. These changes are described in the following as they relate to the codons: GCT to GCC (codon 43), no amino acid change; AGC to GGC (codon 84), Ser to Gly; AAG to AGG (codon 153), Lys to Arg; CAC to CGC (codon 334), His to Arg, and CCA to CCG (codon 362), no amino acid change. The amino acid sequence of the glyphosate oxidoreductase gene from v.247 is presented as SEQ ID NO:18. The importance of these different amino acid changes was determined initially by recloning the altered regions into wild type glyphosate oxidoreductase and determining the effect on glyphosate oxidoreductase activity and kinetics. This was accomplished by recloning the NcoI-NheI fragment (contains codon 84), the NheI-ApaLI fragment (contains codon 153), and the ApaLI-HindIII fragment (contains codon 334), seperately into the wild type gene. These glyphosate oxidoreductase genes were then expressed and the kinetic analyses performed. The data are presented below and indicate that the change that occured in the ApaLI-HindIII fragment (contains codon 334) was responsible solely for the alteration in the enzyme.

| Kinetic analysis of domain switches | | | |
|---|---|---|---|
| Clone | app $K_m$ (mM) | app $V_m$ (U/mg) | $V_m/K_m$ |
| wt (w1w2w3*) | 28.4 | 0.65 | 0.022 |
| v.247(v1v2v3**) | 2.1 | 0.72 | 0.34 |
| w1v2w3 | 23.5 | 0.62 | 0.026 |
| w1v2v3 | 2.1 | 0.6 | 0.28 |
| w1w2v3 | 2.0 | 0.75 | 0.375 |
| v1w2v3 | 2.6 | 0.55 | 0.21 |
| v1w2w3 | 28.0 | 0.75 | 0.027 |
| v1v2w3 | 26.7 | 0.55 | 0.021 |

*w1 = SER84; w2 = LYS153; w3 = HIS334?
**v1 = GLY84; v2 = ARG153; v3 = ARG334

This result was confirmed and extended by repeating the His to Arg change at codon 334 and introducing other specific changes at this residue by site-directed mutageneses. The primers are listed in the following: Arg—CGTTCTCTAC ACTCGTGCTC GTAAGTTGC (SEQ ID NO:19); Lys—CGTTCTCTAC ACTAAGGCTC GTAAGTTGC (SEQ ID NO:20); Gln—CGTTCTCTAC ACTCAAGCTC GTAAGTTGC (SEQ ID NO:21); and Ala—CGTTCTCTAC ACTGCTGCTC GTAAGTTGC (SEQ ID NO:22) (These sequences are the antisense to those actually used). The presence of these changes was confirmed by sequencing the mutagenized glyphosate oxidoreductase genes and a kinetic analysis of the expressed glyphosate oxidoreductase enzymes was performed. The data are presented in the following and show that a number of substitutions are possible at this position and which result in an enzyme with altered kinetic properties.

| Kinetic analysis of glyphosate oxidoreductase variants: | | | | | |
|---|---|---|---|---|---|
| | app $K_m$ (mM) | | app $V_m$ (U/mg) | | $V_m/K_m$ |
| Variant | Glyp | IDA | Glyp | IDA | Glyp | IDA |
| wild type | 27.0 | 2.8 | 0.8 | 0.5 | .03 | .18 |
| v.247 | 2.6 | 0.7 | 0.6 | 0.7 | .23 | 1.0 |
| ARG 334 | 2.6 | 0.5 | 0.6 | 0.6 | .23 | 1.2 |
| LYS 334 | 9.9 | 1.3 | 0.7 | 0.8 | .07 | .62 |
| GLN 334 | 19.6 | 3.5 | 0.6 | 0.7 | .03 | .20 |
| ALA 334 | 26.7 | 3.5 | 0.2 | 0.2 | .007 | .057 |

Additonal mutageneses were performed to change the His334 residue to other amino acids. The primers to accomplish this and the new codon are listed in the following: Trp—CTCTACACTTGGGCTCGTAAGCTTCTTCCAGC (SEQ ID NO:23); Ile—CTCTACACTATCGCTCG-TAAGCTTCCAGC (SEQ ID NO:24); Leu—CTCTA-CACTCTGGCTCGTAAGCTTCTTCCAGC (SEQ ID NO:25); and Glu—CTCTACACTGAAGCTCGTAAGCT-TCTTCCAGC (SEQ ID NO:26) (These sequences are the antisense of those actually used; these primers also add a "silent" HindIII that facilitates the identification of the mutagenized progeny from the population). The GLU334 variant retains substantial glyphosate oxidoreductase activity, while TRP334, ILE334, and LEU334 variants retain much less activity.

From the first generation variants, those with the highest $k_{cat}/K_m$ ratio are preferably subjected to a second round of mutagenesis followed by subsequent screening and analysis. An alternative approach would be to construct second generation glyphosate oxidoreductase variants by combining single point mutations identified in the first generation variants.

PLANT TRANSFORMATION

Plants which can be made glyphosate tolerant by practice of the present invention include, but are not limited to, soybean, cotton, corn, canola, oil seed rape, flax, sugarbeet, sunflower, potato, tobacco, tomato, wheat, rice, alfalfa, lettuce, apple, poplar and pine.

A double-stranded DNA molecule of the present invention ("chimeric gene") can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1984), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

The pMON979 plant transformation/expression vector was derived from pMON886 (described below) by replacing the neomycin phosphotransferase typeII (KAN) gene in pMON886 with the 0.89 kb fragment containing the bacterial gentamicin-3-N-acetyltransferase type III (AAC(3)-III) gene (Hayford et al., 1988). The chimeric P-35S/AA(3)-III/

NOS 3' gene encodes gentamicin resistance which permits selection of transformed plant cells. pMON979 also contains a 0.95 kb expression cassette consisting of the enhanced CaMV 35S promoter (Kay et al., 1987), several unique restriction sites, and the NOS 3' end (P-En-CaMV35S/NOS 3'). The rest of the pMON979 DNA segments are exactly the same as in pMON886.

Plasmid pMON886 is made up of the following segments of DNA. The first is a 0.93 kb AvaI to engineered-EcoRV fragment isolated from transposon Tn7 that encodes bacterial spectinomycin/streptomycin resistance (Spc/Str), which is a determinant for selection in *E. coli* and *Agrobacterium tumefaciens*. This is joined to the 1.61 kb segment of DNA encoding a chimeric kanamycin resistance which permits selection of transformed plant cells. The chimetic gene (P-35S/KAN/NOS 3') consists of the cauliflower mosaic virus (CaMV) 35S promoter, the neomycin phosphotransferase typeII (KAN) gene, and the 3'-nontranslated region of the nopaline synthase gene (NOS 3') (Fraley et al., 1983). The next segment is the 0.75 kb oriV containing the origin of replication from the RK2 plasmid. It is joined to the 3.1 kb SalI to PvuI segment of pBR322 (ori322) which provides the origin of replication for maintenance in *E. coli* and the bom site for the conjugational transfer into the *Agrobacterium tumefaciens* cells. The next segment is the 0.36 kb PvuI to BclI from pTiT37 that carries the nopaline-type T-DNA right border (Fraley et al., 1985).

The pMON981 plasmid contains the following DNA segments: the 0.93 kb fragment isolated from transposon Tn7 encoding bacterial spectinomycin/streptomycin resistance [Spc/Str; a determinant for selection in *E. coli* and *Agrobacterium tumefaciens* (Fling et al., 1985)]; the chimeric kanamycin resistance gene engineered for plant expression to allow selection of the transformed tissue, consisting of the 0.35 kb cauliflower mosaic virus 35S promoter (P-35S) (Odell et al., 1985), the 0.83 kb neomycin phosphotransferase typeII gene (KAN), and the 0.26 kb 3'-nontranslated region of the nopaline synthase gene (NOS 3') (Fraley et al., 1983); the 0.75 kb origin of replication from the RK2 plasmid (oriV) (Stalker et al., 1981); the 3.1 kb SalI to PvuI segment of pBR322 which provides the origin of replication for maintenance in *E. coli* (ori-322) and the bom site for the conjugational transfer into the *Agrobacterium tumefaciens* cells, and the 0.36 kb PvuI to BclI fragment from the pTiT37 plasmid containing the hopaline-type T-DNA right border region (Fraley et al., 1985). The expression cassette consists of the 0.6 kb 35S promoter from the figwort mosaic virus (P-FMV) (Gowda et al., 1989) and the 0.7 kb 3' nontranslated region of the pea rbcS-E9 gene (E9 3') (Coruzzi et al., 1984, and Morelli et al., 1985). The 0.6 kb SspI fragment containing the FMV35S promoter (FIG. 1) was engineered to place suitable cloning sites downstream of the transcriptional start site.

The plant vector was mobilized into the ABI Agrobacterium strain. The ABI strain is the A208 *Agrobacterium tumefaciens* carrying the disarmed Ti plasmid pTiC58 (pMP90RK) (Koncz and Schell, 1986). The Ti plasmid does not carry the T-DNA phytohormone genes and the strain is therefore unable to cause the crown gall disease. Mating of the plant vector into ABI was done by the triparental conjugation system using the helper plasmid pRK2013 (Ditta et al., 1980). When the plant tissue is incubated with the ABI::plant vector conjugate, the vector is transferred to the plant cells by the vir functions encoded by the disarmed pTiC58 plasmid. The vector opens at the T-DNA right border region, and the entire plant vector sequence may be inserted into the host plant chromosome. The pTiC58 Ti plasmid does not transfer to the plant cells but remains in the Agrobacterium.

PLANT REGENERATION

When adequate production of the glyphosate oxidoreductase activity is achieved in transformed cells (or protoplasts), the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops. See, e.g., Ammirato, 1984; Shimamoto, 1989; Fromm, 1990; Vasil, 1990.

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

EXAMPLES

Expression, Activity and Phenotype of Glyphosate Oxidoreductase in Transformed Plants The transformation, expression and activity of glyphosate oxidoreductase, and the glyphosate tolerance phenotype imparted to the plants by the glyphosate oxidoreductase genes, introduced into *Nicotiana tabacum* cv. "Samsun" and/or *Brassica napus* cv. Westar using the vectors pMON17073, pMON17032, pMON17065, pMON17066, pMON17138, and pMON17164, is described in the following exemplary embodiments. Initial data in tobacco on the expression of the manipulated glyphosate oxidoreductase gene (SEQ ID NO:6) under the control of the En-CaMV35S promoter (see data on pMON17073 in Tables VIII and IX, for example) indicated only low levels of expression of glyphosate oxidoreductase. The transcription of the gene was confirmed in the case of 3–4 plants by Northern and S1 analysis but no glyphosate oxidoreductase protein could be detected (limit of detection in that assay was ~0.01% expression level). Analysis of $R_o$ plants following spray with 0.4 lb/acre (approximately 0.448 kg/ha) glyphosate also showed only low levels of tolerance. Modification of the gene sequence (as described herein) resulted in improved expression in tobacco, as did the use of the FMV promoter and the use of a CTP fusion to the glyphosate oxidoreductase gene. For these reasons the majority of the data presented comes from transgenic plants derived using vectors containing these improved glyphosate oxidoreductase constructs. One set of experiments with the modified glyphosate oxidoreductase vector pMON17032 are presented in example 1 and a study of manipulated glyphosate oxidoreductase, synthetic glyphosate oxidoreductase, and CTP1-synthetic glyphosate oxidoreductase is presented in example 2. The transformation and expression of glyphosate oxidoreductase in canola is described in example 3.

EXAMPLE 1

The tobacco leaf disc transformation protocol employs healthy leaf tissue about 1 month old. After a 15–20 minute surface sterilization with 10% Clorox plus a surfactant, the leaves were rinsed 3 times in sterile water. Using a sterile paper punch, leaf discs are punched and placed upside down on MS104 media (MS salts 4.3 g/l, sucrose 30 g/l, B5 vitamins 500X 2 ml/l, NAA 0.1 mg/l, and BA 1.0 mg/l) for a 1 day preculture.

The discs were then inoculated with an overnight culture of disarmed Agrobacterium ABI containing the subject vector that had been diluted ⅕ (ie: about 0.6 OD). The inoculation was done by placing the discs in centrifuge tubes with the culture. After 30 to 60 seconds, the liquid was drained off and the discs were blotted between sterile filter paper. The discs were then placed upside down on MS104 feeder plates with a filter disc to co-culture.

After 2-3 days of co-culture, the discs were transferred, still upside down, to selection plates with MS104 media. After 2-3 weeks, callus formed, and individual clumps were separated from the leaf discs. Shoots were cleanly cut from the callus when they were large enough to distinguish from stems. The shoots were placed on hormone-free rooting media (MSO: MS salts 4.3 g/l, sucrose 30 g/l, and B5 vitamins 500X 2 ml/l) with selection. Roots formed in 1-2 weeks. Any leaf callus assays are preferably done on rooted shoots while still sterile. Rooted shoots were placed in soil and were kept in a high humidity environment (ie: plastic containers or bags). The shoots were hardened off by gradually exposing them to ambient humidity conditions.

A total of 45 Kanamycin resistant pMON17032 tobacco lines were examined (Table V).

TABLE V

Expression of Modified Glyphosate Oxidoreductase Gene in Tobacco
(R1 Transgenics of pMON17032)

| # Plants | Glyphosate Recallusing (0.5 mM glyphosate) | | | Western Analysis of Plants‡ | |
|---|---|---|---|---|---|
| | + | +/− | − | + | − |
| 45 | 0 | 11 | 34 | 24 | 21 |

‡+ means 0.5 - 2 ng/50 μg protein
− means <0.5 ng/50 μg protein

Leaf recallusing on plant tissue culture media indicated a low level of glyphosate tolerance (rated as a +/−phenotype) for at least 11 of these lines. At least 24 of these lines expressed a detectable level of glyphosate oxidoreductase in the range of 0.5 to 2 ng per 50 μg of extractable protein. The glyphosate tolerance displayed in the leaf recallusing assay and the higher glyphosate oxidoreductase expression level indicate that the changes made to the glyphosate oxidoreductase coding sequences to make the modified glyphosate oxidoreductase gene (SEQ ID NO:7) had a marked effect on the ability of this gene to be expressed in plants. This same effect could also then be achieved by expressing the manipulated glyphosate oxidoreductase gene (SEQ ID NO:6) using stronger plant promoters, using better 3' polyadenylation signal sequences, optimizing the sequences around the initiation codon for ribosome loading and translation initiation, or by combinations of these or other expression or regulatory sequences or factors. The R1 progeny of a number of these lines, including those with the highest glyphosate oxidoreductase expression level (#'s 18854 and 18848) were sprayed with glyphosate at rates of 0.4 and 1.0 lb/acre (0.448 and 1.12 kg/ha, respectively) and vegetative performance rated over a period of four weeks (Table VI).

TABLE VI

Tobacco Spray Data for pMON17032 R1 Plants

| Line | Rate kg/ha | Vegetative Score* | | |
|---|---|---|---|---|
| | | 7 Days | 14 Days | 28 Days |
| 18860 | 0.448 | 3 | 3 | 4 |
| | 1.12 | 1 | 1 | 2 |
| 18842 | 0.448 | 4 | 6 | 8 |
| | 1.12 | 2 | 3 | 6 |
| 18848 | 0.448 | 3 | 4 | 8 |
| | 1.12 | 2 | 2 | 6 |
| 18854 | 0.448 | 4 | 7 | 9 |
| | 1.12 | 2 | 5 | 8 |
| 18858 | 0.448 | 3 | 4 | 6 |
| | 1.12 | 1 | 2 | 4 |
| 18885 | 0.448 | 4 | 5 | 8 |
| | 1.12 | 2 | 1 | 2 |
| 18890 | 0.448 | 3 | 6 | 7 |
| | 1.12 | 1 | 2 | 3 |
| Samsun | 0.448 | 1 | 1 | 2 |
| | 1.12 | 1 | 1 | 0 |

*Vegetative Score
0 = Dead
10 = No detectable effect

Following an initial lag, and especially for those plants expressing the highest levels of glyphosate oxidoreductase, these lines showed vegetative glyphosate tolerance at both spray rates (that improved with time). Glyphosate oxidoreductase enzyme activity was determined for two of the pMON17032 lines (#'s 18858 and 18881). Leaf tissue (1 g) was harvested, frozen in liquid $N_2$, and stored at −80° C. prior to extraction. For extraction, leaf tissue was pulverized in a mortar and pestle with liquid $N_2$. To the powdered leaf tissue was then added 1 ml extraction buffer (100 mM TrisCl, pH 7.4, 1 mM EDTA, 20% glycerol, 35 mM KCl, 1 mM benzamidine HCl, 5 mM Na ascorbate, 5 mM dithiothreitol, and 1 mg/ml bovine serum albumin, 4° C.), and the sample was further ground for 1 minute. The resulting mixture was centrifuged for 5 minutes (high speed, Eppendorf) and the supernatant was treated with a saturated ammonium sulfate solution to give 70% final saturation (2.33 ml saturated solution/ml extract). The precipitated protein was collected by centrifugation as above, and the pellet was resuspended in 0.4 ml of extraction buffer. After centrifuging again to remove particulate matter, the sample was desalted using Sephadex G50 contained in a 1 ml syringe, equilibrated with extraction buffer, according to the method of Penefsky (1979). The desalted plant extracts were stored on ice, and protein concentrations were determined by the method of Bradford (1976). Glyphosate oxidoreductase reactions were carried out in duplicate for 60 minutes at 30° C. in an assay mixture of 0.1 MOPS/0.01 tricine buffer, pH 7.4, containing 10 mM $MgCl_2$, 0.01 mM flavin adenine dinucleotide (FAD, Sigma), and 1 mM ubiquinone Qo, (Sigma). Plant extracts (75 μl) were preincubated in the assay mixture for 2 minutes, and reactions were then initiated by adding iminodiacetic acid (IDA, 20 μl) substrate to a final concentration of 50 mM (total assay volume was 0.2 ml). Reactions were quenched and derivatized as described below. Control reactions omitting IDA and omitting plant extract were also performed. Glyoxylate detection was carried out using 2,4-dinitrophenylhydrazine (2,4-DNPH) derivatization and reverse phase high performance liquid chromatography (HPLC), using a modification of the method of Qureshi et al. (1982). Glyphosate oxidoreductase reactions (0.2 ml) were quenched with 0.25 ml of DNPH reagent (0.5 mg/ml DNPH [Aldrich] in 0.5M HCl) and allowed to derivatize for 5 minutes at 25° C. The samples were then extracted with ethyl acetate (2×0.3 ml) and the combined ethyl acetate extracts were extracted with 10% Na$_2$CO$_3$ (0.3 ml). The Na$_2$CO$_3$ phase was then washed once with ethyl acetate (0.2 ml) and the Na$_2$CO$_3$ phase injected (100 μl) on a Beckman Ultrasphere C18 IP HPLC column (5μ, 4.6 mm×25 cm) using an LKB GTi binary HPLC system with a Waters 990 photodiode array UV/VIS HPLC detector, via a Waters WISP HPLC autoinjector. The isocratic mobile phase was methanol-water-acetic acid (60:38.5:1.5) with 5 mM tetrabutylammonium phosphate (Pierce). The DNPH-glyoxylate peak (retention time=6.7 minutes) was detected at 365 nm and compared to a glyoxylate standard (Sigma, 20 μM in 0.2 ml) derivatized in exactly the same manner.

TABLE VII

Glyphosate oxidoreductase Activity of Transgenic Tobacco Plants

| Plant | Specific Activity nmol/min mg |
|---|---|
| Samsun | 0 (not detectable) |
| 18881 | 0.039 |
| 18858 | 0.018 |

EXAMPLE 2

A series of transformed tobacco lines were derived using the "isogenic" glyphosate oxidoreductase vectors pMON17073 (manipulated glyphosate oxidoreductase) (SEQ ID NO:6), pMON17065 (synthetic glyphosate oxidoreductase) (SEQ ID NO:8), and pMON17066 (CTP1-synthetic glyphosate oxidoreductase). By Western analysis (see Table VII below) of a number of these lines, the manipulated glyphosate oxidoreductase plants were found to express up to ~0.5 ng glyphosate oxidoreductase per 50 μg plant protein, the synthetic glyphosate oxidoreductase at levels from ~0.5–2 ng per 50 μg, and at levels from ~2–20 ng per 50 μg for the CTP1-synthetic glyphosate oxidoreductase plants.

TABLE VIII

Glyphosate Oxidoreductase Expression in Tobacco

| Construct | Plant # | Western Rating |
|---|---|---|
| pMON17073 (manipulated) | 21270 | 0 |
|  | 21281 | 0 |
|  | 21286 | 1 |
|  | 21929 | 1 |
| pMON17066 (CTP1-synthetic) | 21237 | 1 |
|  | 21830 | 0 |
|  | 21845 | 3 |
|  | 21872 | 3 |
|  | 21889 | 1 |
|  | 21891 | 0 |
| pMON17065 (synthetic) | 21199 | 0 |
|  | 21208 | 2 |
|  | 21211 | 2 |
|  | 21217 | 0 |
|  | 21218 | 2 |
|  | 21792 | 1 |
|  | 21795 | 0 |
|  | 21811 | 2 |

Western rating scale per 50 μg of protein:
0 - no detectable glyphosate oxidoreductase
1 - <.5 ng
2 - .5 ng - 2ng
3 - >2 ng A number of primary transformants R$_o$ lines, expressing manipulated or synthetic glyphosate oxidoreductase or CTP1-synthetic glyphosate oxidoreductase, were sprayed with glyphosate at 0.4 lb/acre (0.448 kg/ha) and rated as before.

TABLE IX

Glyphosate Spray Data: pMON17066 (CTP1-Glyphosate Oxidoreductase) Tobacco (R$_O$ plants)

| Line | Western Rating | Vegetative Score # (Spray Rate = 0.4 lb/acre) (0.448 kg/ha) | | |
|---|---|---|---|---|
|  |  | 7 | 14 | 28 (days after spray) |
| Control A | 0 | 3 | 0 | 0 no detectable |
| Control B | 0 | 3 | 1 | 0 glyphosate |
| Control C | 0 | 3 | 1 | 1 oxidoreductase |
| 22933 | 1 | 3 | 1 | 0 (pMON17073) |
| 22741 | 2 | 2 | 1 | 9 (pMON17065) |
| 22810 | 3 | 3 | 4 | 6 (pMON17066) |
| 22825 | 1 | 2 | 1 | 1 (pMON17066) |
| 22822 | 3 | 10 | 10 | 10 (pMON17066) |
| 22844 | 3 | 10 | 10 | 10 (pMON17066) |
| 22854 | 3 | 9 | 10 | 10 (pMON17066) |
| 22860 | 3 | 8 | 10 | 10 (pMON17066) |
| 22880 | 1 | 3 | 2 | 9 (pMON17066) |
| 22881 | 2 | 2 | 0 | 0 (pMON17066) |
| 22886 | 3 | 9 | 10 | 10 (pMON17066) |
| 22887 | 3 | 9 | 10 | 10 (pMON17066) |

Western rating scale
(per 50 μg protein)
0 = no detectable glyphosate oxidoreductase
1 = <0.5 ng
2 = 0.5 - 2 ng
3 = >2 ng
Vegetative score:
0 = dead;
10 = no detectable effect The synthetic glyphosate oxidoreductase line displayed a response similar to that noted for the modified glyphosate oxidoreductase R$_1$ plants, in that there was some immediate glyphosate effects that were overcome with time, through the metabolism of the herbicide by glyphosate oxidoreductase to the derivatives AMPA and glyoxylate. Since the target of glyphosate (EPSP synthase) is located in the chloroplast, the activity of glyphosate oxidoreductase must be reducing the level of glyphosate within this organelle by removing the herbicide before it reaches the chloroplast. The CTP1-synthetic glyphosate oxidoreductase plants displayed a superior glyphosate tolerance in that these plants did not show much, if any, immediate glyphosate effects at the treated rate. In general, the treated tolerant plants also showed normal development, flowering and fertility.

The CTP1-synthetic glyphosate oxidoreductase plants showed a markedly higher level of glyphosate oxidoreductase expression than that shown for the other glyphosate oxidoreductase constructs. This increased glyphosate oxidoreductase level could be due to enhancement of translation of the fusion or to sequestering of glyphosate oxidoreductase within the chloroplast and leading to a longer protein half-life. The higher level of glyphosate oxidoreductase and/or its location in the chloroplast can result in higher levels of glyphosate tolerance through rapid detoxification of glyphosate in the chloroplast. The presence of glyphosate oxidoreductase within the chloroplast has been confirmed. Five leaves from each of four plants (#22844, 22854, 22886, 22887), shown to be Western positive for glyphosate oxidoreductase, were homogenized in Waring blender in 0.9 L GR+ buffer (Bartlett, et al., 1982) for 3×3 seconds at high speed. The homogenate was filtered through 4 layers of Miracloth and centrifuged at 6,000 rpm in a GS-3 rotor. The pellet was resuspended in 4 ml total of GR+ buffer and placed on top of a 40/80% Percoll step gradient and spun at 9,500 rpm for 10 minutes. The intact chloroplasts (lower band) were washed once with GR− buffer (Bartlett, et al., 1982) and centrifuged (up to 6,000 rpm with brake off). They were then resuspended in 300 µl 50 mM Hepes pH 7.7, 330 mM Sorbitol and lysed on ice using by sonication (small probe, 30%-3 microtip setting×10 seconds). The debris was pelleted and the supernatant passed through a Sephadex G50 column into 50 mM Hepes, pH 7.5. The soluble protein concentration was 2.4 mg/ml. The enzyme assays were done as above using both 50 mM IDA and 50 mM glyphosate as substrates (30 minute assays), but without the addition of 1 mM ubiquinone.

TABLE IX

Glyphosate Oxidoreductase Activity in Isolated Chloroplast from Transgenic Tobacco

| Substrate | Specific Activity (nmoles/min.mg) |
|---|---|
| Iminodiacetic acid | 179 |
| Glyphosate | 92 |

EXAMPLE 3

A number of transformed lines of canola have been derived with vectors pMON17138 (CTP1-synthetic glyphosate oxidoreductase) and pMON17164 (CTP2-synthetic glyphosate oxidoreductase) as follows.

Plant Material

Seedlings of *Brassica napus* cv Westar were established in 2 inch (~5 cm) pots containing Metro Mix 350. They were grown in a growth chamber at 24° C., 16/8 hour photoperiod, light intensity of 400 uEm-$^{2}$sec$^{-1}$ (HID lamps). They were fertilized with Peters 20-10-20 General Purpose Special. After 2½ weeks they were transplanted to 6 inch (~15 cm) pots and grown in a growth chamber at 15/10° C. day/night temperature, 16/8 hour photoperiod, light intensity of 800 uEm-$^{2}$sec$^{-1}$ (HID lamps). They were fertilized with Peters 15-30-15 Hi-Phos Special.

Transformation/Selection/Regeneration

Four terminal internodes from plants just prior to bolting or in the process of bolting but before flowering were removed and surfaced sterilized in 70% v/v ethanol for 1 minute, 2% w/v sodium hypochlorite for 20 minutes and rinsed 3 times with sterile deionized water. Stems with leaves attached could be refrigerated in moist plastic bags for up to 72 hours prior to sterilization. Six to seven stem segments were cut into 5 mm discs with a Redco Vegetable Slicer 200 maintaining orientation of basal end.

The Agrobacterium was grown overnight on a rotator at 24° C. in 2 mls of Luria Broth containing 50 mg/l kanamycin, 24 mg/l chloramphenicol and 100 mg/l spectinomycin. A 1:10 dilution was made in MS (Murashige and Skoog) media giving approximately 9×10$^8$ cells per ml. This was confirmed with optical density readings at 660 mu. The stem discs (explants) were inoculated with 1.0 ml of Agrobacterium and the excess was aspirated from the explants.

The explants were placed basal side down in petri plates containing 1/10X standard MS salts, B5 vitamins, 3% sucrose, 0.8% agar, pH 5.7, 1.0 mg/l 6-benzyladenine (BA). The plates were layered with 1.5 ml of media containing MS salts, B5 vitamins, 3% sucrose, pH 5.7, 4.0 mg/l p-chlorophenoxyacetic acid, 0.005 mg/l kinetin and covered with sterile filter paper.

Following a 2 to 3 day co-culture, the explants were transferred to deep dish petri plates containing MS salts, B5 vitamins, 3% sucrose, 0.8% agar, pH 5.7, 1 mg/l BA, 500 mg/l carbenicillin, 50 mg/l cefotaxime, 200 mg/l kanamycin or 175 mg/l gentamicin for selection. Seven explants were placed on each plate. After 3 weeks they were transferred to fresh media, 5 explants per plate. The explants were cultured in a growth room at 25° C., continuous light (Cool White).

Expression Assay

After 3 weeks shoots were excised from the explants. Leaf recallusing assays were initiated to confirm modification of R$_o$ shoots. Three tiny pieces of leaf tissue were placed on recallusing media containing MS salts, B5 vitamins, 3% sucrose, 0.8% agar, pH 5.7, 5.0 mg/l BA, 0.5 mg/l naphthalene acetic acid (NAA), 500 mg/l carbenicillin, 50 mg/l cefotaxime and 200 mg/l kanamycin or gentamicin or 0.5 mM glyphosate. The leaf assays were incubated in a growth room under the same conditions as explant culture. After 3 weeks the leaf recallusing assays were scored for herbicide tolerance (callus or green leaf tissue) or sensitivity (bleaching).

Transplantation

At the time of excision, the shoot stems were dipped in Rootone® and placed in 2 inch (~5 cm) pots containing Metro-Mix 350 and placed in a closed humid environment. They were placed in a growth chamber at 24° C., 16/8 hour photoperiod, 400 uEm-$^1$sec-$^2$(HID lamps) for a hardening-off period of approximately 3 weeks.

The seed harvested from R$_o$ plants is R$_1$ seed which gives rise to R$_1$ plants. To evaluate the glyphosate tolerance of an R$_o$ plant, its progeny are evaluated. Because an R$_o$ plant is assumed to be hemizygous at each insert location, selfing results in maximum genotypic segregation in the R$_1$. Because each insert acts as a dominant allele, in the absence of linkage and assuming only one hemizygous insert is required for tolerance expression, one insert would segregate 3:1, two inserts, 15:1, three inserts 63:1, etc. Therefore, relatively few R$_1$ plants need be grown to find at least one resistant phenotype.

Seed from an R$_o$ plant is harvested, threshed, and dried before planting in a glyphosate spray test. Various techniques have been used to grow the plants for R$_1$ spray evaluations. Tests are conducted in both greenhouses and growth chambers. Two planting systems are used; ~10 cm pots or plant trays containing 32 or 36 cells. Soil used for planting is either Metro 350 plus three types of slow release fertilizer or plant Metro 350. Irrigation is either overhead in greenhouses or subirrigation in growth chambers. Fertilizer is applied as required in irrigation water. Temperature regimes appropriate for canola were maintained. A sixteen hour photoperiod was maintained. At the onset of flowering, plants are transplanted to ~15 cm pots for seed production.

A spray "batch" consists of several sets of R$_1$ progenies all sprayed on the same date. Some batches may also include evaluations of other than R$_1$ plants. Each batch also includes sprayed and unsprayed non-transgenic genotypes representing the genotypes in the particular batch which were putatively transformed. Also included in a batch is one or more non-segregating transformed genotypes previously identified as having some resistance.

Two-six plants from each individual $R_o$ progeny are not sprayed and serve as controls to compare and measure the glyphosate tolerance, as well as to assess any variability not induced by the glyphosate. When the other plants reach the 2–4 leaf stage, usually 10 to 20 days after planting, glyphosate is applied at rates varying from 0.28 to 1.12 kg/ha, depending on objectives of the study. Low rate technology using low volumes has been adopted. A laboratory track sprayer has been calibrated to deliver a rate equivalent to field conditions.

A scale of 0 to 10 is used to rate the sprayed plants for vegetative resistance. The scale is relative to the unsprayed plants from the same $R_o$ plant. A 0 is death, while a 10 represents no visible difference from the unsprayed plant. A higher number between 0 and 10 represents progressively less damage as compared to the unsprayed plant. Plants are scored at 7, 14, and 28 days after treatment (DAT), or until bolting, and a line is given the average score of the sprayed plants within an $R_o$ plant family.

Six integers are used to qualitatively describe the degree of reproductive damage from glyphosate:

0: No floral bud development

2: Floral buds present, but aborted prior to opening

4: Flowers open, but no anthers, or anthers fail to extrude past petals

6: Sterile anthers

8: Partially sterile anthers

10: Fully fertile flowers

Plants are scored using this scale at or shortly after initiation of flowering, depending on the rate of floral structure development.

Tables X and XI below tabulate the vegetative and reproductive scores for canola plants transformed with pMON17138 (sprayed at a rate of 0.56 kg/ha and pMON17164 (sprayed at a rate of 0.84 kg/ha), respectively. The results presented below illustrate the glyphosate tolerance conferred to canola plants as a result of expression of a glyphosate oxidoreductase gene in the plants.

TABLE X

Glyphosate Spray Evaluation of Canola Plants containing pMON17138

| Line name | Batch | 0.56 kg/ha score 14 DAT Vegetative | 0.56 kg/ha score 28 DAT Reproductive |
|---|---|---|---|
| 17138-22 | 79 | 9 | 10 |
| 17138-30 | 79 | 9 | 10 |
| 17138-145 | 79 | 10 | 10 |
| 17138-158 | 79 | 8 | 10 |
| 17138-164 | 80 | 8 | 10 |
| Untransformed | 77 | 3 | 0 |
| Untransformed | 79 | 1 | 0 |

TABLE XI

Glyphosate Spray Evaluation of Canola Plants containing pMON17164

| Construct | Batch | 0.84 kg/ha score 14 DAT vegetative | 28 DAT reproductive |
|---|---|---|---|
| 17164-6 | 82 | 7 | 10 |
| 17164-9 | 83 | 8 | 10 |
| 17164-20 | 82 | 7 | 10 |
| 17164-25 | 83 | 8 | 10 |
| 17164-35 | 84 | 7 | 10 |
| 17164-45 | 83 | 9 | 10 |
| 17164-61 | 83 | 7 | 10 |
| 17164-75 | 84 | 7 | 10 |
| 17164-85 | 84 | 7 | 10 |
| 17164-97 | 84 | 6 | 10 |
| 17164-98 | 83 | 9 | 10 |
| 17164-105 | 83 | 7 | 10 |
| 17164-110 | 83 | 9 | 10 |
| 17164-115 | 83 | 7 | 10 |
| 17164-129 | 83 | 8 | 10 |
| 17164-139 | 84 | 7 | 10 |
| 17164-140 | 83 | 8 | 10 |
| 17164-164 | 83 | 7 | 10 |
| 17164-166 | 83 | 8 | 10 |
| 17164-174 | 83 | 8 | 10 |
| 17164-186 | 83 | 3 | 10 |
| 17164-202 | 83 | 8 | 10 |
| 17164-218 | 84 | 6 | 10 |
| 17164-219 | 83 | 9 | 10 |
| 17164-222 | 84 | 7 | 10 |
| 17164-225 | 83 | 7 | 10 |
| 17164-227 | 84 | 7 | 10 |
| 17164-230 | 83 | 8 | 10 |
| 17164-243 | 83 | 7 | 10 |
| 17164-247 | 84 | 7 | 10 |
| 17164-287 | 84 | 7 | 10 |
| 17164-289 | 83 | 8 | 10 |
| 17164-300 | 83 | 9 | 10 |
| 17164-337 | 83 | 8 | 10 |

EXAMPLE 4

Figure 10:
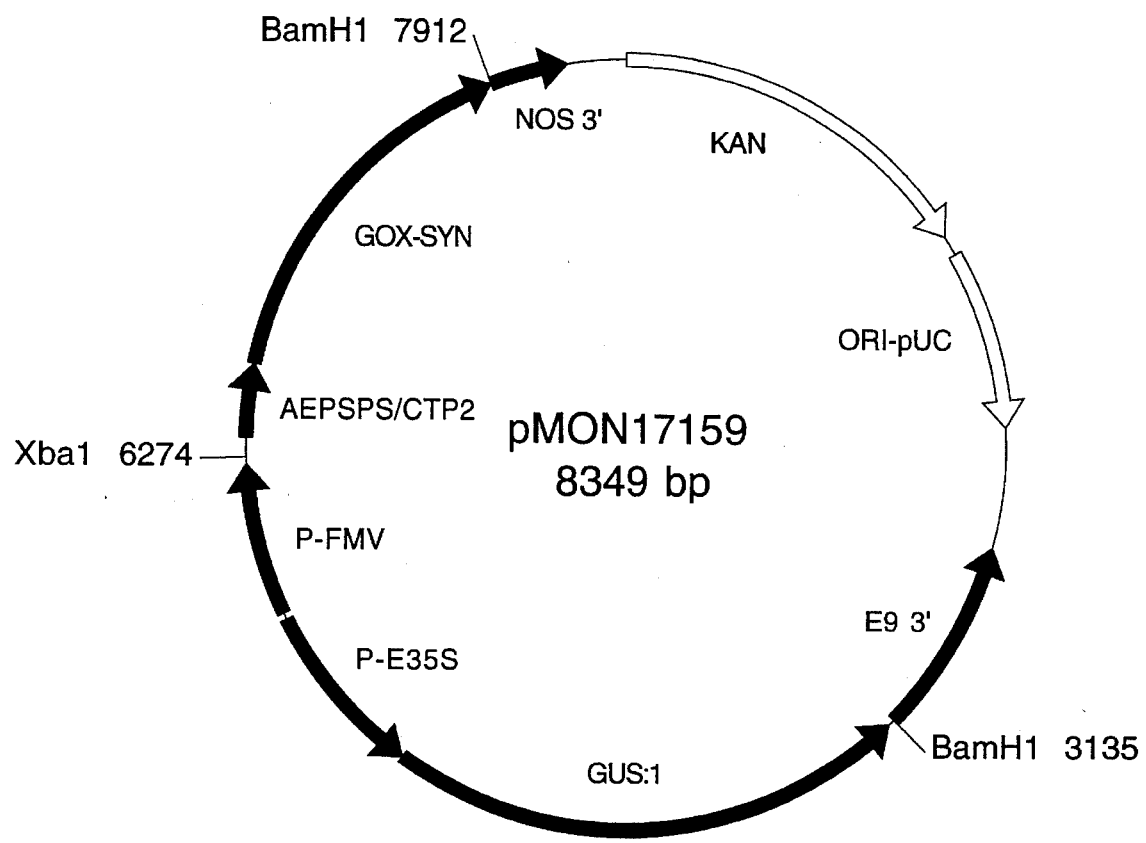
FIG. 10 shows the structural map of plasmid pMON17159.

The glyphosate oxidoreductase gene has also been introduced into and expressed in soybean and imparts glyphosate tolerance to such plants. The CTP2-synthetic glyphosate oxidoreductase fusion gene (as described above) was introduced into soybean under the control of the FMV promoter and with the NOS 3' sequences in vector pMON17159, a map of which is presented in FIG. 10. This vector consists of the following elements in addition to the glyphosate oxidoreductase gene sequences; the pUC origin of replication, an NPTII bacterial selectable marker gene (kanamycin) and the beta-glucuronidase gene (GUS; Jefferson eta. 1986) under the control of the E35S promoter and with the E9 3' sequences. The latter gene provides a scorable marker to facilitate the identification of transformed plant material.

Soybean plants are transformed with pMON17159 by the method of microprojectile injection using particle gun technology as described in Christou et al. (1988). The seed harvested from $R_o$ plants is $R_1$ seed which gives rise to $R_1$ plants. To evaluate the glyphosate tolerance of an $R_o$ plant, its progeny are evaluated. Because an $R_o$ plant is assumed to be hemizygous at each insert location, selfing results in maximum genotypic segregation in the $R_1$. Because each insert acts as a dominant allele, in the absence of linkage and assuming only one hemizygous insert is required for tolerance expression, one insert would segregate 3:1, two inserts, 15:1, three inserts 63:1, etc. Therefore, relatively few $R_1$ plants need be grown to find at least one resistant phenotype.

Seed from an $R_o$ soybean plant is harvested, and dried before planting in a glyphosate spray test. Seeds are planted into 4 inch (~5 cm) square pots containing Metro 350. Twenty seedlings from each Ro plant is considered adequate for testing. Plants are maintained and grown in a greenhouse environment. A 12.5–14 hour photoperiod and temperatures of 30° C. day and 24° C. night is regulated. Water soluble Peters Pete Lite fertilizer is applied as needed.

A spray "batch" consists of several sets of $R_1$ progenies all sprayed on the same date. Some batches may also include evaluations of other than $R_1$ plants. Each batch also includes sprayed and unsprayed non-transgenic genotypes representing the genotypes in the particular batch which were putatively transformed. Also included in a batch is one or more non-segregating transformed genotypes previously identified as having some resistance.

One to two plants from each individual $R_o$ progeny are not sprayed and serve as controls to compare and measure the glyphosate tolerance, as well as to assess any variability not induced by the glyphosate. When the other plants reach the first trifoliolate leaf stage, usually 2–3 weeks after planting, glyphosate is applied at a rate equivalent to 128 oz./acre (8.895 kg/ha) of Roundup®. A laboratory track sprayer has been calibrated to deliver a rate equivalent to those conditions.

A vegetative score of 0 to 10 is used. The score is relative to the unsprayed progenies from the same $R_o$ plant. A 0 is death, while a 10 represents no visible difference from the unsprayed plant. A higher number between 0 and 10 represents progressively less damage as compared to the unsprayed plant. Plants are scored at 7, 14, and 28 days after treatment (DAT).

TABLE XII

Glyphosate Spray Evaluation of Soybean Plants containing pMON17159

| Line | Batch | Score @ 8.895 kg/ha, 28 DAT |
| --- | --- | --- |
| 17159-24 | 14 | 9 |
| 17159-25 | 14 | 9 |
| 17159-28 | 14 | 6 |
| 17159-40 | 14 | 4 |
| 17159-43 | 14 | 4 |
| 17159-71 | 14 | 10 |
| 17159-77 | 14 | 9 |
| 17159-81 | 15 | 4 |
| Untransformed | 14 | 0 |

EXAMPLE 5

The glyphosate oxidoreductase gene has also been introduced into Black Mexican Sweet (BMS) corn cells with expression of the protein detected in callus.

Plasmid pMON19632 was used to introduce the glyphosate oxidoreductase gene into corn cells. The backbone for this plasmid was constructed by inserting the 0.6 kb cauliflower mosaic virus (CaMV) 35S RNA promoter (E35S) containing a duplication of the −90 to −300 region (Kay et al., 1987), a 0.58 kb fragment containing the first intron from the maize alcohol dehydrogenase gene (Callis et al., 1987), and the 3' termination sequences from the nopaline synthase (NOS) gene (Fraley et al., 1983) into pUC119 (Yanisch-Perron et al., 1985). pMON19632 was formed by inserting the 1.7 kb BglII/EcoRI fragment from pMON17064 which contains the Arabidopsis SSU CTP fused to the synthetic glyphosate oxidoreductase coding sequence (SEQ IN NO:8).

Plasmid pMON19632 was introduced into BMS corn cells by co-bombardment with EC9, a plasmid containing a sulfonylurea-resistant form of the maize acetolactate synthase gene. 2.5 µg of each plasmid was coated onto tungsten particles and introduced into log-phase BMS cells using a PDS-1000 particle gun essentially as described in Klein et al., 1989. Transformants were selected on MS medium containing 20ppb chlorsulfuron. After initial selection on chlorsulfuron, the calli was assayed by glyphosate oxidoreductase Western blot.

BMS callus (3 g wet weight) was dried on filter paper (Whatman#1) under vacuum, reweighed, and extraction buffer (500 µl/g dry weight; 100 mM Tris, 1 mM EDTA, 10% glycerol) was added. The tissue was homogenized with a Wheaton overhead stirrer for 30 seconds at 2.8 power setting. After centrifugation (3 minutes, Eppendorf microfuge), the supernatant was removed and the protein was quantitated (BioRad Protein Assay). Samples (50 µg/well) were loaded on an SDS PAGE gel (Jule, 3–17%) along with glyphosate oxidoreductase standard (10 ng), electrophoresed, and transferred to nitrocellulose similarly to a previously described method (Padgette, 1987). The nitrocellulose blot was probed with goat anti-glyphosate oxidoreductase IgG, and developed with I-125 Protein G. The radioactive blot was visualized by autoradiography. Results were quantitated by densitometry on an LKB UltraScan XL laser densitomer and are tabulated below in Table XIII.

TABLE XIII

Expression of glyphosate oxidoreductase in BMS Corn Callus using pMON19632

| Line | GOX expression (% extracted protein) |
| --- | --- |
| EC9 (no GOX) | 0 |
| T13-17 | 0.016 |
| T13-16 | 0.0065 |
| T13-15 | 0.016 |
| T13-14 | 0.003 |
| T13-12 | 0.0079 |
| T13-7 | 0.01 |
| T13-5 | 0.004 |
| T13-18 | 0.026 |
| T13-8 | 0.019 |
| T13-9 | 0.01 |
| T13-4 | 0.027 |

Table XIII illustrates that glyphosate oxidoreductase can be expressed and detected in a monocotyledonous plant, such as corn.

EXAMPLE 6

The glyphosate oxidoreductase gene may be used as a selectable marker for plant transformation directly on media containing glyphosate. The ability to select and to identify transformed plant material depends, in most cases, on the use of a dominant selectable marker gene to enable the preferential and continued growth of the transformed tissues in the presence of a normally inhibitory substance. Antibiotic resistance and herbicide tolerance genes have been used almost exclusively as such dominant selectable marker genes in the presence of the corresponding antibiotic or herbicide. The nptII/kanamycin selection scheme is probably the most frequently used. It has been demonstrated that glyphosate oxidoreductase is also a useful and perhaps superior selectable marker/selection scheme for producing and identifying transformed plants.

Figure 11:
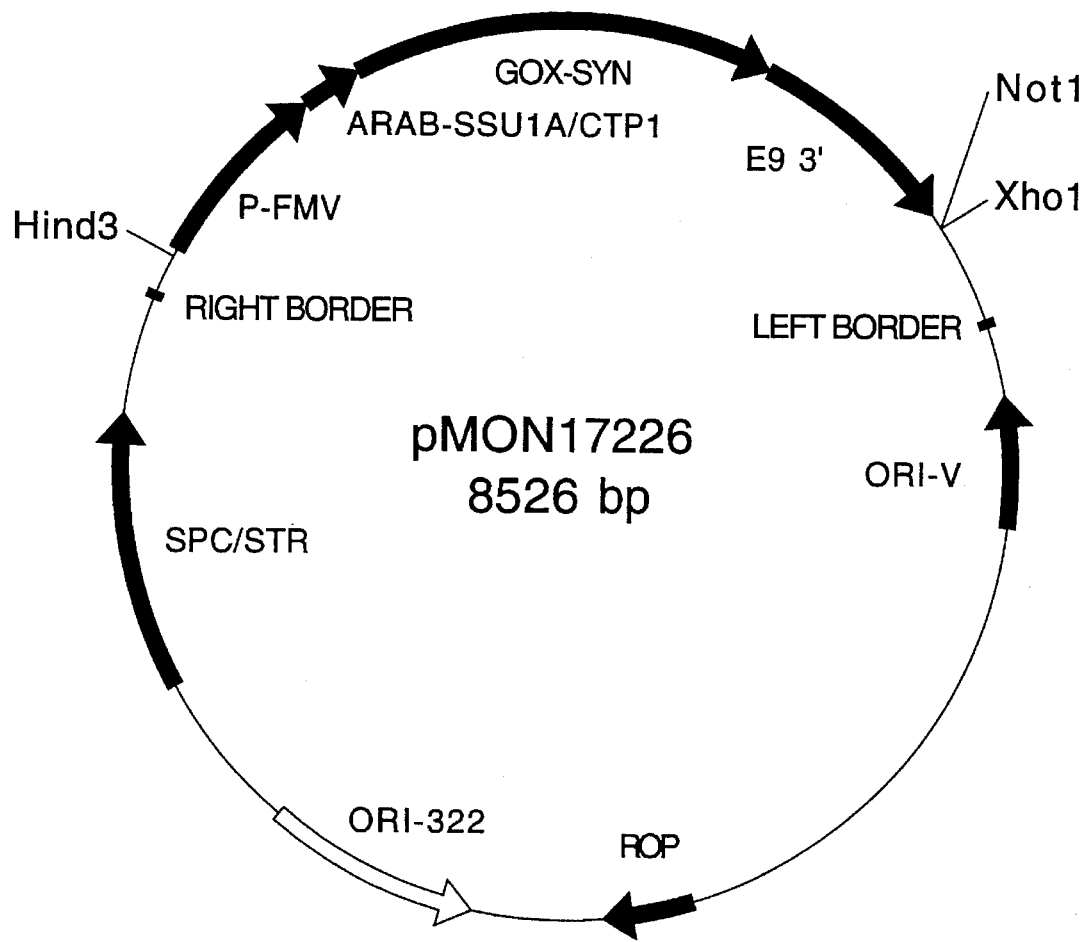
FIG. 11 shows the structural map of plasmid pMON17226.

A plant transformation vector that may be used in this scheme is pMON17226 (FIG. 11). This plasmid resembles many of the other plasmids described infra and is essentially composed of the previously described bacterial replicon system that enables this plasmid to replicate in E. coli and to be introduced into and to replicate in Agrobacterium, the bacterial selectable marker gene (Spc/Str), and located between the T-DNA right border and left border is the CTP1-glyphosate oxidoreductase synthetic gene in the FMV promoter-E9 3' cassette. This plasmid also has single sites for a number of restriction enzymes, located within the borders and outside of the expression cassette. This makes it possible to easily add other genes and genetic elements to the vector for introduction into plants.

The protocol for direct selection of transformed plants on glyphosate is outlined for tobacco. Explants are prepared for pre-culture as in the standard procedure as described in Example 1: surface sterilization of leaves from 1 month old tobacco plants (15 minutes in 10% clorox+surfactant; 3X $dH_2O$ washes); explants are cut in 0.5×0.5 cm squares, removing leaf edges, mid-fib, tip, and petiole end for uniform tissue type; explants are placed in single layer, upside down, on MS104 plates+2 ml 4COO5K media to moisten surface; pre-culture 1–2 days. Explants are inoculated using overnight culture of Agrobacterium containing the plant transformation plasmid that is adjusted to a titer of $1.2 \times 10^9$ bacteria/ml with 4COO5K media. Explants are placed into a centrifuge tube, the Agrobacterium suspension is added and the mixture of bacteria and explants is "Vortexed" on maximum settting for 25 seconds to ensure even penetration of bacteria. The bacteria are poured off and the explants are blotted between layers of dry sterile filter paper to remove excess bacteria. The blotted explants are placed upside down on MS104 plates+2 ml 4COO5K media+filter disc. Co-culture is 2–3 days. The explants are transferred to MS104+Carbenicillin 1000 mg/l+cefotaxime 100 mg/1 for 3 days (delayed phase). The explants are then transferred to MS104+glyphosate 0.05 mM+Carbenicillin 1000 mg/l+cefotaxime 100 mg/l for selection phase. At 4–6 weeks shoots are cut from callus and placed on MSO+Carbenicillin 500 mg/l rooting media. Roots form in 3–5 days, at which time leaf pieces can be taken from rooted plates to confirm glyphosate tolerance and that the material is transformed.

The presence of the glyphosate oxidoreductase protein in these transformed tissues has been confirmed by immunoblot analysis of leaf discs. The data from one experiment with pMON17226 is presented in the following: 25 shoots formed on glyphosate from 100 explants inoculated with Agrobacterium ABI/pMON17226; 15 of these were positive on recallusing on glyphosate, and 19 of these were positive for glyphosate oxidoreductase protein as detected by immunoblot. These data indicate a transformation rate of 15–19 per 100 explants, which makes this a highly efficient and time saving transformation procedure for plant. Similar transformation frequencies have been obtained with a pMON17226 derivative (pMON17241) containing the gene for the glyphosate oxidoreductase v.247 (SEQ ID NO:17). The glyphosate oxidoreductase gene has also been shown to enable direct selection of transformants in other plant species, including Arabidopsis, potato, and sugarbeet.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

BIBLIOGRAPHY

Ammirato, P. V., et al. Handbook of Plant Cell Culture—Crop Species. Macmillan Publ. Co. (1984).

Avila, L. Z., Loo, S. H. and Frost, J. W. (1987) Chemical and mutagenic analysis of aminomethylphosphonate biodegradation. J. Amer. Chem. Soc. 109: 6758–6764.

Balthazor, T. M. and Hallas, L. E. (1986) Glyphosate-degrading microorganisms from industrial activated sludge. Appl. Environ. Microbiol. 51:432–434.

Bartlett, S. G., Grossman, A. R., and Chua, N. H. (1982) in Methods in Chloroplast Molecular Biology, pp. 1081–1091. M. Edelman, R. B., Hallick, and Chua, N. H.,eds.

Bevan, M. (1984) Nucleic Adds Res. 12 (22): 8711–8721.

Birnboim, H. C. and Doly, J. (1979) A rapid alkaline extraction procedure for screening recombinant plasmid DNA. Nucl. Adds. Res. 7:1513–1525.

Boyer, H. W. and Rolland-Dussoix, D. (1969) A complementation analysis of the restriction and modification of DNA in Escherichia coli. J. Mol. Biol. 41:459.

Bradford, M. Anal. Biochem. 72, 248 (1976).

Callis, J., Fromm, M., and Walbot, V. (1987) Introns increase gene expression in cultured maize cells. Genes and Dev. 1:1183–1200.

Christou, P., D. E. McCabe, and W. F. Swain (1988) Stable transformation of Soybean Callus by DNA-Coated Gold Particles. Plant Physiol. 87:671–674.

Cook, A. M., Daughton, C. G. and Alexander, M. (1978) Phosphonate utilization by bacteria. J. Bacteriol. 133: 85–90.

Coruzzi, G., Broglie, R., Edwards, C., and Chua, N. H. (1984). Tissue-specific and light-regulated expression of a pea nuclear gene encoding the small subunit of ribulose-1, 5-bisphosphate carboxylase. EMBO J 3, 1671–1679.

Coupland, D. (1985) Metabolism of glyphosate in plants, in The Herbicide Glyphosate. eds. E. Grossbard and D. Atkinson. Butterworths. pp. 25–34.

Daughton, C. G., Cook, A. M. and Alexander, M. (1979a) Bacterial conversion of alkylphosphonates to natural products via carbon-phosphorus bond cleavage. J. Agric. Food Chem. 27:1375–1382.

Daughten, C. G., Cook, A. M. and Alexander, M. (1979b) Biodegradation of phosphonate toxicants yields methane or ethane on cleavage of the C-P bond. FEMS Microbiol. Lett. 5:91–93.

Daughten, C. G., Cook, A. M. and Alexander, M. (1979c) Phosphate and soil binding: factors limiting bacterial degradation of ionic phosphorous-containing pesticide metabolites. Appl. Environ. Microbiol. 37: 605–609.

della-Cioppa, G., Bauer, S. C., Klein, B. K., Shah, D. M., Fraley, R. T. and Kishore G. K. (1986) Translocation of the precursor of 5-enolpyruvylshikimate-3-phosphate synthase into chloroplasts of higher plants in vitro. Proc. Natl. Acad Sci. USA 83: 6873–6877.

della-Cioppa, G., Bauer, S. C., Taylor, M. T., Rochester, D. E., Klein, B. K., Shah, D. M., Fraley, R. T. and Kishore G. M. (1987) Targeting a herbicide-resistant enzyme from *Escherichia coli* to chloroplasts of higher plants. Bio/Technology 5: 579–584.

Ditta, G., Stanfield, S., Corbin, D., and Helinski, D. R. (1980). Broad host range DNA cloning system for Gram-Negative bacteria: construction of a gene bank of *Rhizobium meliloti*. Proc Natl Acad Sci USA 77, 7347–7351.

Erlich, H. A. (1989) Ed. *PCR Technology—Principles and Applications for DNA Amplification.* Stockton Press, New York.

Fling, M. E., Kopf, J., and Richards, C. (1985). Nucleotide sequence of the transposon Tn7 gene encoding an aminoglycoside-modifying enzyme, 3"(9)-O-nucleotidyltransferase. Nucleic Acids Research 13 no. 19, 7095–7106.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA 80:4803–4807.

Fraley, R. T., Rogers, S. G., Horsch, R. B., Eichholtz D. A., Flick, J. S., Fink, C. L., Hoffmann, N. L. and Sanders, P. R. (1985) The SEV system: a new disarmed Ti plasmid vector system for plant transformation.

Franz, J. E. (1985) Discovery, development and chemistry of glyphosate, in *The Herbicide Glyphosate.* eds. E. Grossbard and D. Atkinson. Butterworths. pp. 3–17.

Fromm, M., (1990) UCLA Symposium on Molecular Strategies for Crop Improvement, Apr. 16–22, 1990. Keystone, Colo.

Gowda, S., Wu, F. C., and Shepard, R. J. (1989). Identification of promoter sequences for the major RNA transcripts of figwort mosaic and peanut chlorotic streak viruses (caulimovirus group). Journal of Cellular Biochemistry supplement 13D, 301. (Abstract)

Hallas, L. E., Hahn, E. M. and Korndorfer, C. (1988) Characterization of microbial traits associated with glyphosate biodegradation in industrial activated sludge. J. Industrial Microbiol. 3: 377–385.

Hayford, M. B., Medford, J. I., Hoffmann, N. L., Rogers, S. G. and Klee, H. J. (1988) Development of a plant transformation selection system based on expression of genes encoding gentamicin acetyltransferases. Plant Physiol. 86: 1216–1222.

Heitkamp, M. A., Hallas, L. and Adams, W. J. (1990) Biotreatment of industrial wastewater with immobilized microorganisms—Presented in Session 11, Paper S40, Society for Industrial Microbiology Annual Meeting, Orlando, Fla., Jul. 29–Aug. 3, 1990.

Herrera-Estrella, L., et al. (1983) *Nature* 303:209 Horsch, R. B. and H. Klee. (1986) *Proc. Natl. Acad. Sci. U.S.A.* 83:4428–32.

Holben, W. E., Jannson, J. K., Chelm, B. K. and Teidje, J. M. (1988) DNA probe method for the detection of specific microorganisms in the soil bacterial community. Appl. Environ. Microbiol. 54: 703–711.

Hohn, B. and Collins J. (1980) A small cosmid for efficient cloning of large DNA fragments. Gene 11: 291–298.

Jacob, G. S., Schaefer, J., Stejskal, E. O. and McKay, R. A. (1985) Solid-state NMR determination of glyphosate metabolism in a *Pseudomonas sp.* J. Biol. Chem. 260: 5899–5905.

Jacob, G. S., Garbow, J., Hallas, L. E., Kishore, G. M. and Schaefer, J. (1988) Metabolism of glyphosate in *Pseudomonas sp.* strain LBr. Appl. Environ. Microbiol. 54: 2953–2958.

Jefferson, R. A., T. A. Kavanaugh, M. W. Bevan (1987) GUS fusions: β-glucuronidase as a sensitive and versatile gene fusion marker in higher plants. The *EMBO Journal* vol.6, no.13. pp 3901–3907.

Kay, R., Chan, A., Daly, M. and McPherson, J. (1987) Duplication of the CaMV 35S promoter sequences creates a strong enhancer for plant genes. Science 236:1299–1302.

Kishore, G. M. and Jacob G. S. (1987) Degradation of glyphosate by *Pseudomonas sp.* PG2928 via a sarcosine intermediate. J. Biol. Chem. 262: 12164–12168.

Klee, H. J., et al. (1985) *Bio/Technology* 3:637–42.

Klee, H. J., Muskopf, Y. M. and Gasser, C. S. (1987) Cloning of an *Arabidopsis thaliana* gene encoding 5-enolpyruvylshikimate-3-phosphate synthase: sequence analysis and manipulation to obtain glyphosate tolerant plants. Mol. Gen. Genet. 210: 437–442.

Klein, T. M., Kornstein, L., Sanford, J. C., and Fromm, M. E. (1989) Genetic transformation of maize cells by particle bombardment. *Plant Phys.* 91:440–444.

Koncz, C. and Schell, J. (1986) The promoter of TL-DNA gene 5 controls the tissue-specific expression of chimeric genes carried by a novel type of Agrobacterium binary vector. Mol. Gen. Genet. 204:383–396.

Lerbs, W., Stock, M. and Parthier, B. (1990) Physiological aspects of glyphosate degradation in *Alcaligenes sp.* strain GL. Arch. Microbiol. (1990) 153: 146–150.

Liu, C.-M., McLean, P. A., Sookdeo, C. C. and Cannon, F. C. (1991) Degradation of the herbicide glyphosate by members of the family Rhixobiaceae. Appl. Environ. Microbiol. 57: 1799–1804.

Maier, L. (1983) Phosphorus Sulfur 14:295.

Malik, J., Barry, G. and Kishore, G. (1989) The herbicide glyphosate. BioFactors 2:17–25.

Maniatis, T., Fritsch, E. F. and Sambrook, J. (1982) Molecular Cloning: a laboratory manual. Cold Spring Harbor Laboratory, Cold Spring Harbor, N.Y.

Marshall, G., Kirkwood, R. C. and Martin, D. J. (1987) Pestic. Sci. 18:65–77.

Mastalerz, P., Wieczorek, Z. and Kochman, M (1965) Utilization of carbon-bound phosphorus by microorganisms. Acta Biochim. Pol. 12:151–156.

Miller, J. H. (1972). Experiments in Molecular Genetics. Cold Spring Harbor Laboratory, Cold Spring Harbor, N.Y.

Moore, J. K., Braymer, H. D. and Larson, A.D. (1983) Isolation of a *Pseudomonas sp.* which utilizes the phosphonate herbicide glyphosate. Appl. Environ. Microbiol. 46: 316–320.

Morelli, G., Nagy, F., Fraley, R. T., Rogers, S. G., and Chua, N. H. (1985). A short conserved sequence is involved in the light-inducibility of a gene encoding ribulose 1,5-bisphosphate carboxylase small subunit of pea. Nature 315, 200–204.

Neidhardt, F. C., Bloch, P. L. and Smith, D. F. (1974) Culture media for enterobacteria. J. Bacteriol. 119: 736–747.

Nomura, N. S. and Hilton, H. W. (1977) The adsorption and degradation of glyphosate in five Hawaiian sugarcane soils. Weed Res. 17: 113–121.

Odell, J. T., Nagy, F., and Chua, N. H. (1985). Identification of DNA sequences required for activity of the cauliflower mosaic virus 35S promoter. Nature 313,810–812.

Padgette, S., et al. (1987) Bacterial Expression and Isolation of *Petunia hybrida* EPSP Synthase. *Arch. Biochem. Biophys.* 258:564–573

Penefsky, H. S., *Meth. Enzymol.* 56, 527–530 (1979).

Pipke, R., Schulz, A. and Amrhein, N. (1987b) Uptake of glyphosate by an *Arthrobacter sp.* Appl. Environ. Microbiol. 53:974–978.

Pipke, R. and Amrhein, N. (1988) Degradation of the phosphonate herbicide glyphosate by *Arthrobacter atrocyaneus* ATCC 13752. Appl. Environ. Microbiol. 54: 1293–1296.

Pipke, R., Amrhein, N., Jacob, G. S. and Kishore, G. M. (1987a) Metabolism of glyphosate by an *Arthrobacter sp.* GLP-1. Eur. J. Biochem. 165: 267–273.

Quinn, J. P., Peden, J. M. M. and Dick, E. (1988) Glyphosate tolerance and utilization by the microflora of soils treated with the herbicide. Appl. Microbiol. Biotechnol. 29: 511–516.

Quinn, J. P., Peden, J. M. M. and Dick, R. E. (1989) Appl. Microbiol. and Biotechnology 31:283–287.

Qureshi, A. A., Elson, C. E., and Lebeck, L. A., *J. Chromotog.* 249, 333–345 (1982).

Rueppel, M. L., Brightwell, B. B., Schaefer, J. and Marvel, J. T. (1977) Metabolism and degradation of glyphosate in soil and water. J. Agric. Food Chem. 25:517–528.

Schowanek, D. and Verstraete, W. (1990) Phosphonate utilization by bacterial cultures and enrichments from environmental samples. Appl. Environ. Microbiol. 56: 895–903.

Shah, D., Horsch, R., Klee, H., Kishore, G., Winter, J., Tumer, N., Hironaka, C., Sanders, P., Gasser, C., Aykent, S., Siegal, N., Rogers, S., and Fraley, R. (1986). Engineering herbicide tolerance in transgenic plants. Science 233, 478–481.

Shimamoto, K. et al. (1989) *Nature* 338:274–276.

Shinabarger, D. L. and Braymer, H. D. (1986) Glyphosate catabolism by *Pseudomonas sp.* strain PG2982. J. Bacteriol. 168:702–707.

Stalker, D. M., Thomas, C. M., and Helinski, D. R. (1981). Nucleotide sequence of the region of the origin of replication of the broad host range plasmid RK2. Mol Gen Genet 181: 8–12.

Steffan, R. J. and Atlas, R. M. (1988) DNA amplification to enhance detection of genetically engineered bacteria in environmental samples. Appl. Environ. Microbiol. 54: 2185–2191.

Tabor, S. and Richardson, C. C. (1985) A bacteriophage T7 RNA polymerase/promoter system for controlled exclusive expression of specific genes. Proc. Natl. Acad. Sci. USA 82: 1074–1078.

Talbot, H. W., Johnson, L. M. and Munnecke, D. M. (1984) Glyphosate utilization by *Pseudomonas sp.* and *Alcaligenes sp.* isolated from environmental sources. Current Microbiol. 10:255–260.

Tanaka, J., Kuwano, E. and Eto, M. (1986) Synthesis and pesticidal activities of phosphonate analogs of amino acids. J. Fac. Agr. Kyushu Univ. 30: 209–223.

Timko, M. P., Herdies, L., de Alameida, E., Cashmore, A. R., Leemans, J. and Krebbers, E. (1988) Genetic engineering of nuclear-encoded components of the photosynthetic apparatus of Arabidopsis in *The Impact of Chemistry on Biotechnology—A Multidisciplinary Discussion*. ACS Books, Washington D.C. pp279–295

Torstensson, L. (1985) Behavior of glyphosate in soils and its degradation, in *The Herbicide Glyphosate*. eds. E. Grossbard and D. Atkinson. Butterworths. pp. 137–150.

Tsai, Y.-L. and Olson, B. H. (1991) Rapid method for direct isolation of DNA from soil and sediments. Appl. Environ. Microbiol. 57:1070–1074.

Vasil, V., F. Redway and I. Vasil. (1990) *Bio/Technology* 8:429–434.

Vieira, J. and Messing, J. (1987) Production of single-stranded plasmid DNA. Methods. Enzymol. 153:3.

Wackett, L. P., Shames, S. L., Venditti, C. P. and Walsh, C. T. (1987a) Bacterial carbon-phosphorus lyase: products, rates, and regulation of phosphonic and phosphinic acid metabolism. J. Bacteriol. 169: 710–717.

Wackett, L. P., Wanner, B. L., Venditti, C. P. and Walsh, C. T. (1987b) Involvement of the phosphate regulon and the psiD locus in the carbon-phosphorus lyase activity of *Escherichia coli* K-12. J. Bacteriol. 169: 1753–1756.

Weidhase, R., Albrecht, B., Stock, M., and Weidhase, R. A. (1990) Utilization of glyphosate by *Pseudomonas sp.* GS. Zentralbl. Mikrobiol. 145:6.

Wong, E. Y., Seetharam, R., Kotts, C. E., Heeren, R. A., Klein, B. K., Braford, S. R., Mathis, K. J., Bishop, B. F., Siegel, N. R., Smith, C. E. and Tacon, W. C. (1988) Expression of excreted insulin-like growth factor-1 in *Escherichia coli*. Gene 68:193–203.

Yanisch-Perron, C., Vierra, J. and Messing, J. (1985) Improved M13 phage cloning vectors and host strains: nucleotide sequences of the M13mp18 and pUC19 vectors. *Gene* 33, 103–119.

Zeleznick, L. D., Meyers, T. C. and Titchener, E. B. (1963) Growth of *Escherichia coli* on methyl- and ethylphosphonic acids. Biochim. Biophys. Acta. 78: 546–547.

---

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
      ( A ) LENGTH: 564 base pairs
      ( B ) TYPE: nucleic acid
      ( C ) STRANDEDNESS: double (D) TOPOLOGY: linear (ii) MOLECULE TYPE: DNA (genomic)

(xi) SEQUENCE DESCRIPTION: SEQ ID NO:1:

| | | | | | | |
|---|---|---|---|---|---|---|
| ATTTAGCAGC | ATTCCAGATT | GGGTTCAATC | AACAAGGTAC | GAGCCATATC | ACTTTATTCA | 60 |
| AATTGGTATC | GCCAAAACCA | AGAAGGAACT | CCCATCCTCA | AAGGTTTGTA | AGGAAGAATT | 120 |
| CTCAGTCCAA | AGCCTCAACA | AGGTCAGGGT | ACAGAGTCTC | CAAACCATTA | GCCAAAAGCT | 180 |
| ACAGGAGATC | AATGAAGAAT | CTTCAATCAA | AGTAAACTAC | TGTTCCAGCA | CATGCATCAT | 240 |
| GGTCAGTAAG | TTTCAGAAAA | AGACATCCAC | CGAAGACTTA | AAGTTAGTGG | GCATCTTTGA | 300 |
| AAGTAATCTT | GTCAACATCG | AGCAGCTGGC | TTGTGGGGAC | CAGACAAAAA | AGGAATGGTG | 360 |
| CAGAATTGTT | AGGCGCACCT | ACCAAAAGCA | TCTTTGCCTT | TATTGCAAAA | GATAAAGCAG | 420 |
| ATTCCTCTAG | TACAAGTGGG | GAACAAAATA | ACGTGGAAAA | GAGCTGTCCT | GACAGCCCAC | 480 |
| TCACTAATGC | GTATGACGAA | CGCAGTGACG | ACCACAAAAG | AATTTTCCCT | CTATATAAGA | 540 |
| AGGCATTTCA | TTCCCATTTG | AAGG | | | | 564 |

(2) INFORMATION FOR SEQ ID NO:2:

(i) SEQUENCE CHARACTERISTICS:
  (A) LENGTH: 27 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:2:

| | | | |
|---|---|---|---|
| ATCATCAGAT | ACTAACCAAT | ATTTCTC | 27 |

(2) INFORMATION FOR SEQ ID NO:3:

(i) SEQUENCE CHARACTERISTICS:
  (A) LENGTH: 1689 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:3:

| | | | | | | |
|---|---|---|---|---|---|---|
| NCATGGACGT | CTGATCGAAA | TCGTCGTTAC | CGCAGCAAGG | TAAGGCACGC | CGAATTTTAT | 60 |
| CACCTACCGC | GAAACGGTGG | CTAGGCAGCG | AGAGACTGTC | GGCTCCGCGG | GAGCATCCTA | 120 |
| TGTCTGAGAA | CCACAAAAAA | GTAGGCATCG | CTGGAGCCGG | AATCGTCGGC | GTATGCACGG | 180 |
| CGCTGATGCT | TCAGCGCCGC | GGATTCAAAG | TCACCTTGAT | TGACCCGAAC | CCTCCTGGCG | 240 |
| AAGGTGCATC | GTTTGGGAAT | GCCGGATGCT | TCAACGGCTC | ATCCGTCGTC | CCTATGTCCA | 300 |
| TGCCGGGAAA | CTTGACGAGC | GTGCCGAAGT | GGCTCCTTGA | CCCGATGGGC | CGTTGTCAAT | 360 |
| CCGGTTCAGC | TATTTCCAAC | CATCATGCCT | GGTTGATTCG | CTTTCTGTTA | GCCGGAAGAC | 420 |
| CAAACAAGGT | GAAGGAGCAG | GCGAAAGCAC | TCCGCAATCT | CATCAAGTCC | ACGGTGCCTC | 480 |
| TGATCAAGTC | ATTGGCGGAG | GAGGCTGATG | CGAGCCATCT | GATCCGCCAT | GAAGGTCATC | 540 |
| TGACCGTATA | TCGTGGAGAA | GCAGACTTCG | CCAAGGACCG | CGGAGGTTGG | GAACTGCGGC | 600 |
| GTCTCAACGG | TGTTCGCACG | CAGATCCTCA | GCGCCGATGC | GTTGCGGGAT | TCGATCCGA | 660 |
| ACTTGTCGCA | TGCGTTTACC | AAGGGCATTC | TTATAGAAGA | GAACGGTCAC | ACGATTAATC | 720 |
| CGCAAGGGCT | CGTGACCCTC | TTGTTTCGGC | GTTTTATCGC | GAACGGTGGC | GAATTCGTAT | 780 |

-continued

```
CTGCGCGTGT CATCGGCTTT GAGACTGAAG GTAGGGCGCT TAAAGGCATT ACAACCACGA      840

ACGGCGTTCT GGCCGTTGAT GCAGCGGTTG TCGCAGCCGG CGCACACTCG AAATCACTTG      900

CTAATTCGCT AGGCGATGAC ATCCCGCTCG ATACCGAACG TGGATATCAT ATCGTCATCG      960

CGAATCCGGA AGCCGCTCCA CGCATTCCGA CGACCGATGC GTCAGGAAAA TTCATCGCGA     1020

CACCTATGGA AATGGGGCTT CGCGTGGCGG GTACGGTTGA GTTCGCTGGG CTCACAGCCG     1080

CTCCTAACTG GAAACGTGCG CATGTGCTCT ATACGCACGC TCGAAAACTT CTTCCAGCCC     1140

TCGCGCCTGC GAGTTCTGAA GAACGATATT CCAAATGGAT GGGGTTCCGG CCGAGCATCC     1200

CGGATTCGCT CCCCGTGATT GGCCGGGCAA CCCGGACACC CGACGTAATC TATGCTTTCG     1260

GCCATGGTCA TCTCGGCATG ACAGGGGCGC CGATGACCGC AACGCTCGTC TCAGAGCTCC     1320

TCGCAGGCGA AAAGACCTCA ATCGACATTT CGCCCTTCGC ACCAAACCGC TTTGGTATTG     1380

GCAAATCCAA GCAAACGGGT CCGGCAAGTT AAGTACTTAC GCGGTCGTGA GTACAGCGCA     1440

GAGCCGGTGT CAAGATCAAT CTGCACCTCG CAATCACCTC GGAGACGCGA AATGGCGCAA     1500

ATAGAACACA TATTAACGAG TCACGCCCCG AAGCCTTTGG GTCACTACAG TCAGGCGGCC     1560

CGAGCGGGTG GATTCATTCA TGTTTCCGGT CAGCTTCCGA TCAAACCAGA AGGCCAGTCG     1620

GAGCAATCTG ACGATCTCGT CGATAACCAG GCCAGTCTCG TTCTCCGGAA TTTGCTGGCC     1680

GTACTCGAG                                                             1689
```

( 2 ) INFORMATION FOR SEQ ID NO:4:

( i ) SEQUENCE CHARACTERISTICS:
        ( A ) LENGTH: 1293 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1293

( x i ) SEQUENCE DESCRIPTION: SEQ ID NO:4:

```
ATG  TCT  GAG  AAC  CAC  AAA  AAA  GTA  GGC  ATC  GCT  GGA  GCC  GGA  ATC  GTC      48
Met  Ser  Glu  Asn  His  Lys  Lys  Val  Gly  Ile  Ala  Gly  Ala  Gly  Ile  Val
 1                    5                        10                       15

GGC  GTA  TGC  ACG  GCG  CTG  ATG  CTT  CAG  CGC  CGC  GGA  TTC  AAA  GTC  ACC      96
Gly  Val  Cys  Thr  Ala  Leu  Met  Leu  Gln  Arg  Arg  Gly  Phe  Lys  Val  Thr
               20                       25                       30

TTG  ATT  GAC  CCG  AAC  CCT  CCT  GGC  GAA  GGT  GCA  TCG  TTT  GGG  AAT  GCC     144
Leu  Ile  Asp  Pro  Asn  Pro  Pro  Gly  Glu  Gly  Ala  Ser  Phe  Gly  Asn  Ala
          35                       40                       45

GGA  TGC  TTC  AAC  GGC  TCA  TCC  GTC  GTC  CCT  ATG  TCC  ATG  CCG  GGA  AAC     192
Gly  Cys  Phe  Asn  Gly  Ser  Ser  Val  Val  Pro  Met  Ser  Met  Pro  Gly  Asn
     50                       55                       60

TTG  ACG  AGC  GTG  CCG  AAG  TGG  CTC  CTT  GAC  CCG  ATG  GGC  CGT  TGT  CAA     240
Leu  Thr  Ser  Val  Pro  Lys  Trp  Leu  Leu  Asp  Pro  Met  Gly  Arg  Cys  Gln
65                       70                       75                       80

TCC  GGT  TCA  GCT  ATT  TCC  AAC  CAT  CAT  GCC  TGG  TTG  ATT  CGC  TTT  CTG     288
Ser  Gly  Ser  Ala  Ile  Ser  Asn  His  His  Ala  Trp  Leu  Ile  Arg  Phe  Leu
                    85                       90                       95

TTA  GCC  GGA  AGA  CCA  AAC  AAG  GTG  AAG  GAG  CAG  GCG  AAA  GCA  CTC  CGC     336
Leu  Ala  Gly  Arg  Pro  Asn  Lys  Val  Lys  Glu  Gln  Ala  Lys  Ala  Leu  Arg
               100                      105                      110

AAT  CTC  ATC  AAG  TCC  ACG  GTG  CCT  CTG  ATC  AAG  TCA  TTG  GCG  GAG  GAG     384
```

|     |     |     |     |     |     |     |     |     |     |     |     |     |     |     |     |     |
|---|---|---|---|---|---|---|---|---|---|---|---|---|---|---|---|---|
| Asn | Leu | Ile | Lys | Ser | Thr | Val | Pro | Leu | Ile | Lys | Ser | Leu | Ala | Glu | Glu | |
|     |     | 115 |     |     |     | 120 |     |     |     |     | 125 |     |     |     |     |     |

| GCT | GAT | GCG | AGC | CAT | CTG | ATC | CGC | CAT | GAA | GGT | CAT | CTG | ACC | GTA | TAT | 432 |
|---|---|---|---|---|---|---|---|---|---|---|---|---|---|---|---|---|
| Ala | Asp | Ala | Ser | His | Leu | Ile | Arg | His | Glu | Gly | His | Leu | Thr | Val | Tyr | |
| 130 |     |     |     |     | 135 |     |     |     |     | 140 |     |     |     |     |     |     |

| CGT | GGA | GAA | GCA | GAC | TTC | GCC | AAG | GAC | CGC | GGA | GGT | TGG | GAA | CTG | CGG | 480 |
|---|---|---|---|---|---|---|---|---|---|---|---|---|---|---|---|---|
| Arg | Gly | Glu | Ala | Asp | Phe | Ala | Lys | Asp | Arg | Gly | Gly | Trp | Glu | Leu | Arg | |
| 145 |     |     |     |     | 150 |     |     |     |     | 155 |     |     |     |     | 160 |     |

| CGT | CTC | AAC | GGT | GTT | CGC | ACG | CAG | ATC | CTC | AGC | GCC | GAT | GCG | TTG | CGG | 528 |
|---|---|---|---|---|---|---|---|---|---|---|---|---|---|---|---|---|
| Arg | Leu | Asn | Gly | Val | Arg | Thr | Gln | Ile | Leu | Ser | Ala | Asp | Ala | Leu | Arg | |
|     |     |     |     | 165 |     |     |     |     | 170 |     |     |     |     | 175 |     |     |

| GAT | TTC | GAT | CCG | AAC | TTG | TCG | CAT | GCG | TTT | ACC | AAG | GGC | ATT | CTT | ATA | 576 |
|---|---|---|---|---|---|---|---|---|---|---|---|---|---|---|---|---|
| Asp | Phe | Asp | Pro | Asn | Leu | Ser | His | Ala | Phe | Thr | Lys | Gly | Ile | Leu | Ile | |
|     |     |     | 180 |     |     |     |     | 185 |     |     |     |     | 190 |     |     |     |

| GAA | GAG | AAC | GGT | CAC | ACG | ATT | AAT | CCG | CAA | GGG | CTC | GTG | ACC | CTC | TTG | 624 |
|---|---|---|---|---|---|---|---|---|---|---|---|---|---|---|---|---|
| Glu | Glu | Asn | Gly | His | Thr | Ile | Asn | Pro | Gln | Gly | Leu | Val | Thr | Leu | Leu | |
|     |     | 195 |     |     |     |     | 200 |     |     |     |     | 205 |     |     |     |     |

| TTT | CGG | CGT | TTT | ATC | GCG | AAC | GGT | GGC | GAA | TTC | GTA | TCT | GCG | CGT | GTC | 672 |
|---|---|---|---|---|---|---|---|---|---|---|---|---|---|---|---|---|
| Phe | Arg | Arg | Phe | Ile | Ala | Asn | Gly | Gly | Glu | Phe | Val | Ser | Ala | Arg | Val | |
| 210 |     |     |     |     | 215 |     |     |     |     | 220 |     |     |     |     |     |     |

| ATC | GGC | TTT | GAG | ACT | GAA | GGT | AGG | GCG | CTT | AAA | GGC | ATT | ACA | ACC | ACG | 720 |
|---|---|---|---|---|---|---|---|---|---|---|---|---|---|---|---|---|
| Ile | Gly | Phe | Glu | Thr | Glu | Gly | Arg | Ala | Leu | Lys | Gly | Ile | Thr | Thr | Thr | |
| 225 |     |     |     |     | 230 |     |     |     |     | 235 |     |     |     |     | 240 |     |

| AAC | GGC | GTT | CTG | GCC | GTT | GAT | GCA | GCG | GTT | GTC | GCA | GCC | GGC | GCA | CAC | 768 |
|---|---|---|---|---|---|---|---|---|---|---|---|---|---|---|---|---|
| Asn | Gly | Val | Leu | Ala | Val | Asp | Ala | Ala | Val | Val | Ala | Ala | Gly | Ala | His | |
|     |     |     |     | 245 |     |     |     |     | 250 |     |     |     |     | 255 |     |     |

| TCG | AAA | TCA | CTT | GCT | AAT | TCG | CTA | GGC | GAT | GAC | ATC | CCG | CTC | GAT | ACC | 816 |
|---|---|---|---|---|---|---|---|---|---|---|---|---|---|---|---|---|
| Ser | Lys | Ser | Leu | Ala | Asn | Ser | Leu | Gly | Asp | Asp | Ile | Pro | Leu | Asp | Thr | |
|     |     |     | 260 |     |     |     |     | 265 |     |     |     |     | 270 |     |     |     |

| GAA | CGT | GGA | TAT | CAT | ATC | GTC | ATC | GCG | AAT | CCG | GAA | GCC | GCT | CCA | CGC | 864 |
|---|---|---|---|---|---|---|---|---|---|---|---|---|---|---|---|---|
| Glu | Arg | Gly | Tyr | His | Ile | Val | Ile | Ala | Asn | Pro | Glu | Ala | Ala | Pro | Arg | |
|     |     | 275 |     |     |     |     | 280 |     |     |     |     | 285 |     |     |     |     |

| ATT | CCG | ACG | ACC | GAT | GCG | TCA | GGA | AAA | TTC | ATC | GCG | ACA | CCT | ATG | GAA | 912 |
|---|---|---|---|---|---|---|---|---|---|---|---|---|---|---|---|---|
| Ile | Pro | Thr | Thr | Asp | Ala | Ser | Gly | Lys | Phe | Ile | Ala | Thr | Pro | Met | Glu | |
|     | 290 |     |     |     |     | 295 |     |     |     |     | 300 |     |     |     |     |     |

| ATG | GGG | CTT | CGC | GTG | GCG | GGT | ACG | GTT | GAG | TTC | GCT | GGG | CTC | ACA | GCC | 960 |
|---|---|---|---|---|---|---|---|---|---|---|---|---|---|---|---|---|
| Met | Gly | Leu | Arg | Val | Ala | Gly | Thr | Val | Glu | Phe | Ala | Gly | Leu | Thr | Ala | |
| 305 |     |     |     | 310 |     |     |     |     | 315 |     |     |     |     | 320 |     |     |

| GCT | CCT | AAC | TGG | AAA | CGT | GCG | CAT | GTG | CTC | TAT | ACG | CAC | GCT | CGA | AAA | 1008 |
|---|---|---|---|---|---|---|---|---|---|---|---|---|---|---|---|---|
| Ala | Pro | Asn | Trp | Lys | Arg | Ala | His | Val | Leu | Tyr | Thr | His | Ala | Arg | Lys | |
|     |     |     |     | 325 |     |     |     |     | 330 |     |     |     |     | 335 |     |     |

| CTT | CTT | CCA | GCC | CTC | GCG | CCT | GCG | AGT | TCT | GAA | GAA | CGA | TAT | TCC | AAA | 1056 |
|---|---|---|---|---|---|---|---|---|---|---|---|---|---|---|---|---|
| Leu | Leu | Pro | Ala | Leu | Ala | Pro | Ala | Ser | Ser | Glu | Glu | Arg | Tyr | Ser | Lys | |
|     |     |     | 340 |     |     |     |     | 345 |     |     |     |     | 350 |     |     |     |

| TGG | ATG | GGG | TTC | CGG | CCG | AGC | ATC | CCG | GAT | TCG | CTC | CCC | GTG | ATT | GGC | 1104 |
|---|---|---|---|---|---|---|---|---|---|---|---|---|---|---|---|---|
| Trp | Met | Gly | Phe | Arg | Pro | Ser | Ile | Pro | Asp | Ser | Leu | Pro | Val | Ile | Gly | |
|     |     | 355 |     |     |     |     | 360 |     |     |     |     | 365 |     |     |     |     |

| CGG | GCA | ACC | CGG | ACA | CCC | GAC | GTA | ATC | TAT | GCT | TTC | GGC | CAT | GGT | CAT | 1152 |
|---|---|---|---|---|---|---|---|---|---|---|---|---|---|---|---|---|
| Arg | Ala | Thr | Arg | Thr | Pro | Asp | Val | Ile | Tyr | Ala | Phe | Gly | His | Gly | His | |
|     | 370 |     |     |     |     | 375 |     |     |     |     | 380 |     |     |     |     |     |

| CTC | GGC | ATG | ACA | GGG | GCG | CCG | ATG | ACC | GCA | ACG | CTC | GTC | TCA | GAG | CTC | 1200 |
|---|---|---|---|---|---|---|---|---|---|---|---|---|---|---|---|---|
| Leu | Gly | Met | Thr | Gly | Ala | Pro | Met | Thr | Ala | Thr | Leu | Val | Ser | Glu | Leu | |
| 385 |     |     |     |     | 390 |     |     |     |     | 395 |     |     |     |     | 400 |     |

| CTC | GCA | GGC | GAA | AAG | ACC | TCA | ATC | GAC | ATT | TCG | CCC | TTC | GCA | CCA | AAC | 1248 |
|---|---|---|---|---|---|---|---|---|---|---|---|---|---|---|---|---|
| Leu | Ala | Gly | Glu | Lys | Thr | Ser | Ile | Asp | Ile | Ser | Pro | Phe | Ala | Pro | Asn | |
|     |     |     |     | 405 |     |     |     |     | 410 |     |     |     |     | 415 |     |     |

| CGC | TTT | GGT | ATT | GGC | AAA | TCC | AAG | CAA | ACG | GGT | CCG | GCA | AGT | TAA |     | 1293 |
|---|---|---|---|---|---|---|---|---|---|---|---|---|---|---|---|---|
| Arg | Phe | Gly | Ile | Gly | Lys | Ser | Lys | Gln | Thr | Gly | Pro | Ala | Ser |     |     | |
|     |     |     |     | 420 |     |     |     |     | 425 |     |     |     | 430 |     |     |     |

( 2 ) INFORMATION FOR SEQ ID NO:5:

( i ) SEQUENCE CHARACTERISTICS:
        ( A ) LENGTH: 430 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met 1 | Ser | Glu | Asn | His 5 | Lys | Lys | Val | Gly | Ile 10 | Ala | Gly | Ala | Gly | Ile 15 | Val |
|---|---|---|---|---|---|---|---|---|---|---|---|---|---|---|---|
| Gly | Val | Cys | Thr 20 | Ala | Leu | Met | Leu | Gln 25 | Arg | Arg | Gly | Phe | Lys 30 | Val | Thr |
| Leu | Ile | Asp 35 | Pro | Asn | Pro | Pro | Gly 40 | Glu | Gly | Ala | Ser | Phe 45 | Gly | Asn | Ala |
| Gly | Cys 50 | Phe | Asn | Gly | Ser | Ser 55 | Val | Val | Pro | Met | Ser 60 | Met | Pro | Gly | Asn |
| Leu 65 | Thr | Ser | Val | Pro | Lys 70 | Trp | Leu | Leu | Asp | Pro 75 | Met | Gly | Arg | Cys | Gln 80 |
| Ser | Gly | Ser | Ala | Ile 85 | Ser | Asn | His | His | Ala 90 | Trp | Leu | Ile | Arg | Phe 95 | Leu |
| Leu | Ala | Gly | Arg 100 | Pro | Asn | Lys | Val | Lys 105 | Glu | Gln | Ala | Lys | Ala 110 | Leu | Arg |
| Asn | Leu | Ile 115 | Lys | Ser | Thr | Val | Pro 120 | Leu | Ile | Lys | Ser | Leu 125 | Ala | Glu | Glu |
| Ala | Asp 130 | Ala | Ser | His | Leu | Ile 135 | Arg | His | Glu | Gly | His 140 | Leu | Thr | Val | Tyr |
| Arg 145 | Gly | Glu | Ala | Asp | Phe 150 | Ala | Lys | Asp | Arg | Gly 155 | Gly | Trp | Glu | Leu | Arg 160 |
| Arg | Leu | Asn | Gly | Val 165 | Arg | Thr | Gln | Ile | Leu 170 | Ser | Ala | Asp | Ala | Leu 175 | Arg |
| Asp | Phe | Asp | Pro 180 | Asn | Leu | Ser | His | Ala 185 | Phe | Thr | Lys | Gly | Ile 190 | Leu | Ile |
| Glu | Glu | Asn 195 | Gly | His | Thr | Ile | Asn 200 | Pro | Gln | Gly | Leu | Val 205 | Thr | Leu | Leu |
| Phe | Arg 210 | Arg | Phe | Ile | Ala | Asn 215 | Gly | Gly | Glu | Phe | Val 220 | Ser | Ala | Arg | Val |
| Ile 225 | Gly | Phe | Glu | Thr | Glu 230 | Gly | Arg | Ala | Leu | Lys 235 | Gly | Ile | Thr | Thr | Thr 240 |
| Asn | Gly | Val | Leu | Ala 245 | Val | Asp | Ala | Ala | Val 250 | Val | Ala | Ala | Gly | Ala 255 | His |
| Ser | Lys | Ser | Leu 260 | Ala | Asn | Ser | Leu | Gly 265 | Asp | Asp | Ile | Pro | Leu 270 | Asp | Thr |
| Glu | Arg | Gly 275 | Tyr | His | Ile | Val | Ile 280 | Ala | Asn | Pro | Glu | Ala 285 | Ala | Pro | Arg |
| Ile | Pro | Thr 290 | Thr | Asp | Ala | Ser | Gly 295 | Lys | Phe | Ile | Ala | Thr 300 | Pro | Met | Glu |
| Met 305 | Gly | Leu | Arg | Val | Ala 310 | Gly | Thr | Val | Glu | Phe 315 | Ala | Gly | Leu | Thr | Ala 320 |
| Ala | Pro | Asn | Trp | Lys 325 | Arg | Ala | His | Val | Leu 330 | Tyr | Thr | His | Ala | Arg 335 | Lys |
| Leu | Leu | Pro | Ala 340 | Leu | Ala | Pro | Ala | Ser 345 | Ser | Glu | Glu | Arg | Tyr 350 | Ser | Lys |
| Trp | Met | Gly | Phe | Arg | Pro | Ser | Ile | Pro | Asp | Ser | Leu | Pro | Val | Ile | Gly |

|     | 355 |     |     |     | 360 |     |     |     |     | 365 |     |     |     |
| --- | --- | --- | --- | --- | --- | --- | --- | --- | --- | --- | --- | --- | --- |
| Arg | Ala | Thr | Arg | Thr | Pro | Asp | Val | Ile | Tyr | Ala | Phe | Gly | His | Gly | His |
|     | 370 |     |     |     |     | 375 |     |     |     | 380 |     |     |     |
| Leu | Gly | Met | Thr | Gly | Ala | Pro | Met | Thr | Ala | Thr | Leu | Val | Ser | Glu | Leu |
| 385 |     |     |     |     | 390 |     |     |     | 395 |     |     |     |     | 400 |
| Leu | Ala | Gly | Glu | Lys | Thr | Ser | Ile | Asp | Ile | Ser | Pro | Phe | Ala | Pro | Asn |
|     |     |     |     | 405 |     |     |     | 410 |     |     |     |     | 415 |
| Arg | Phe | Gly | Ile | Gly | Lys | Ser | Lys | Gln | Thr | Gly | Pro | Ala | Ser |
|     |     |     | 420 |     |     |     | 425 |     |     |     |     | 430 |

( 2 ) INFORMATION FOR SEQ ID NO:6:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear ( i i ) MOLECULE TYPE: DNA (recombinant)

( x i ) SEQUENCE DESCRIPTION: SEQ ID NO:6:

| | | | | | |
|---|---|---|---|---|---|
| ATGGCTGAGA | ACCACAAAAA | AGTAGGCATC | GCTGGAGCCG | GAATCGTCGG | CGTATGCACG | 60 |
| GCGCTGATGC | TTCAGCGCCG | CGGATTCAAA | GTCACCTTGA | TTGACCCGAA | CCCTCCTGGC | 120 |
| GAAGGTGCAT | CGTTTGGGAA | TGCCGGATGC | TTCAACGGCT | CATCCGTCGT | CCCTATGTCC | 180 |
| ATGCCGGGAA | ACTTGACGAG | CGTGCCGAAG | TGGCTCCTTG | ACCCGATGGG | GCCGTTGTCA | 240 |
| ATCCGGTTCA | GCTATTTTCC | AACCATCATG | CCCTGGTTGA | TTCGCTTTCT | GTTAGCCGGA | 300 |
| AGACCAAACA | AGGTGAAGGA | GCAGGCGAAA | GCACTCCGCA | ATCTCATCAA | GTCCACGGTG | 360 |
| CCTCTGATCA | AGTCATTGGC | GGAGGAGGCT | GATGCGAGCC | ATCTGATCCG | CCATGAAGGT | 420 |
| CATCTGACCG | TATATCGTGG | AGAAGCAGAC | TTCGCCAAGG | ACCGCGGAGG | TTGGGAACTG | 480 |
| CGGCGTCTCA | ACGGTGTTCG | CACGCAGATC | CTCAGCGCCG | ATGCGTTGCG | GGATTTCGAT | 540 |
| CCGAACTTGT | CGCATGCGTT | TACCAAGGGC | ATTCTTATAG | AAGAGAACGG | TCACACGATT | 600 |
| AATCCGCAAG | GGCTCGTGAC | CCTCTTGTTT | CGGCGTTTTA | TCGCGAACGG | TGGCGAATTT | 660 |
| GTATCTGCGC | GTGTCATCGG | CTTTGAGACT | GAAGGTAGGG | CGCTTAAAGG | CATTACAACC | 720 |
| ACGAACGGCG | TTCTGGCCGT | TGATGCAGCG | GTTGTCGCAG | CCGGCGCACA | CTCGAAATCA | 780 |
| CTTGCTAATT | CGCTAGGCGA | TGACATCCCG | CTCGATACCG | AACGTGGATA | TCATATCGTC | 840 |
| ATCGCGAATC | CGGAAGCCGC | TCCACGCATT | CCGACGACCG | ATGCGTCAGG | AAAATTCATC | 900 |
| GCGACACCTA | TGGAAATGGG | GCTTCGCGTG | GCGGGTACGG | TTGAGTTCGC | TGGGCTCACA | 960 |
| GCCGCTCCTA | ACTGGAAACG | TGCGCATGTG | CTCTATACGC | ACGCTCGAAA | ACTTCTTCCA | 1020 |
| GCCCTCGCGC | CTGCGAGTTC | TGAAGAACGA | TATTCCAAAT | GGATGGGGTT | CCGGCCGAGC | 1080 |
| ATCCCGGATT | CGCTCCCCGT | GATTGGCCGG | GCAACCCGGA | CACCCGACGT | AATCTATGCT | 1140 |
| TTCGGCCACG | GTCATCTCGG | CATGACAGGG | GCGCCGATGA | CCGCAACGCT | CGTCTCAGAG | 1200 |
| CTCCTCGCAG | GCGAAAAGAC | CTCAATCGAC | ATTTCGCCCT | TCGCACCAAA | CCGCTTTGGT | 1260 |
| ATTGGCAAAT | CCAAGCAAAC | GGGTCCGGCA | AGTTAA | | | 1296 |

( 2 ) INFORMATION FOR SEQ ID NO:7:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear (ii) MOLECULE TYPE: DNA (recombinant)

(xi) SEQUENCE DESCRIPTION: SEQ ID NO:7:

| | | | | | |
|---|---|---|---|---|---|
| ATGGCTGAGA | ACCACAAAAA | AGTAGGCATC | GCTGGAGCTG | GAATCGTTGG | TGTATGCACT | 60
| GCTTTGATGC | TTCAACGTCG | TGGATTCAAA | GTCACCTTGA | TTGACCCGAA | CCCTCCTGGC | 120
| GAAGGTGCAT | CGTTTGGGAA | TGCCGGATGC | TTCAACGGCT | CATCCGTCGT | CCCTATGTCC | 180
| ATGCCGGGAA | ACTTGACGAG | CGTGCCGAAG | TGGCTCCTTG | ACCCGATGGG | GCCGTTGTCA | 240
| ATCCGGTTCA | GCTATTTTCC | AACCATCATG | CCCTGGTTGA | TTCGCTTTCT | GTTAGCCGGA | 300
| AGACCAAACA | AGGTGAAGGA | GCAGGCGAAA | GCACTCCGCA | ATCTCATCAA | GTCCACGGTG | 360
| CCTCTGATCA | AGTCATTGGC | GGAGGAGGCT | GATGCGAGCC | ATCTGATCCG | CCATGAAGGT | 420
| CATCTGACCG | TATATCGTGG | AGAAGCAGAC | TTCGCCAAGG | ACCGCGGAGG | TTGGGAACTG | 480
| CGGCGTCTCA | ACGGTGTTCG | CACGCAGATC | CTCTCTGCTG | ATGCTTTGCG | TGATTTCGAT | 540
| CCTAACTTGT | CGCATGCTTT | TACCAAGGGC | ATTCTTATAG | AAGAGAACGG | TCACACGATT | 600
| AATCCGCAAG | GGCTCGTGAC | CCTCTTGTTT | CGGCGTTTTA | TCGCGAACGG | TGGCGAATTT | 660
| GTATCTGCGC | GTGTCATCGG | TTTTGAGACT | GAAGGTCGTG | CTCTCAAAGG | CATTACAACC | 720
| ACTAACGGTG | TTCTGGCTGT | TGATGCAGCT | GTTGTTGCAG | CTGGTGCACA | CTCTAAATCA | 780
| CTTGCTAATT | CGCTAGGCGA | TGACATCCCG | CTCGATACCG | AACGTGGATA | TCATATCGTC | 840
| ATCGCGAATC | CGGAAGCCGC | TCCACGCATT | CCGACGACCG | ATGCGTCAGG | AAAATTCATC | 900
| GCGACACCTA | TGGAAATGGG | TCTTCGTGTT | GCTGGTACTG | TTGAGTTTGC | TGGTCTCACA | 960
| GCTGCTCCTA | ACTGGAAACG | TGCGCATGTG | CTCTATACGC | ACGCTCGAAA | ACTTCTTCCA | 1020
| GCCCTCGCGC | CTGCGAGTTC | TGAAGAACGA | TATTCCAAAT | GGATGGGTTT | TCGTCCTAGC | 1080
| ATTCCTGATT | CTCTTCCAGT | GATTGGTCGT | GCAACTCGTA | CACCCGACGT | AATCTATGCT | 1140
| TTTGGTCACG | GTCATCTCGG | TATGACAGGT | GCTCCAATGA | CTGCAACTCT | CGTCTCAGAG | 1200
| CTCCTCGCAG | GCGAAAAGAC | CTCAATCGAC | ATTTCGCCCT | TCGCACCAAA | CCGCTTTGGT | 1260
| ATTGGCAAAT | CCAAGCAAAC | GGGTCCGGCA | AGTTAA | | | 1296

(2) INFORMATION FOR SEQ ID NO:8:

(i) SEQUENCE CHARACTERISTICS:
        (A) LENGTH: 1296 base pairs
        (B) TYPE: nucleic acid
        (C) STRANDEDNESS: double
        (D) TOPOLOGY: linear (ii) MOLECULE TYPE: DNA (synthetic)

(xi) SEQUENCE DESCRIPTION: SEQ ID NO:8:

| | | | | | |
|---|---|---|---|---|---|
| ATGGCTGAGA | ACCACAAGAA | GGTTGGTATC | GCTGGAGCTG | GAATCGTTGG | TGTTTGCACT | 60
| GCTTTGATGC | TTCAACGTCG | TGGATTCAAG | GTTACCTTGA | TTGATCCAAA | CCCACCAGGT | 120
| GAAGGTGCTT | CTTTCGGTAA | CGCTGGTTGC | TTCAACGGTT | CCTCCGTTGT | TCCAATGTCC | 180
| ATGCCAGGAA | ACTTGACTAG | CGTTCCAAAG | TGGCTTCTTG | ACCCAATGGG | TCCATTGTCC | 240
| ATCCGTTTCA | GCTACTTTCC | AACCATCATG | CCTTGGTTGA | TTCGTTTCTT | GCTTGCTGGA | 300
| AGACCAAACA | AGGTGAAGGA | GCAAGCTAAG | GCACTCCGTA | ACCTCATCAA | GTCCACTGTG | 360
| CCTTTGATCA | AGTCCTTGGC | TGAGGAGGCT | GATGCTAGCC | ACCTTATCCG | TCACGAAGGT | 420
| CACCTTACCG | TGTACCGTGG | AGAAGCAGAC | TTCGCCAAGG | ACCGTGGAGG | TTGGGAACTT | 480
| CGTCGTCTCA | ACGGTGTTCG | TACTCAAATC | CTCAGCGCTG | ATGCATTGCG | TGATTTCGAT | 540

-continued

| | | | | | | |
|---|---|---|---|---|---|---|
| CCTAACTTGT | CTCACGCCTT | TACCAAGGGA | ATCCTTATCG | AAGAGAACGG | TCACACCATC | 600 |
| AACCCACAAG | GTCTCGTGAC | TCTCTTGTTT | CGTCGTTTCA | TCGCTAACGG | TGGAGAGTTC | 660 |
| GTGTCTGCTC | GTGTTATCGG | ATTCGAGACT | GAAGGTCGTG | CTCTCAAGGG | TATCACCACC | 720 |
| ACCAACGGTG | TTCTTGCTGT | TGATGCAGCT | GTTGTTGCAG | CTGGTGCACA | CTCCAAGTCT | 780 |
| CTTGCTAACT | CCCTTGGTGA | TGACATCCCA | TTGGATACCG | AACGTGGATA | CCACATCGTG | 840 |
| ATCGCCAACC | CAGAAGCTGC | TCCACGTATT | CCAACTACCG | ATGCTTCTGG | AAAGTTCATC | 900 |
| GCTACTCCTA | TGGAGATGGG | TCTTCGTGTT | GCTGGAACCG | TTGAGTTCGC | TGGTCTCACT | 960 |
| GCTGCTCCTA | ACTGGAAGCG | TGCTCACGTT | CTCTACACTC | ACGCTCGTAA | GTTGCTTCCA | 1020 |
| GCTCTCGCTC | CTGCCAGTTC | TGAAGAACGT | TACTCCAAGT | GGATGGGTTT | CCGTCCAAGC | 1080 |
| ATCCCAGATT | CCCTTCCAGT | GATTGGTCGT | GCTACCCGTA | CTCCAGACGT | TATCTACGCT | 1140 |
| TTCGGTCACG | GTCACCTCGG | TATGACTGGT | GCTCCAATGA | CCGCAACCCT | CGTTTCTGAG | 1200 |
| CTCCTCGCAG | GTGAGAAGAC | CTCTATCGAC | ATCTCTCCAT | TCGCACCAAA | CCGTTTCGGT | 1260 |
| ATTGGTAAGT | CCAAGCAAAC | TGGTCCTGCA | TCCTAA | | | 1296 |

( 2 ) INFORMATION FOR SEQ ID NO:9:

( i ) SEQUENCE CHARACTERISTICS:
        ( A ) LENGTH: 279 base pairs
        ( B ) TYPE: nucleic acid
        ( C ) STRANDEDNESS: double
        ( D ) TOPOLOGY: linear ( i i ) MOLECULE TYPE: DNA (recombinant)

( x i ) SEQUENCE DESCRIPTION: SEQ ID NO:9:

| | | | | | | |
|---|---|---|---|---|---|---|
| AGATCTCCAC | AATGGCTTCC | TCTATGCTCT | CTTCCGCTAC | TATGGTTGCC | TCTCCGGCTC | 60 |
| AGGCCACTAT | GGTCGCTCCT | TTCAACGGAC | TTAAGTCCTC | CGCTGCCTTC | CCAGCCACCC | 120 |
| GCAAGGCTAA | CAACGACATT | ACTTCCATCA | CAAGCAACGG | CGGAAGAGTT | AACTGCATGC | 180 |
| AGGTGTGGCC | TCCGATTGGA | AAGAAGAAGT | TGAGACTCT | CTCTTACCTT | CCTGACCTTA | 240 |
| CCGATTCCGG | TGGTCGCGTC | AACTGCATGC | AGGCCATGG | | | 279 |

( 2 ) INFORMATION FOR SEQ ID NO:10:

( i ) SEQUENCE CHARACTERISTICS:
        ( A ) LENGTH: 318 base pairs
        ( B ) TYPE: nucleic acid
        ( C ) STRANDEDNESS: double
        ( D ) TOPOLOGY: linear ( i i ) MOLECULE TYPE: DNA (recombinant)

( x i ) SEQUENCE DESCRIPTION: SEQ ID NO:10:

| | | | | | | |
|---|---|---|---|---|---|---|
| AGATCTATCG | ATAAGCTTGA | TGTAATTGGA | GGAAGATCAA | AATTTTCAAT | CCCCATTCTT | 60 |
| CGATTGCTTC | AATTGAAGTT | TCTCCGATGG | CGCAAGTTAG | CAGAATCTGC | AATGGTGTGC | 120 |
| AGAACCCATC | TCTTATCTCC | AATCTCTCGA | AATCCAGTCA | ACGCAAATCT | CCCTTATCGG | 180 |
| TTTCTCTGAA | GACGCAGCAG | CATCCACGAG | CTTATCGAT | TTCGTCGTCG | TGGGGATTGA | 240 |
| AGAAGAGTGG | GATGACGTTA | ATTGGCTCTG | AGCTTCGTCC | TCTTAAGGTC | ATGTCTTCTG | 300 |
| TTTCCACGGC | GTGCATGC | | | | | 318 |

( 2 ) INFORMATION FOR SEQ ID NO:11:

( i ) SEQUENCE CHARACTERISTICS:

( A ) LENGTH: 119 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:11:

| | | | | | | |
|---|---|---|---|---|---|---|
| NCATGGACGT | CTGATCGAAA | TCGTCGTTAC | CGCAGCAAGG | TAAGGCACGC | CGAATTTTAT | 60 |
| CACCTACCGC | GAAACGGTGG | CTAGGCAGCG | AGAGACTGTC | GGCTCCGCGG | GAGCATCCT | 119 |

( 2 ) INFORMATION FOR SEQ ID NO:12:

( i ) SEQUENCE CHARACTERISTICS:
( A ) LENGTH: 277 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:12:

| | | | | | | |
|---|---|---|---|---|---|---|
| GTACTTACGC | GGTCGTGAGT | ACAGCGCAGA | GCCGGTGTCA | AGATCAATCT | GCACCTCGCA | 60 |
| ATCACCTCGG | AGACGCGAAA | TGGCGCAAAT | AGAACACATA | TTAACGAGTC | ACGCCCCGAA | 120 |
| GCCTTTGGGT | CACTACAGTC | AGGCGGCCCG | AGCGGGTGGA | TTCATTCATG | TTTCCGGTCA | 180 |
| GCTTCCGATC | AAACCAGAAG | GCCAGTCGGA | GCAATCTGAC | GATCTCGTCG | ATAACCAGGC | 240 |
| CAGTCTCGTT | CTCCGGAATT | TGCTGGCCGT | ACTCGAG | | | 277 |

( 2 ) INFORMATION FOR SEQ ID NO:13:

( i ) SEQUENCE CHARACTERISTICS:
( A ) LENGTH: 33 base pairs
( B ) TYPE: nucleic acid
( C ) STRANDEDNESS: double
( D ) TOPOLOGY: linear ( i i ) MOLECULE TYPE: DNA (synthetic)

( x i ) SEQUENCE DESCRIPTION: SEQ ID NO:13:

| | | | |
|---|---|---|---|
| GAGAGACTGT | CGACTCCGCG | GGAGCATCAT | ATG | 33 |

( 2 ) INFORMATION FOR SEQ ID NO:14:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:14:

| | | | | |
|---|---|---|---|---|
| GAACGAATCC | AAGCTTCTCA | CGACCGCGTA | AGTAC | 35 |

( 2 ) INFORMATION FOR SEQ ID NO:15:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:15:

```
GCCGAGATGA  CCGTGGCCGA  AAGC                                                               24
```

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:16:

```
GGGAATGCCG  GATGCTTCAA  CGGC                                                               24
```

( 2 ) INFORMATION FOR SEQ ID NO:17:

( i ) SEQUENCE CHARACTERISTICS:
        ( A ) LENGTH: 1296 base pairs
        ( B ) TYPE: nucleic acid
        ( C ) STRANDEDNESS: double
        ( D ) TOPOLOGY: linear ( i i ) MOLECULE TYPE: DNA (recombinant)

( i x ) FEATURE:
        ( A ) NAME/KEY: CDS
        ( B ) LOCATION: 1..1296

( x i ) SEQUENCE DESCRIPTION: SEQ ID NO:17:

```
ATG  GCT  GAG  AAC  CAC  AAG  AAG  GTT  GGT  ATC  GCT  GGA  GCT  GGA  ATC  GTT     48
Met  Ala  Glu  Asn  His  Lys  Lys  Val  Gly  Ile  Ala  Gly  Ala  Gly  Ile  Val
 1                  5                        10                       15

GGT  GTT  TGC  ACT  GCT  TTG  ATG  CTT  CAA  CGT  CGT  GGA  TTC  AAG  GTT  ACC     96
Gly  Val  Cys  Thr  Ala  Leu  Met  Leu  Gln  Arg  Arg  Gly  Phe  Lys  Val  Thr
               20                       25                       30

TTG  ATT  GAT  CCA  AAC  CCA  CCA  GGT  GAA  GGT  GCC  TCT  TTC  GGT  AAC  GCT    144
Leu  Ile  Asp  Pro  Asn  Pro  Pro  Gly  Glu  Gly  Ala  Ser  Phe  Gly  Asn  Ala
          35                       40                       45

GGT  TGC  TTC  AAC  GGT  TCC  TCC  GTT  GTT  CCA  ATG  TCC  ATG  CCA  GGA  AAC    192
Gly  Cys  Phe  Asn  Gly  Ser  Ser  Val  Val  Pro  Met  Ser  Met  Pro  Gly  Asn
     50                       55                       60

TTG  ACT  AGC  GTT  CCA  AAG  TGG  CTT  CTT  GAC  CCA  ATG  GGT  CCA  TTG  TCC    240
Leu  Thr  Ser  Val  Pro  Lys  Trp  Leu  Leu  Asp  Pro  Met  Gly  Pro  Leu  Ser
 65                      70                       75                       80

ATC  CGT  TTC  GGC  TAC  TTT  CCA  ACC  ATC  ATG  CCT  TGG  TTG  ATT  CGT  TTC    288
Ile  Arg  Phe  Gly  Tyr  Phe  Pro  Thr  Ile  Met  Pro  Trp  Leu  Ile  Arg  Phe
                    85                       90                       95

TTG  CTT  GCT  GGA  AGA  CCA  AAC  AAG  GTG  AAG  GAG  CAA  GCT  AAG  GCA  CTC    336
Leu  Leu  Ala  Gly  Arg  Pro  Asn  Lys  Val  Lys  Glu  Gln  Ala  Lys  Ala  Leu
               100                      105                      110

CGT  AAC  CTC  ATC  AAG  TCC  ACT  GTG  CCT  TTG  ATC  AAG  TCC  TTG  GCT  GAG    384
Arg  Asn  Leu  Ile  Lys  Ser  Thr  Val  Pro  Leu  Ile  Lys  Ser  Leu  Ala  Glu
          115                      120                      125

GAG  GCT  GAT  GCT  AGC  CAC  CTT  ATC  CGT  CAC  GAA  GGT  CAC  CTT  ACC  GTG    432
Glu  Ala  Asp  Ala  Ser  His  Leu  Ile  Arg  His  Glu  Gly  His  Leu  Thr  Val
     130                      135                      140

TAC  CGT  GGA  GAA  GCA  GAC  TTC  GCC  AGG  GAC  CGT  GGA  GGT  TGG  GAA  CTT    480
Tyr  Arg  Gly  Glu  Ala  Asp  Phe  Ala  Arg  Asp  Arg  Gly  Gly  Trp  Glu  Leu
145                      150                      155                      160

CGT  CGT  CTC  AAC  GGT  GTT  CGT  ACT  CAA  ATC  CTC  AGC  GCT  GAT  GCA  TTG    528
Arg  Arg  Leu  Asn  Gly  Val  Arg  Thr  Gln  Ile  Leu  Ser  Ala  Asp  Ala  Leu
               165                      170                      175

CGT  GAT  TTC  GAT  CCT  AAC  TTG  TCT  CAC  GCC  TTT  ACC  AAG  GGA  ATC  CTT    576
```

|  |  |  |  |  |  |  |  |  |  |  |  |  |  |  |  |
|---|---|---|---|---|---|---|---|---|---|---|---|---|---|---|---|
| Arg | Asp | Phe | Asp<br>180 | Pro | Asn | Leu | Ser | His<br>185 | Ala | Phe | Thr | Lys | Gly<br>190 | Ile | Leu |
| ATC | GAA | GAG | AAC | GGT | CAC | ACC | ATC | AAC | CCA | CAA | GGT | CTC | GTG | ACT | CTC |
| Ile | Glu | Glu<br>195 | Asn | Gly | His | Thr | Ile | Asn<br>200 | Pro | Gln | Gly | Leu<br>205 | Val | Thr | Leu |

624

| TTG | TTT | CGT | CGT | TTC | ATC | GCT | AAC | GGT | GGA | GAG | TTC | GTG | TCT | GCT | CGT |
|---|---|---|---|---|---|---|---|---|---|---|---|---|---|---|---|
| Leu | Phe<br>210 | Arg | Arg | Phe | Ile | Ala | Asn<br>215 | Gly | Gly | Glu | Phe | Val<br>220 | Ser | Ala | Arg |

672

| GTT | ATC | GGA | TTC | GAG | ACT | GAA | GGT | CGT | GCT | CTC | AAG | GGT | ATC | ACC | ACC |
|---|---|---|---|---|---|---|---|---|---|---|---|---|---|---|---|
| Val<br>225 | Ile | Gly | Phe | Glu | Thr<br>230 | Glu | Gly | Arg | Ala | Leu<br>235 | Lys | Gly | Ile | Thr | Thr<br>240 |

720

| ACC | AAC | GGT | GTT | CTT | GCT | GTT | GAT | GCA | GCT | GTT | GTT | GCA | GCT | GGT | GCA |
|---|---|---|---|---|---|---|---|---|---|---|---|---|---|---|---|
| Thr | Asn | Gly | Val | Leu<br>245 | Ala | Val | Asp | Ala | Ala<br>250 | Val | Val | Ala | Ala | Gly<br>255 | Ala |

768

| CAC | TCC | AAG | TCT | CTT | GCT | AAC | TCC | CTT | GGT | GAT | GAC | ATC | CCA | TTG | GAT |
|---|---|---|---|---|---|---|---|---|---|---|---|---|---|---|---|
| His | Ser | Lys | Ser<br>260 | Leu | Ala | Asn | Ser | Leu<br>265 | Gly | Asp | Asp | Ile | Pro<br>270 | Leu | Asp |

816

| ACC | GAA | CGT | GGA | TAC | CAC | ATC | GTG | ATC | GCC | AAC | CCA | GAA | GCT | GCT | CCA |
|---|---|---|---|---|---|---|---|---|---|---|---|---|---|---|---|
| Thr | Glu | Arg<br>275 | Gly | Tyr | His | Ile | Val<br>280 | Ile | Ala | Asn | Pro | Glu<br>285 | Ala | Ala | Pro |

864

| CGT | ATT | CCA | ACT | ACC | GAT | GCT | TCT | GGA | AAG | TTC | ATC | GCT | ACT | CCT | ATG |
|---|---|---|---|---|---|---|---|---|---|---|---|---|---|---|---|
| Arg | Ile<br>290 | Pro | Thr | Thr | Asp | Ala | Ser<br>295 | Gly | Lys | Phe | Ile | Ala<br>300 | Thr | Pro | Met |

912

| GAG | ATG | GGT | CTT | CGT | GTT | GCT | GGA | ACC | GTT | GAG | TTC | GCT | GGT | CTC | ACT |
|---|---|---|---|---|---|---|---|---|---|---|---|---|---|---|---|
| Glu | Met<br>305 | Gly | Leu | Arg | Val<br>310 | Ala | Gly | Thr | Val | Glu<br>315 | Phe | Ala | Gly | Leu | Thr<br>320 |

960

| GCT | GCT | CCT | AAC | TGG | AAG | CGT | GCT | CAC | GTT | CTC | TAC | ACT | CGC | GCT | CGT |
|---|---|---|---|---|---|---|---|---|---|---|---|---|---|---|---|
| Ala | Ala | Pro | Asn | Trp<br>325 | Lys | Arg | Ala | His | Val<br>330 | Leu | Tyr | Thr | Arg | Ala<br>335 | Arg |

1008

| AAG | TTG | CTT | CCA | GCT | CTC | GCT | CCT | GCC | AGT | TCT | GAA | GAA | CGT | TAC | TCC |
|---|---|---|---|---|---|---|---|---|---|---|---|---|---|---|---|
| Lys | Leu | Leu | Pro<br>340 | Ala | Leu | Ala | Pro | Ala<br>345 | Ser | Ser | Glu | Glu | Arg<br>350 | Tyr | Ser |

1056

| AAG | TGG | ATG | GGT | TTC | CGT | CCA | AGC | ATC | CCG | GAT | TCC | CTT | CCA | GTG | ATT |
|---|---|---|---|---|---|---|---|---|---|---|---|---|---|---|---|
| Lys | Trp | Met<br>355 | Gly | Phe | Arg | Pro | Ser<br>360 | Ile | Pro | Asp | Ser | Leu<br>365 | Pro | Val | Ile |

1104

| GGT | CGT | GCT | ACC | CGT | ACT | CCA | GAC | GTT | ATC | TAC | GCT | TTC | GGT | CAC | GGT |
|---|---|---|---|---|---|---|---|---|---|---|---|---|---|---|---|
| Gly | Arg<br>370 | Ala | Thr | Arg | Thr<br>375 | Pro | Asp | Val | Ile | Tyr<br>380 | Ala | Phe | Gly | His | Gly |

1152

| CAC | CTC | GGT | ATG | ACT | GGT | GCT | CCA | ATG | ACC | GCA | ACC | CTC | GTT | TCT | GAG |
|---|---|---|---|---|---|---|---|---|---|---|---|---|---|---|---|
| His<br>385 | Leu | Gly | Met | Thr<br>390 | Gly | Ala | Pro | Met | Thr<br>395 | Ala | Thr | Leu | Val | Ser | Glu<br>400 |

1200

| CTC | CTC | GCA | GGT | GAG | AAG | ACC | TCT | ATC | GAC | ATC | TCT | CCA | TTC | GCA | CCA |
|---|---|---|---|---|---|---|---|---|---|---|---|---|---|---|---|
| Leu | Leu | Ala | Gly | Glu<br>405 | Lys | Thr | Ser | Ile | Asp<br>410 | Ile | Ser | Pro | Phe | Ala<br>415 | Pro |

1248

| AAC | CGT | TTC | GGT | ATT | GGT | AAG | TCC | AAG | CAA | ACT | GGT | CCT | GCA | TCC | TAA |
|---|---|---|---|---|---|---|---|---|---|---|---|---|---|---|---|
| Asn | Arg | Phe | Gly<br>420 | Ile | Gly | Lys | Ser | Lys<br>425 | Gln | Thr | Gly | Pro | Ala<br>430 | Ser |  |

1296

( 2 ) INFORMATION FOR SEQ ID NO:18:

( i ) SEQUENCE CHARACTERISTICS:
        ( A ) LENGTH: 431 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Met | Ala | Glu | Asn | His | Lys | Lys | Val | Gly | Ile | Ala | Gly | Ala | Gly | Ile | Val |
|---|---|---|---|---|---|---|---|---|---|---|---|---|---|---|---|
| 1 |  |  |  | 5 |  |  |  |  | 10 |  |  |  |  | 15 |  |

| Gly | Val | Cys | Thr | Ala | Leu | Met | Leu | Gln | Arg | Arg | Gly | Phe | Lys | Val | Thr |
|---|---|---|---|---|---|---|---|---|---|---|---|---|---|---|---|

|  |  |  |  |  | 20 |  |  |  |  | 25 |  |  |  |  | 30 |  |
|---|---|---|---|---|---|---|---|---|---|---|---|---|---|---|---|---|
| Leu | Ile | Asp<br>35 | Pro | Asn | Pro | Pro | Gly<br>40 | Glu | Gly | Ala | Ser | Phe<br>45 | Gly | Asn | Ala |
| Gly | Cys<br>50 | Phe | Asn | Gly | Ser | Ser<br>55 | Val | Val | Pro | Met | Ser<br>60 | Met | Pro | Gly | Asn |
| Leu<br>65 | Thr | Ser | Val | Pro | Lys<br>70 | Trp | Leu | Leu | Asp | Pro<br>75 | Met | Gly | Pro | Leu | Ser<br>80 |
| Ile | Arg | Phe | Gly | Tyr<br>85 | Phe | Pro | Thr | Ile | Met<br>90 | Pro | Trp | Leu | Ile | Arg<br>95 | Phe |
| Leu | Leu | Ala | Gly<br>100 | Arg | Pro | Asn | Lys | Val<br>105 | Lys | Glu | Gln | Ala | Lys<br>110 | Ala | Leu |
| Arg | Asn | Leu<br>115 | Ile | Lys | Ser | Thr | Val<br>120 | Pro | Leu | Ile | Lys | Ser<br>125 | Leu | Ala | Glu |
| Glu<br>130 | Ala | Asp | Ala | Ser | His<br>135 | Leu | Ile | Arg | His | Glu<br>140 | Gly | His | Leu | Thr | Val |
| Tyr<br>145 | Arg | Gly | Glu | Ala | Asp<br>150 | Phe | Ala | Arg | Asp | Arg<br>155 | Gly | Gly | Trp | Glu | Leu<br>160 |
| Arg | Arg | Leu | Asn | Gly<br>165 | Val | Arg | Thr | Gln | Ile<br>170 | Leu | Ser | Ala | Asp | Ala<br>175 | Leu |
| Arg | Asp | Phe | Asp<br>180 | Pro | Asn | Leu | Ser | His<br>185 | Ala | Phe | Thr | Lys | Gly<br>190 | Ile | Leu |
| Ile | Glu | Glu<br>195 | Asn | Gly | His | Thr | Ile<br>200 | Asn | Pro | Gln | Gly | Leu<br>205 | Val | Thr | Leu |
| Leu | Phe<br>210 | Arg | Arg | Phe | Ile | Ala<br>215 | Asn | Gly | Gly | Glu | Phe<br>220 | Val | Ser | Ala | Arg |
| Val<br>225 | Ile | Gly | Phe | Glu | Thr<br>230 | Glu | Gly | Arg | Ala | Leu<br>235 | Lys | Gly | Ile | Thr | Thr<br>240 |
| Thr | Asn | Gly | Val | Leu<br>245 | Ala | Val | Asp | Ala | Ala<br>250 | Val | Val | Ala | Ala | Gly<br>255 | Ala |
| His | Ser | Lys | Ser<br>260 | Leu | Ala | Asn | Ser | Leu<br>265 | Gly | Asp | Asp | Ile | Pro<br>270 | Leu | Asp |
| Thr | Glu | Arg<br>275 | Gly | Tyr | His | Ile | Val<br>280 | Ile | Ala | Asn | Pro | Glu<br>285 | Ala | Ala | Pro |
| Arg | Ile<br>290 | Pro | Thr | Thr | Asp | Ala<br>295 | Ser | Gly | Lys | Phe | Ile<br>300 | Ala | Thr | Pro | Met |
| Glu<br>305 | Met | Gly | Leu | Arg | Val<br>310 | Ala | Gly | Thr | Val | Glu<br>315 | Phe | Ala | Gly | Leu | Thr<br>320 |
| Ala | Ala | Pro | Asn | Trp<br>325 | Lys | Arg | Ala | His | Val<br>330 | Leu | Tyr | Thr | Arg | Ala<br>335 | Arg |
| Lys | Leu | Leu | Pro<br>340 | Ala | Leu | Ala | Pro | Ala<br>345 | Ser | Ser | Glu | Glu | Arg<br>350 | Tyr | Ser |
| Lys | Trp | Met<br>355 | Gly | Phe | Arg | Pro | Ser<br>360 | Ile | Pro | Asp | Ser | Leu<br>365 | Pro | Val | Ile |
| Gly | Arg<br>370 | Ala | Thr | Arg | Thr | Pro<br>375 | Asp | Val | Ile | Tyr | Ala<br>380 | Phe | Gly | His | Gly |
| His<br>385 | Leu | Gly | Met | Thr | Gly<br>390 | Ala | Pro | Met | Thr | Ala<br>395 | Thr | Leu | Val | Ser | Glu<br>400 |
| Leu | Leu | Ala | Gly | Glu<br>405 | Lys | Thr | Ser | Ile | Asp<br>410 | Ile | Ser | Pro | Phe | Ala<br>415 | Pro |
| Asn | Arg | Phe | Gly<br>420 | Ile | Gly | Lys | Ser | Lys<br>425 | Gln | Thr | Gly | Pro | Ala<br>430 | Ser |  |

( 2 ) INFORMATION FOR SEQ ID NO:19:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: DNA (synthetic)

( x i ) SEQUENCE DESCRIPTION: SEQ ID NO:19:

CGTTCTCTAC ACTCGTGCTC GTAAGTTGC                                                29

( 2 ) INFORMATION FOR SEQ ID NO:20:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:20:

CGTTCTCTAC ACTAAGGCTC GTAAGTTGC                                                29

( 2 ) INFORMATION FOR SEQ ID NO:21:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:21:

CGTTCTCTAC ACTCAAGCTC GTAAGTTGC                                                29

( 2 ) INFORMATION FOR SEQ ID NO:22:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:22:

CGTTCTCTAC ACTGCTGCTC GTAAGTTGC                                                29

( 2 ) INFORMATION FOR SEQ ID NO:23:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:23:

CTCTACACTT GGGCTCGTAA GCTTCTTCCA GC                                            32

( 2 ) INFORMATION FOR SEQ ID NO:24:

( i ) SEQUENCE CHARACTERISTICS:
    ( A ) LENGTH: 32 base pairs
    ( B ) TYPE: nucleic acid ( C ) STRANDEDNESS: single
( D ) TOPOLOGY: linear ( i i ) MOLECULE TYPE: DNA (synthetic)

( x i ) SEQUENCE DESCRIPTION: SEQ ID NO:24:

CTCTACACTA TCGCTCGTAA GCTTCTTCCA GC    32

( 2 ) INFORMATION FOR SEQ ID NO:25:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:25:

CTCTACACTC TGGCTCGTAA GCTTCTTCCA GC    32

( 2 ) INFORMATION FOR SEQ ID NO:26:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:26:

CTCTACACTG AAGCTCGTAA GCTTCTTCCA GC    32

( 2 ) INFORMATION FOR SEQ ID NO:27:

( i ) SEQUENCE CHARACTERISTICS:
( A ) LENGTH: 62 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:27:

CGCTGGAGCT GGAATCGTTG GTGTATGCAC TGCTTTGATG CTTCAACGTC GTGGATTCAA    60

AG    62

( 2 ) INFORMATION FOR SEQ ID NO:28:

( i ) SEQUENCE CHARACTERISTICS:
( A ) LENGTH: 65 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:28:

GCAGATCCTC TCTGCTGATG CTTTGCGTGA TTTCGATCCT AACTTGTCTC ATGCTTTTAC    60

CAAGG    65

( 2 ) INFORMATION FOR SEQ ID NO:29:

( i ) SEQUENCE CHARACTERISTICS:
( A ) LENGTH: 41 base pairs
( B ) TYPE: nucleic acid

```
            ( C ) STRANDEDNESS: single
            ( D ) TOPOLOGY: linear ( i i ) MOLECULE TYPE: DNA (synthetic)

( x i ) SEQUENCE DESCRIPTION: SEQ ID NO:29:

GTCATCGGTT  TTGAGACTGA  AGGTCGTGCT  CTCAAAGGCA  T                                   4 1

( 2 ) INFORMATION FOR SEQ ID NO:30:

( i ) SEQUENCE CHARACTERISTICS:
                ( A ) LENGTH: 69 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO:30:

TACAACCACT  AACGGTGTTC  TGGCTGTTGA  TGCAGCTGTT  GTTGCAGCTG  GTGCACACTC             6 0

TAAATCACT                                                                           6 9

( 2 ) INFORMATION FOR SEQ ID NO:31:

( i ) SEQUENCE CHARACTERISTICS:
                ( A ) LENGTH: 61 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO:31:

GGAAATGGGT  CTTCGTGTTG  CTGGTACTGT  TGAGTTTGCT  GGTCTCACAG  CTGCTCCTAA             6 0

C                                                                                   6 1

( 2 ) INFORMATION FOR SEQ ID NO:32:

( i ) SEQUENCE CHARACTERISTICS:
                ( A ) LENGTH: 68 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO:32:

TGGATGGGTT  TTCGTCCTAG  CATTCCTGAT  TCTCTTCCAG  TGATTGGTCG  TGCAACTCGT             6 0

ACACCCGA                                                                            6 8

( 2 ) INFORMATION FOR SEQ ID NO:33:

( i ) SEQUENCE CHARACTERISTICS:
                ( A ) LENGTH: 69 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO:33:

CGTAATCTAT  GCTTTGGTC   ACGGTCATCT  CGGTATGACA  GGTGCTCCAA  TGACTGCAAC             6 0

TCTCGTCTC                                                                           6 9
```

We claim:

1. A recombinant, double-stranded DNA molecule comprising in sequence:
   a) a promoter region which functions in plants to cause the production of an RNA sequence, operatively linked to;
   b) a structural DNA sequence that causes the production of an RNA sequence which encodes a glyphosate oxidoreductase enzyme having the sequence of SEQ ID NO: 5, operatively linked to;
   c) a 3' non-translated region which functions in plants to cause the addition of polyadenylated nucleotides to the 3' end of the RNA sequence;
   where the promoter region is heterologous with respect to the structural DNA sequence and causes sufficient expression of said enzyme in plant tissue to enhance the glyphosate tolerance of a plant transformed with said gene.

2. A DNA molecule of claim 1 in which said structural DNA sequence further comprises a 5' sequence encoding an amino-terminal chloroplast transit peptide.

3. A DNA molecule of claim 2 in which the promoter region is a plant DNA virus promoter region.

4. A DNA molecule of claim 3 in which the promoter region is selected from the group consisting of CaMV35S and FMV35S promoter regions.

5. A glyphosate tolerant plant cell comprising a DNA molecule of claim 2.

6. A glyphosate tolerant plant cell of claim 5 in which the promoter region is a plant DNA virus promoter region.

7. A glyphosate tolerant plant cell of claim 6 in which the promoter region is selected from the group consisting of CaMV35S and FMV35S promoter regions.

8. A glyphosate tolerant plant cell of claim 7 selected from the group consisting of corn, wheat, rice, soybean, cotton, sugarbeet, oilseed rape, canola, flax, sunflower, potato, tobacco, tomato, alfalfa, lettuce, apple, poplar and pine cells.

9. A glyphosate tolerant plant having inserted into its genome a recombinant, double-stranded DNA molecule comprising in sequence:
   a) a promoter region which functions in plants to cause the production of an RNA sequence, operatively linked to;
   b) a structural DNA sequence that causes the production of an RNA sequence which encodes a glyphosate oxidoreductase enzyme having the sequence of SEQ ID NO: 5, operatively linked to;
   c) a 3' non-translated region which functions in plants to cause the addition of polyadenylated nucleotides to the 3' end of the RNA sequence;
   where the promoter region is heterologous with respect to the structural DNA sequence and causes sufficient expression of said enzyme in plant tissue to enhance the glyphosate tolerance of a plant transformed with said gene.

10. A glyphosate tolerant plant of claim 9 selected from the group consisting of corn, wheat, rice, soybean, cotton, sugarbeet, oilseed rape, canola, flax, sunflower, potato, tobacco, tomato, alfalfa, lettuce, apple, poplar and pine.

11. A glyphosate tolerant plant of claim 10 in which the promoter region is from a DNA plant virus promoter region.

12. A glyphosate tolerant plant of claim 11 in which the promoter region is selected from the group consisting of CaMV35S and FMV35S promoter regions.

13. A DNA molecule of claim 1 in which the structural DNA sequence has the sequence of SEQ ID NO: 8.

14. A DNA molecule of claim 13 in which said structural DNA sequence further comprises a 5' sequence encoding an amino-terminal chloroplast transit peptide.

15. A DNA molecule of claim 14 in which the promoter region is a plant DNA virus promoter region.

16. A DNA molecule of claim 15 in which the promoter region is selected from the group consisting of CaMV35S and FMV35S promoter regions.

17. A glyphosate tolerant plant cell comprising a DNA molecule of claim 14.

18. A glyphosate tolerant plant cell of claim 17 in which the promoter region is a plant DNA virus promoter region.

19. A glyphosate tolerant plant cell of claim 18 in which the promoter region is selected from the group consisting of CaMV35S and FMV35S promoter regions.

20. A glyphosate tolerant plant cell of claim 17 selected from the group consisting of corn, wheat, rice, soybean, cotton, sugarbeet, oilseed rape, canola, flax, sunflower, potato, tobacco, tomato, alfalfa, lettuce, apple, poplar and pine cells.

21. A glyphosate tolerant plant comprising plant cells of claim 17.

22. A glyphosate tolerant plant of claim 21 selected from the group consisting of corn, wheat, rice, soybean, cotton, sugarbeet, oilseed rape, canola, flax, sunflower, potato, tobacco, tomato, alfalfa, lettuce, apple, poplar and pine.

23. A glyphosate tolerant plant of claim 22 in which the promoter region is from a DNA plant virus promoter region.

24. A glyphosate tolerant plant of claim 23 in which the promoter region is selected from the group consisting of CaMV35S and FMV35S promoter regions.

25. A DNA molecule of claim 2 in which the amino-terminal chloroplast transit peptide encoding 5' sequence of said structural DNA is selected from the group consisting of SEQ ID NO: 9 and SEQ ID NO: 10.

26. A DNA molecule of claim 14 in which the amino-terminal chloroplast transit peptide encoding 5' sequence of said structural DNA is selected from the group consisting of SEQ ID NO: 9 and SEQ ID NO: 10.

27. A method of claim 26 in which the amino-terminal chloroplast transit peptide has the sequence of a peptide encoded by a nucleotide sequence selected from the group consisting of SEQ ID NO: 9 and SEQ ID NO: 10.

28. A method for selectively controlling weeds in a field containing a crop of planted crop seeds or plants which method comprises the steps of:
   a) planting said crop seeds or plants which are glyphosate resistant as a result of a chimeric gene being inserted into said crop seed or plant, said chimeric gene having
      i) a promoter region which functions in plants to cause the production of an RNA sequence, operatively linked to;
      ii) a structural DNA sequence that causes the production of an RNA sequence which encodes a glyphosate oxidoreductase enzyme having the sequence of SEQ ID NO: 5, operatively linked to;
      iii) a 3' non-translated region which functions in plants to cause the addition of polyadenylated nucleotides to the 3' end of the RNA sequence;
   where the promoter region is heterologous with respect to the structural DNA sequence and causes sufficient expression of said enzyme in plant tissue to enhance the glyphosate tolerance of a plant transformed with said gene; and
   b) applying to said crop and weeds in said field a sufficient amount of glyphosate to control said weeds without significantly affecting said crop.

29. A method of claim 27 in which the structural DNA sequence further comprises a 5' sequence encoding an amino-terminal chloroplast transit peptide.

30. A method of claim 28 in which the promoter region is selected from the group consisting of CaMV35S and FMV35S promoter regions.

* * * * *